US005731188A

United States Patent [19]
Cochran et al.

[11] Patent Number: 5,731,188
[45] Date of Patent: Mar. 24, 1998

[54] RECOMBINANT EQUINE HERPESVIRUSES

[75] Inventors: Mark D. Cochran, Carlsbad; Christina H. Chiang, San Diego, both of Calif.

[73] Assignee: Syntro Corporation, Lenexa, Kans.

[21] Appl. No.: 323,531

[22] Filed: Oct. 14, 1994

Related U.S. Application Data

[63] Continuation of Ser. No. 926,784, Aug. 7, 1992, abandoned, which is a continuation-in-part of Ser. No. 914,057, Jul. 13, 1992, which is a continuation-in-part of Ser. No. 696,262, Apr. 30, 1991, abandoned, which is a continuation-in-part of Ser. No. 933,107, Nov. 20, 1986, abandoned.

[51] Int. Cl.[6] ............................ C12N 7/01; C12N 15/86

[52] U.S. Cl. .................................... 435/235.1; 435/320.1

[58] Field of Search ............................. 435/69.1, 172.1, 435/172.3, 240.2, 320.1, 235.1

[56] References Cited

U.S. PATENT DOCUMENTS 5,292,653 3/1994 Kit et al. ............................ 435/235.1

FOREIGN PATENT DOCUMENTS

WO 9201045 1/1992 WIPO .
WO 9201057 1/1992 WIPO .
WO9202252 2/1992 WIPO .

OTHER PUBLICATIONS

Saul Kit, "Genetically Engineered Pseudorabies and Infectious Bovine Rhinotracheitis Virus Vaccines", In: Technological Advances in Vaccine Development, pp. 183–195, 1988, Alan R. Liss, Inc.

Shih et al., "Expression of Hepatitis B Virus S Gene by Herpes Simplex Virus Type 1 Vectors Carrying α–and β–Regulated Gene Chimeras", PNAS, vol. 81, pp. 5867–5870, Sep. 1984.

Audonnet et al., "Equine Herpesvirus Type 1 Unique Short Fragment Encodes Glycoproteins with Homology to Herpes Simplex Virus Type 1 gD, gI and gE", J. Gen. Virol., vol. 71, 1990, pp. 2969–2978.

Meignier et al., "Virulence and Establishment of Latency by Genetically Engineered Deletion Mutants of Herpes Simplex Virus 1", Virology, vol. 162, pp. 251–254.

G.P. Allen, et al., "Use of λgtII and Monoclonal Antibodies To Map the Genes for the Six Major Glycoproteins of Equine Herpesvirus 1", J. Virol. (1987) 61: 2454–2461 (Exhibit 6).

G.P. Allen, et al., "Characterization of an Equine Herpesvirus Type 1 Gene Encoding a Glycoprotein (gp13) with Homology to Herpes Simplex Virus Glycoprotein C", J. Virol. (1988) 62: 2850–2858 (Exhibit 7).

J.C. Audonnet, et al., "Equine Herpesvirus Type 1 Unique Short Fragment Encodes Glycoproteins with Homology to Herpes Simplex Virus Type gD, gI and gE", J. Gen. Virol. (1990) 71: 2969–2978 (Exhibit 8).

R. Baumann, et al., "Genetic Relatedness and Colinearity of Genomes of Equine Herpesvirus Types 1 and 3", J. Virol. (1986) 57: 816–825 (Exhibit 9).

C. Bell, et al., "Transcript Analysis of the Equine Herpesvirus 1 Glycoprotein B Gene Homologue and Its Expression by a Recombinant Vaccinia Virus", J. Gen. Virol. (1990) 71: 1119–1129 (Exhibit 10).

C.F. Colle III, et al., "Open Reading Frames Encoding a Protein Kinase, Homolog of Glycoprotein gX of Pseudorabies Virus, and a Novel Glycoprotein Map within the Unique Short Segment of Equine Herpesvirus Type 1", Virol. (1992) 188: 545–557 (Exhibit 11).

J. Cornick, et al., "Safety and Efficacy of a Thymidine Kinase Negative Equine Herpesvirus–1 Vaccine in Young Horses", Canadian J. of Vet. Res. (1990) 54: 260–266 (Exhibit 12).

A.A. Cullinane, et al., "Characterization of the Genome of Equine Herpesvirus 1 Subtype 2", J. Gen. Virol. (1988) 69: 1575–1590 (Exhibit 13).

A.J. Davison, et al., "Location and Orientation of Homologous Sequences in the Genomes of Five Herpesviruses", J. Gen. Virol. (1983) 64: 1927–1942 (Exhibit 14).

D. Elton, et al., "Location of Open Reading Frames Coding for Equine Herpesvirus Type–1 Glycoproteins with Homology to gE and gI of Herpes Simplex Virus", Am. J. Vet. Res. (1991) 52: 1252–(Exhibit 15).

D.M. Elton, et al., "Sequence analysis of the 4.7–kb BamHI–EcoRI fragment of the equine herpesvirus type–1 short unique region", Gene (1991) 101: 203–208 (Exhibit 16).

D. Elton, et al., "Identification of the Equine Herpesvirus Type 1 Glycoprotein 17/18 as a Homologue of Herpes Simplex Virus Glycoprotein D", J. Gen. Virol. (1992) 73: 1227–1233 (Exhibit 17).

C.C. Flowers, et al., "Sequence Analysis of a Glycoprotein D. Gene Homolog within the Unique Short Segment of the EHV–1 Genome", Virology (1991) 180: 175–184 (Exhibit 18).

(List continued on next page.)

*Primary Examiner*—David Guzo
*Attorney, Agent, or Firm*—John P. White

[57] ABSTRACT

The present invention relates to a non-naturally occurring, recombinant equine herpesvirus. The invention also relates to a recombinant equine herpesvirus capable of replication which comprises viral DNA from a species of equine herpesvirus and foreign DNA, the foreign DNA being inserted into the equine herpesviral DNA at a site which is not essential for replication of the equine herpesvirus. The invention also relates to DNA encoding the US2 protein of an equine herpesvirus. The invention relates to homology vectors for producing recombinant equine herpesviruses which produce recombinant equine herpesviruses by inserting foreign DNA into equine herpesviral DNA. The invention further relates to a method of producing a fetal-safe, live recombinant equine herpesvirus.

23 Claims, 17 Drawing Sheets

OTHER PUBLICATIONS

P. Guo, "Characterization of the gene and an antigenic determinant of equine herpesvirus type-1 glycoprotein 14 with homology to gB–equivalent glycoproteins of other herpesviruses", Gene (1990) 87: 249–255 (Exhibit 19).

H.S. Nagesha, et al., "Cloning and Restriction Endonuclease Mapping of the Genome of an Equine Herpesvirus 4 (equine rhinopneumonitis virus), Strain 405/76", Arch. Virol. (1992) 124: 379–387 (Exhibit 20).

L. Nicolson and D.E. Onions, "The Nucleotide Sequence of an Equine Herpesvirus 4 Gene Homologue of the Herpes Simplex Virus 1 Glycoprotein H Gene", J. of Gen. Virol. (1990) 71: 1793–1800 (Exhibit 21).

L. Nicolson, et al., "The Nucleotide Sequence of the Equine Herpesvirus 4 gC Gene Homologue", Virology (1990) 179: 378–387 (Exhibit 22).

L. Nicolson, et al., "The Nucleotide Sequence of the Equine Herpesvirus 4 Thymidine Kinase Gene", J. Gen. Virol. (1990) 71: 1801–1805 (Exhibit 23).

M.P. Riggio, et al., "Identification and Nucleotide Sequence of the Glycoprotein gB Gene of Equine Herpesvirus 4", J. Virol. (1989) 63: 1123–1133 (Exhibit 24).

G. Robertson, et al., "Evolution of the Herpes Thymidine Kinase: Identification and Comparison of the Equine Herpesvirus 1 Thymidine Kinase Gene Reveals Similarity to a Cell–Encoded Thymidine Kinase", Nucleic Acids Research (1988) 16: 11303–11317 (Exhibit 25).

E. Telford, et al., "The DNA Sequence of Equine Herpesvirus–1", Virology (1992) 189: 304–316 (Exhibit 26).

M. Whalley, et al., "Identification and Nucleotide Sequence of a Gene in Equine Herpesvirus 1 Analogous to the Herpes Simplex Virus Gene Encoding the Major Envelope Glycoprotein gB", J. of Gen. Virol. (1989) 70: 383–394 (Exhibit 27).

M. Whalley, et al., "Identification and Comparative Sequence Analysis of a Gene in Equine Herpesvirus 1 with Homology to the Herpes Simplex Virus Glycoprotein D gene", Virus Genes (1991) 5: 313–325 (Exhibit 28).

| | | | |
|---|---|---|---|
| EHV-1 US2 | 123 | H-LWVLGAADLCKPVFDLI |
| EHV-4 US2 | 123 | H-LWVLGAADLCRPVFNLI |
| HSV-1 US2 | 124 | H-LWVVGAADLCVPFLEYA |
| HSV-2 US2 | 123 | H-LWVVGAADLCVPFFEYA |
| PRV US2 | 148 | H-LWILGAADLCDQVLLAA |
| MDV US2 | 132 | HSLWIVGAADICRIALECI |
| IBR US2 | 115 | H-MWVFGAADLYAPIFAHI |

RECOMBINANT EQUINE HERPESVIRUSES

This application is a continuation of U.S. Ser. No. 07/926,784, filed Aug. 7, 1992, now abandoned, which is a continuation-in-part of U.S. Ser. No. 07/914,057, filed Jul. 13, 1992, which is a continuation-in-part of U.S. Ser. No. 07/696,262, filed Apr. 30, 1991, now abandoned, which is a continuation-in-part of U.S. Ser. No. 06/933,107, filed Nov. 20, 1986, now abandoned, the contents of which are hereby incorporated by reference into the present application.

BACKGROUND OF THE INVENTION

Within this application, several publications are referenced by Arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

The present invention involves recombinant equine herpesviruses useful in the preparation of vaccines to protect horses from various species of naturally-occurring infectious equine herpesvirus. The equine herpesvirus is a member of the family herpesviridae, which are commonly known as the herpesviruses.

Generally, herpesviruses contain 100,000 to 200,000 base pairs of DNA as their genetic material, and several areas of the genomes of various members have been identified that are not essential for the replication of virus in vitro in cell culture. Modifications of these regions of the DNA have been known to lower the pathogenicity of the virus, i.e. to attenuate the virus when it infects an animal species. For example, inactivation of the thymidine kinase gene of either human herpes simplex virus (29) or pseudorabies virus of swine (38) renders these herpesviruses less pathogenic.

Removal of specific regions of the repeat region of a human herpes simplex virus have been shown to render the virus less pathogenic (32, 39). Furthermore, a repeat region has been identified in Marek's disease virus that is associated with viral oncogenicity (13). A region in herpesvirus saimiri has similarly been correlated with oncogenicity (21). Removal of a specific region of the repeat region renders pseudorabies virus less pathogenic (U.S. Pat. No. 4,877,737). A region in pseudorabies virus has been shown to be deleted in naturally-occurring vaccine strains (22). These deletions are at least in part responsible for the lack of pathogenicity of these strains.

It is generally agreed that herpesviruses contain non-essential regions of DNA in various parts of the genome, and that modification of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune response. Although several examples of attenuating deletions are known, the appropriate combination of deletions for any herpesvirus is not readily apparent.

Major economic losses to the equine industry result from infection by two species of equine herpesvirus (17). These two equine herpesvirus species, currently identified in the literature as EHV-1 and EHV-4, belong to the herpesvirus sub-family alpha-herpesvirus and are characterized by a class D genome (33). Formerly, both species were identified as EHV-1 and further differentiated as EHV-1 subtype 1 (EHV-1) and EHV-1 subtype 2 (EHV-4) respectively. EHV-1 is the primary cause of abortion in pregnant mares and EHV-4 is the primary cause of respiratory disease in foals and yearlings. Currently available products are not designed to address both disease syndromes, with the result that these products are marginally effective.

EHV-1 and EHV-4 have been analyzed at the molecular level. Restriction maps of the genomes of EHV-1 and EHV-4 have been reported (42 and 8).

Although several of the herpesviruses have been genetically engineered, no examples of recombinant EHV have been reported.

EHV can become latent in healthy animals which makes them potential carriers of the virus. For this reason, it is clearly advantageous to be able to distinguish animals vaccinated with non-virulent virus from animals infected with disease-causing wild-type or naturally-occurring virus. The development of differential vaccines and companion diagnostic tests has proven valuable in the management of pseudorabies disease (Federal Register, Vol. 55, No. 90, pp. 19245–19253). A similar differential marker vaccine would be of great value in the management of EHV caused disease.

The present invention provides a method of producing a fetal-safe, live recombinant EHV virus which comprises treating viral DNA from a naturally-occurring live EHV so as to delete from such viral DNA, DNA corresponding to the US2 gene of the naturally-occurring EHV. The present invention also provides viruses in which (a) DNA corresponding to the US2 gene has been deleted, and (b) DNA encoding gpG, gpE, and/or TK has been altered or deleted. Such viruses are useful for the creation of vaccines which require diagnostic markers and safety in pregnant animals.

The ability to engineer DNA viruses with large genomes, such as vaccinia virus and the herpesviruses, has led to the finding that these recombinant viruses can be used as vectors to deliver vaccine antigens and therapeutic agents for animals. The herpesviruses are attractive candidates for development as vectors because their host range is primarily limited to a single target species (16) and they have the capacity for establishing latent infection (7) that could provide for stable in vivo expression of a foreign gene. Although several herpesvirus species have been engineered to express foreign gene products, recombinant equine herpesviruses expressing foreign gene products have not been constructed. The equine herpesviruses described above may be used as vectors for the delivery of vaccine antigens from microorganisms causing important equine diseases. Such multivalent recombinant viruses would protect against EHV as well as other diseases. Similarly the equine herpesviruses may be used as vectors for the delivery of therapeutic agents. The therapeutic agent that is delivered by a viral vector of the present invention must be a biological molecule that is a by-product of equine herpesvirus replication. This limits the therapeutic agent in the first analysis to either DNA, RNA or protein. There are examples of therapeutic agents from each of these classes of compounds in the form of anti-sense DNA, anti-sense RNA (19), ribozymes (41), suppressor tRNAs (3), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not necessarily allow one to use them in a viral vector delivery system; however, because of the experimentation necessary to determine whether an appropriate insertion site exists.

SUMMARY OF THE INVENTION

The invention provides a non-naturally occurring, recombinant equine herpesvirus. The invention provides isolated DNA encoding the US2 protein of an equine herpesvirus.

The invention provides a recombinant equine herpesvirus capable of replication which comprises viral DNA from a species of a naturally-occurring equine herpesvirus and foreign DNA encoding RNA which does not naturally occur in an animal into which the recombinant equine herpesvirus is introduced, the foreign DNA being inserted into the naturally-occurring equine herpesviral DNA at a site which is not essential for replication of the equine herpesvirus.

The invention provides a homology vector for producing a recombinant equine herpesvirus by inserting foreign DNA into a genome of an equine herpesvirus which comprises a double-stranded DNA molecule consisting essentially of: a) a double-stranded foreign DNA sequence encoding RNA which does not naturally occur in an animal into which the recombinant equine herpesvirus is introduced; b) at one end of the foreign DNA sequence, double-stranded equine herpesviral DNA homologous to genomic DNA located at one side of a site on the genome which is not essential for replication of the equine herpesvirus; and c) at the other end of the foreign DNA, double-stranded equine herpesviral DNA homologous to genomic DNA located at the other side of the same site on the genome.

The invention provides a method of producing a fetal-safe, live recombinant equine herpesvirus which comprises treating viral DNA from a naturally-occurring live equine herpesvirus so as to delete from the virus DNA corresponding to the US2 region of the naturally-occurring equine herpesvirus.

BRIEF DESCRIPTION OF THE FIGURES

FIG. 3A Matrix plot of the amino acid sequence of the EHV-4 US2 protein (324 amino acids) (SEQ ID NO: 4) against the amino acid sequence of the HSV-1 US2 protein (291 amino acids) (24). FIG. 3B Alignment of the conserved region (SEQ. ID NO: 7) between EHV-1 US2 protein (303 amino acids) (SEQ ID NO: 2), EHV-4 US2 protein (SEQ ID NO: 8), HSV-1 US2 protein (SEQ ID NO: 9), PRV US2 protein (SEQ. ID NO: 11) (256 amino acids) (49) HSV-2 US2 protein (SEQ ID NO: 10) (291 amino acids) (25), MDV US2 protein (SEQ ID NO: 12) (270 amino acids) (4), and IBR US2 (SEQ ID NO: 13).

DETAILED DESCRIPTION OF THE INVENTION

Figure 1:
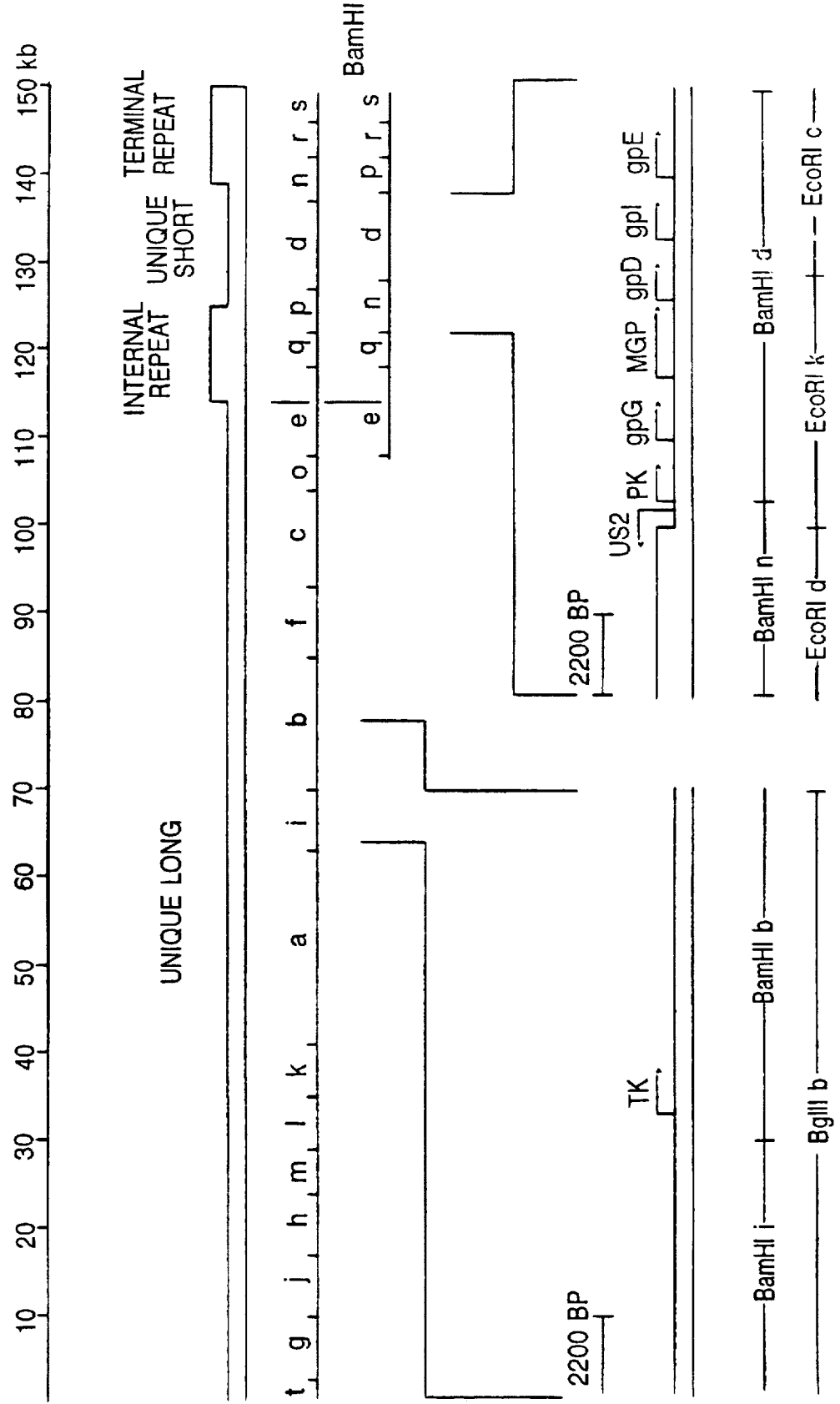
FIG. 1 Details of the EHV1 Dutta Strain. Diagram of EHV1 genomic DNA showing the unique long, internal repeat, unique short, and Terminal repeat regions. A restriction map for the enzyme BamHI is indicated (42). Fragments are lettered in order of decreasing size. The unique short region and the thymidine kinase region are expanded showing the locations of fragments BglII b, EcoRI d, k and c. The location of several genes is indicated they are thymidine kinase (Tk), unique short 2 (US2), glycoproteins G (gpG), D (gpD), I (gpI), and E (gpE) (1).

The present invention provides a non-naturally occurring, recombinant equine herpesvirus. The invention further provides that this recombinant equine herpesvirus is of the species EHV-1 and EHV-4.

For purposes of this invention, the term "equine herpesvirus" includes, but is not limited to, the species EHV-1 and EHV-4. These species were previously referred to in the literature as EHV-1, subtype 1 and EHV-1 subtype 2, respectively.

The invention further provides a recombinant equine herpesvirus wherein a DNA sequence which is not essential for replication of the virus has been deleted from the genomic DNA of the virus.

For purposes of this invention, "a DNA sequence which is not essential for replication of the virus" is a sequence located on the genome where it does not serve a necessary function for viral replication. Examples of necessary sequences include the following: complex protein binding sequences, sequences which code for reverse transcriptase or an essential glycoprotein, DNA sequences necessary for packaging, etc.

One embodiment of the present invention provides a recombinant equine herpesvirus wherein the deleted DNA sequence is deleted from a gene which encodes a polypeptide of the virus. Preferably, the deleted sequence is deleted from the US2 gene of the virus. The present invention provides an example of such a recombinant equine herpesvirus designated S-1EHV-002 with the ATCC Accession No. VR 2358. Preferably, the deleted DNA sequence is deleted from the gene which encodes the gpG glycoprotein. Preferably, the deleted DNA sequence is deleted from the gene which encodes the gpE glycoprotein. Preferably, the deleted DNA sequence is deleted from the thymidine kinase gene of the virus. The present invention provides an example of such a recombinant equine herpesvirus designated S-1EHV-001 with ATCC Accession No. VR 2357. The present invention provides a further example of such a recombinant equine herpesvirus designated S-4EHV-001 with ATCC Accession No. VR 2361.

The invention also provides a recombinant equine herpesvirus with a deleted DNA sequence deleted from the thymidine kinase gene of the virus and a second DNA sequence which is not essential for replication of the virus deleted from the genomic DNA of the virus. An embodiment of this invention is a recombinant equine herpesvirus wherein the second deleted DNA sequence is deleted from the US2 gene of the virus. The present invention provides an example of such a recombinant equine herpesvirus designated S-1EHV-004 with ATCC Accession No. VR 2360. The present invention provides a further example of such a recombinant equine herpesvirus designated S-4EHV-002 with ATCC Accession No. VR 2362.

The invention also provides a recombinant equine herpesvirus with a deleted DNA sequence deleted from the thymidine kinase gene of the virus, a second deleted DNA sequence deleted from the US2 gene of the virus and a third DNA sequence which is not essential for the replication of the virus deleted from the genomic DNA of the virus. An embodiment of this invention is a recombinant equine herpesvirus wherein the deleted third DNA sequence is deleted from the gpG gene of the virus. The present invention provides an example of such a recombinant equine herpesvirus designated S-1EHV-003 with ATCC Accession No. VR2359. A further embodiment of this invention is a recombinant equine herpesvirus wherein the deleted third DNA sequence is deleted from the gpE gene of the virus.

The present invention provides isolated DNA encoding the US2 protein of an equine herpesvirus.

The present invention provides a recombinant equine herpesvirus capable of replication which comprises viral DNA from a species of a naturally-occurring equine herpesvirus and foreign DNA encoding RNA which does not naturally occur in an animal into which the recombinant equine herpesvirus is introduced, the foreign DNA being inserted into the naturally-occurring equine herpesviral DNA at a site which is not essential for replication of the equine herpesvirus.

For purposes of this invention, "a recombinant equine herpesvirus capable of replication" is a live equine herpesvirus which has been generated by the recombinant methods well known to those of skill in the art, e.g., the methods set forth in HOMOLOGOUS RECOMBINATION PROCEDURE FOR GENERATING RECOMBINANT EHV in Materials and Methods and has not had genetic material essential for the replication of the recombinant equine herpesvirus deleted.

For purposes of this invention, "an insertion site which is not essential for replication of the equine herpesvirus" is a location in the genome where a sequence of DNA is not necessary for viral replication. Examples of DNA sequences which are essential include the following: complex protein binding sequences, sequences which code for reverse transcriptase or an essential glycoprotein, DNA sequences necessary for packaging, etc.

The invention further provides foreign DNA encoding RNA which encodes a polypeptide. Preferably, the polypeptide is antigenic in an animal into which the recombinant equine herpesvirus is introduced. In one embodiment of the invention, the polypeptide is a detectable marker. Preferably, the polypeptide is $E.\ coli$ β-galactosidase. Preferably, the polypeptide is $E.\ coli$ β-glucuronidase. The present invention provides an example of such a recombinant equine herpesvirus designated S-4EHV-004.

For purposes of this invention, this antigenic polypeptide is a linear polymer of more than 10 amino acids linked by peptide bonds which stimulates the animal to produce antibodies.

In one embodiment of the invention, the polypeptide is a polypeptide normally produced by an equine herpesvirus, a *Streptococcus equi* bacterium, an Infectious Anemic Virus, an equine influenza virus or an equine encephalitis virus. Preferably, the naturally occurring equine herpesvirus is EHV-1 and the foreign DNA is derived from EHV-4. Preferably, the naturally-occurring equine herpesvirus is EHV-4 and the foreign DNA is derived from EHV-1. Preferably, the foreign DNA encodes a gpB, gpC, gpD or gpH glycoprotein.

The present invention also provides a recombinant equine herpesvirus capable of replication which comprises viral DNA from a species of a naturally-occurring equine herpesvirus and foreign DNA encoding RNA which does not naturally occur in an animal into which the recombinant equine herpesvirus is introduced, the foreign DNA being inserted into the naturally-occurring equine herpesviral DNA at a site which is not essential for replication of the equine herpesvirus with the DNA sequence which is not essential for replication of the virus deleted from the genomic DNA of the virus. In one embodiment of the present invention, the deleted DNA sequence is deleted from a gene which encodes a polypeptide of the virus. Preferably, the foreign DNA is inserted into the naturally-occurring herpesviral DNA at a site where a DNA sequence has been deleted. Preferably, the deleted DNA sequence is deleted from the US2, Tk, and gpE genes of the virus.

In one embodiment of the present invention, the naturally-occurring equine herpesvirus is EHV-4 and the antigenic polypeptide is or is from the gpD and gpB gene of the EHV-1 species of equine herpesvirus. The present invention provides an example of such a recombinant equine herpesvirus designated S-4EHV-010.

In another embodiment of the present invention, the naturally-occurring equine herpesvirus is EHV-4 and the antigenic polypeptide is or is from the hemagglutinin and neuraminidase genes of a subtype of equine influenza A virus. Preferably, the subtype of equine influenza A virus serotype is A1. Preferably, the subtype is further characterized as an isolate of the A1 subtype of equine influenza A virus. Preferably, the isolate is Influenza A/equine/Prague/56. The present invention provides an example of such a recombinant equine herpesvirus designated S-4EHV-011 ATCC Accession No. VR 2497, deposited with the American Type Culture Collection on Mar. 12, 1992 pursuant to the Budapest Treaty on the International Deposit of Microorganisms for the Purposes of Patent Procedure with the Patent Culture Depository of the American Type Culture located at 12301 Parklawn Drive, Rockville, Md.

In another embodiment of the present invention, the subtype of equine influenza A virus is A2. Preferably, the subtype is further characterized as an isolate of the A2 subtype of equine influenza A virus. Preferably, the isolate is Influenza A/equine/Miami/63. Preferably, the isolate is Influenza A/equine/Kentucky/81. Preferably, the isolate is Influenza A/equine/Alaska/91. The present invention provides examples of such recombinant equine herpesviruses designated S-4EHV-012 ATCC Accession No. VR 2498, deposited with the American Type Culture Collection on Mar. 12, 1992 pursuant to the Budapest Treaty on the International Deposit of Microorganisms for the Purposes of Patent Procedure with the Patent Culture Depository of the American Type Culture located at 12301 Parklawn Drive, Rockville, Md., S-4EHV-013 ATCC Accession No. VR 2499 deposited with the American Type Culture Collection on Mar. 12, 1992 pursuant to the Budapest Treaty on the International Deposit of Microorganisms for the Purposes of Patent Procedure with the Patent Culture Depository of the American Type Culture located at 12301 Parklawn Drive, Rockville, Md. and S-4EHV-014 ATCC Accession No. VR 2444 deposited with the American Type Culture Collection on February 16, 1994 pursuant to the Budapest Treaty on the International Deposit of Microorganisms for the Purposes of Patent Procedure with the Patent Culture Depository of the American Type Culture located at 12301 Parklawn Drive, Rockville, Md., respectively.

The present invention provides a homology vector for producing a recombinant equine herpesvirus by inserting foreign DNA into a genome of an equine herpesvirus which comprises a double-stranded DNA molecule consisting essentially of: a) a double-stranded foreign DNA sequence encoding RNA which does not naturally occur in an animal into which the recombinant equine herpesvirus is introduced; b) at one end of the foreign DNA sequence, double-stranded equine herpesviral DNA homologous to genomic DNA located at one side of a site on the genome which is not essential for replication of the equine herpesvirus; and c) at the other end of the foreign DNA sequence, double-stranded equine herpesviral DNA homologous to genomic DNA located at the other side of the same site on the genome. In one embodiment of the invention, the equine herpesvirus is EHV-1.

In another embodiment of the present invention, the equine herpesvirus is EHV-4. Preferably, the site on the genome which is not essential for replication is present within a DNA sequence included within the US2, TK, gpG or gpE gene. In one embodiment of the present invention, the double-stranded equine herpesviral DNA is homologous to genomic DNA present within the EHV-1 BglII restriction fragment b. Preferably, the double-stranded equine herpesviral DNA is homologous to a Sau3A restriction sub-fragment and a BstEII to PstI restriction sub-fragment. In another embodiment of the present invention, the double-stranded equine herpesviral DNA is homologous to genomic DNA present within the EHV-1 BamHI restriction fragment n. Preferably, the double-stranded equine herpesviral DNA is homologous to genomic DNA present within the BamHI to NcoI restriction sub-fragment and the EcoRI to PstI restriction sub-fragment. In a further embodiment of the present invention, the double-stranded equine herpesviral DNA is homologous to genomic DNA present within the EHV-1 EcoRI restriction fragment k. Preferably, the double-stranded equine herpesviral DNA is homologous to genomic DNA present within the EcoRI to PvuII restriction sub-fragment and the PstI to BamHI restriction sub-fragment. In another embodiment of the present invention, the double-stranded equine herpesviral DNA is homologous to genomic DNA present within the EHV-4 BamHI restriction fragment c. Preferably, the double-stranded equine herpesviral DNA is homologous to genomic DNA present within the PvuII to FspI restriction sub-fragment and the PvuII to SmaI restriction sub-fragment. In a further embodiment of the present invention, the double-stranded herpesviral DNA is homologous to genomic DNA present within the EHV-4 BamHI restriction fragment d. Preferably, the double-stranded herpesviral DNA is homologous to genomic DNA present within the XbaI to PstI restriction sub-fragment and the PstI to HindIII restriction sub-fragment. In another embodiment of the present invention, the double-stranded herpesviral DNA is homologous to genomic DNA present within the EHV-4 EcoRI restriction fragment j. Preferably, the double-stranded herpesviral DNA is homologous to genomic DNA present within the EcoRI to AatII restriction sub-fragment and the FspI to FspI restriction sub-fragment.

The present invention also provides a homology vector wherein the foreign DNA to be inserted corresponds to DNA encoding the gpH, gpB, gpD or gpC gene of an equine herpesvirus EHV-1 species. The present invention also provides a homology vector wherein the foreign DNA to be inserted corresponds to DNA encoding gpH, gpB, gpD or gpC glycoprotein of an equine herpesvirus EHV-4 species.

The present invention also provides a vaccine which comprises an effective immunizing amount of the recombinant equine herpesvirus of the present invention and a suitable carrier.

Suitable carriers for the equine herpesvirus, which would be appropriate for use with the recombinant equine herpesviruses of the present invention, are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant equine herpesvirus of the present invention is an amount necessary to stimulate the production of antibodies by the equine in which the virus was introduced in numbers sufficient to protect the equine from infection if it was confronted by a wild-type equine herpesvirus or other equine virus which the recombinant equine herpesvirus is directed to.

The present invention also provides a method of immunizing an equine which comprises administering an effective immunizing dose of the vaccine of the present invention.

For purposes of this invention, the vaccine may be administered by any of the methods well known to those skilled in the art, for example, by intramuscular, subcutaneous, intraperitoneal or intravenous injection. Alternatively, the vaccine may be administered intranasally or orally.

The present invention also provides for a method for testing an equine to determine whether the equine has been vaccinated with the vaccine of the present invention or is infected with a naturally-occurring equine herpesvirus which comprises: (a) obtaining from the equine to be tested a sample of a suitable body fluid; (b) detecting in the sample the presence of antibodies to equine herpesvirus, the absence of such antibodies indicating that the equine has been neither vaccinated nor infected; and (c) for the equine in which antibodies to equine herpesvirus are present, detecting in the sample the absence of antibodies to equine herpesviral antigens which are normally present in the body fluid of an equine infected by the naturally-occurring equine herpesvirus but which are not present in a vaccinated equine, the absence of such antibodies indicating that the equine was vaccinated and is not infected. In one embodiment of the invention, the equine herpesviral antigen not present in the vaccinated equine is gpE glycoprotein.

The present invention provides a method of producing a fetal-safe, live recombinant equine herpesvirus which comprises treating viral DNA from a naturally-occurring live equine herpesvirus so as to delete from the virus DNA corresponding to the US2 region of the naturally-occurring equine herpesvirus.

The present invention also provides a host cell infected with the recombinant equine herpesvirus of the present invention. In one embodiment, the host cell is a mammalian cell. Preferably, the mammalian cell is a vero cell.

For purposes of this invention, a "host cell" is a cell used to propagate a vector and its insert. Infecting the cells was accomplished by methods well known to those of skill in the art, for example, as set forth in INFECTION—TRANSFECTION PROCEDURE in Materials and Methods.

Methods for constructing, selecting and purifying recombinant equine herpesviruses are detailed below in Materials and Methods.

Materials and Methods

PREPARATION OF EHV VIRUS STOCK SAMPLES. S-1EHV-000 and S-4EHV-000 are fresh isolates of EHV-1 and EHV-4, respectively, and were obtained from Dr. S. K. Dutta (College of Veternary Medicine, University of Maryland, College Park, Md. 20742). EHV virus stock samples were prepared by infecting Vero cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Cells were resuspended in 1/10 the original volume of medium, and an equal volume of skim milk (9% skim milk powder in $H_2O$ weight/volume) was added. The virus samples were frozen at −70° C. The titers were approximately $10^8$ PFU/ml for EHV-1 and approximately $10^7$ PFU/ml for EHV-4.

PREPARATION OF HERPESVIRUS DNA. For herpesvirus DNA preparation, a confluent monolayer of Vero cells in a 25 $cm^2$ flask or 60 mm petri dish was infected with 100 µl of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml solution containing 0.5% NONIDET P-40™ (octyl phenol ethylene oxide condensate containing an average of 9 moles of ethylene oxide per molecule) (NP-40, purchased from Sigma Chemical Co., St. Louis, Mo.). The sample was incubated at room temperature for 10 minutes. Ten µl of a stock solution of RNase A (Sigma) were added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 µl of 20% sodium dodecyl sulfate (Sigma) and 25 µl proteinase-K (10 mg/ml; Boehringer Mannheim). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at −20° C. for 30 minutes to precipitate nucleic acid. The sample was centrifuged in an Eppendorf minifuge for 5 minutes. The supernatant was decanted, and the pellet was air dried and rehydrated in ~16 µl $H_2O$. For the preparation of larger amounts of DNA, the procedure was scaled up to start with a 850 $cm^2$ roller bottle of Vero cells. The DNA was stored in 0.01M tris pH 7.5, 1 mM EDTA at 4° C.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). The polymerase chain reaction (PCR) was used to introduce restriction sites convenient for the manipulation of various DNAs. The procedures used are described by Innis et al (1990). In general, amplified fragments were less than 500 base pairs in size and critical regions of amplified fragments were confirmed by DNA sequencing. Except as noted, these techniques were used with minor variations.

LIGATION. DNA was joined together by the action of the enzyme T4 DNA ligase (BRL). Ligation reactions contained various amounts of DNA (from 0.2 to 20 µg), 20 mM Tris pH 7.5, 10 mM $MgCl_2$, 10 mM dithiothreitol (DTT), 200 µM ATP and 20 units T4 DNA ligase in 10–20 µl final reaction volume. The ligation proceeded for 3–16 hours at 15° C.

DNA SEQUENCING. Sequencing was performed using the USB Sequenase Kit and $^{35}S$-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. The sequence obtained was assembled and compared using Dnastar software. Manipulation and comparison of sequences obtained was performed with Superclone and Supersee programs from Coral Software.

SOUTHERN BLOTTING OF DNA. The general procedure for Southern blotting was taken from Maniatis et al. DNA was blotted to nitrocellulose filters and hybridized to appropriate labeled DNA probes. Probes for southern blots were prepared using either the Nonradioactive DNA Labeling and Detection Kit of Boehringer Mannheim or the nick translation kit of Bethesda Research Laboratories (BRL). In both cases the manufacturer's recommended procedures were followed.

DNA TRANSFECTION FOR GENERATING RECOMBINANT VIRUS. The method is based upon the calcium phosphate procedure of Graham and Van der eb (1973) with the following modifications. Virus and/or Plasmid DNA were diluted to 298 µl in 0.01M Tris pH 7.5, 1 mM EDTA. Forty µl 2M $CaCl_2$ was added followed by an equal volume of 2×HEPES buffered saline (10 g N-2-hydroxyethyl piperazine N'-2-ethanesulfonic acid (HEPES), 16 g NaCl, 0.74 g KCl, 0.25 g $Na_2HPO_4.2H_2O$, 2 g dextrose per liter $H_2O$ and buffered with NaOH to pH 7.4). The mixture was then incubated on ice for 10 minutes, and then added dropwise to an 80% confluent monolayer of Vero cells growing in a 60 mm petri dish under 5 ml of medium (DME plus 1% fetal bovine serum). The cells were incubated 4 hours at 37° C. in a humidified incubator containing 5% $CO_2$. The cells were then washed once with. 5 ml of 1×PBS (1.15 g $Na_2HPO_4$, 0.2 g $KH_2PO_4$, 0.8 g NaCl, 0.2 g KCl per liter $H_2O$), once with 5 ml of 20% glycerol/PBS (v/v), once more with 5 ml 1×PBS, and then fed with 5ml of medium (DME plus 2% fetal bovine serum). The cells were incubated at 37° C. as above for 3-7 days until cytopathic effect from the virus was 50-100%. Virus was harvested as described above for the preparation of virus stocks. This stock was referred to as a transfection stock and was subsequently screened for recombinant virus by the SCREEN FOR RECOMBINANT HERPESVIRUS EXPRESSING ENZYMATIC MARKER GENES.

HOMOLOGOUS RECOMBINATION PROCEDURE FOR GENERATING RECOMBINANT HERPESVIRUS. This method relies upon the homologous recombination between herpesvirus DNA and plasmid homology vector DNA which occurs in tissue culture cells co-transfected with these elements. From 0.1-1.0 µg of plasmid DNA containing foreign DNA flanked by appropriate herpesvirus cloned sequences (the homology vector) were mixed with approximately 0.3 µg of intact herpesvirus DNA. The DNAs were diluted to 298 µl in 0.01M Tris pH 7.5, 1 mM EDTA and transfected into Vero cells according to the DNA TRANSFECTION FOR GENERATING RECOMBINANT VIRUS (see above).

Figure 2:
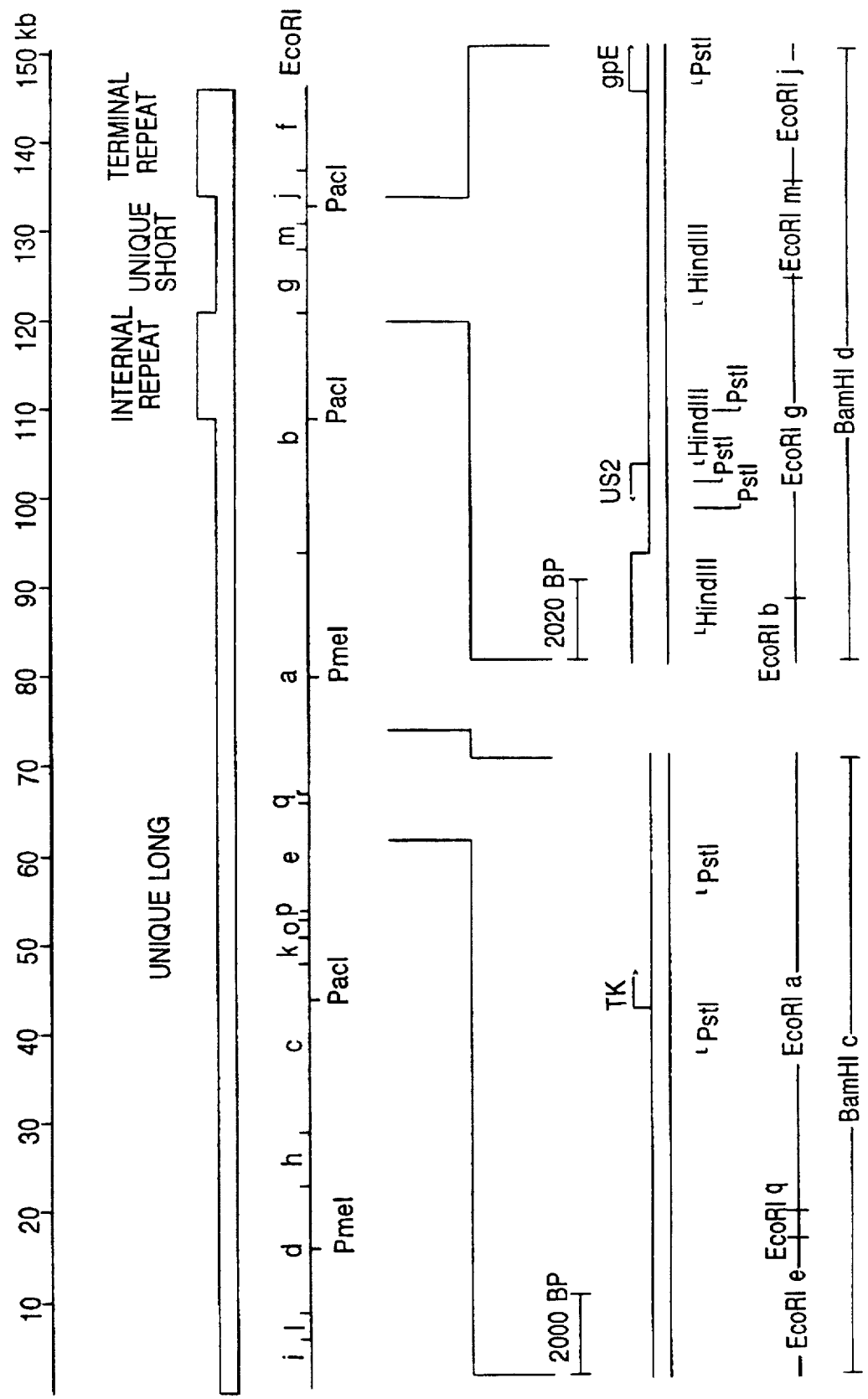
FIG. 2 Details of the EHV4 Dutta Strain. Diagram of EHV4 genomic DNA showing the unique long, internal repeat, unique short, and Terminal repeat regions. Restriction maps for the enzymes EcoRI, PacI and PmeI are indicated. Fragments are lettered in order of decreasing size. The unique short region and the thymidine kinase region are expanded showing the locations of fragments BamHI c, d. The locations of two genes are also indicated, they are thymidine kinase (Tk) (27, 28) and unique short 2 (US2).

DIRECT LIGATION PROCEDURE FOR GENERATING RECOMBINANT HERPESVIRUS. Rather than using homology vectors and relying upon homologous recombination to generate recombinant virus, we have also developed the technique of direct ligation to engineer herpesviruses. In this instance, a cloned foreign gene did not require flanking herpesvirus DNA sequences but only required that it have restriction sites available to cut out the foreign gene fragment from the plasmid vector. A compatible restriction enzyme was used to cut herpesvirus DNA. A requirement of the technique is that the restriction enzyme used to cut the herpesvirus DNA must cut at a limited number of sites. For EHV-4 the restriction enzymes PmeI or PacI would be appropriate (see FIG. 2). Restriction sites previously introduced into herpesviruses by other methods may also be used. The herpesvirus DNA is mixed with a 30-fold molar excess of plasmid DNA (typically 5 μg of virus DNA to 10 μg of plasmid DNA), and the mixture is cut with the appropriate restriction enzyme. The DNA mixture is phenol extracted and ethanol precipitated to remove restriction enzymes, and ligated together according to the ligation procedure detailed above. The ligated DNA mixture is then resuspended in 298 μl 0.01M Tris pH 7.5, 1 mM EDTA and transfected into Vero cells according to the DNA TRANSFECTION FOR GENERATING RECOMBINANT VIRUS (see above).

PROCEDURE FOR GENERATING RECOMBINANT HERPESVIRUS FROM SUBGENOMIC DNA FRAGMENTS. The ability to generate herpesviruses by cotransfection of cloned overlapping subgenomic fragments has been demonstrated for pseudorabies virus (48) and for herpesvirus of turkeys (47). If deletions and/or insertions are engineered directly into the subgenomic fragments prior to the cotransfection, this procedure results in a high frequency of viruses containing the genomic alteration, greatly reducing the amount of screening required to purify the recombinant virus. We anticipate utilizing this technique to engineer foreign gene insertions into specific attenuating deletions (US2, TK, and gpE) in EHV-4. In the first step of this procedure deletions are introduced into separate viruses via homologous recombination with enzymatic marker genes as described below. The homology vector used in this step is constructed such that the enzymatic marker gene is flanked by a restriction enzyme site that does not cut EHV-4 in the region of the DNA to be deleted. In the second step a library of overlapping subgenomic fragments, capable of regenerating wild-type virus, is constructed from randomly sheared 4EHV-000 DNA. In the third step subgenomic fragments are cloned from each of the individual recombinant viruses containing attenuating deletion/marker gene insertions, which were generated in the first step. In each case the subcloned fragment corresponds in size and location to one of the wild-type subgenomic fragments constructed in the second step. This is accomplished by screening a library of randomly sheared recombinant virus DNA subclones with probes generated from the ends of the appropriate wild-type subgenomic fragment. The restriction sites which had been engineered to flank the marker genes in the first step are now utilized to replace the marker genes in each subgenomic fragment with various foreign genes (such as 1EHV gpB, 1EHV gpD, equine influenza HA, or equine influenza NA). In the fourth step cotransfection of the appropriate overlapping wild type and deletion/insertion derived subgenomic fragments permits the generation of recombinant EHV-4 viruses incorporating any desired combination of deletions and/or insertions.

SCREEN FOR RECOMBINANT HERPESVIRUS EXPRESSING ENZYMATIC MARKER GENES. When the *E. coli* β-galactosidase (lacZ) or β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the lacZ marker gene the substrate "BLUOGAL" (halogenated indolyl-β-D-galactosidase, GIBCO-Bethesda Research Labs) was used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh Vero cells and purified by further blue plaque isolation. In recombinant virus strategies in which the enzymatic marker gene is removed the assay involves plaque purifying white plaques from a background of parental blue plaques. In both cases viruses were typically purified with three rounds of plaque purification.

SELECTION OF ARA-T RESISTANT VIRUS. Many nucleoside analogs inhibit alpha-herpesvirus replication. One such antiviral drug is arabinosylthymine (Ara-T; Rayo Chemicals, Canada). Resistance of EHV mutants to Ara-T is due to mutations in the viral TK, so that TK negative (TK−) viruses are selected. The transfection stocks were grown on Vero cells in the presence of 200 μg/ml Ara-T in complete DME medium plus 1% fetal bovine serum. The selection was repeated one to two times. The virus stocks generated from Ara-T selection were assayed by thymidine plaque autoradiography (37, 38). Plaques picked from positive stocks were assayed for TK deletion by the SOUTHERN BLOTTING OF DNA procedure. Note that TK negative viruses constructed utilizing Ara-T selection (S-1EHV-001 and S-4EHV-001) exhibited changes in restriction fragments not related to the TK locus. Differences were observed in BamHI fragments c, d, and g in S-4EHV-001 and fragment p in S-1EHV-001. Since similar changes were not observed in S-4EHV-004 in which the TK deletion was introduced without Ara-T selection, we feel that this procedure is a less desirable procedure for the selection of recombinant viruses.

CONSTRUCTION OF DELETION VIRUSES. The strategy used to construct deletion viruses involved the use of either homologous recombination and/or direct ligation techniques. Initially a virus was constructed via homologous recombination, in which the DNA to be deleted was replaced with a marker gene such as *E. coli* β-galactosidase (lacZ) or β-glucuronidase (uidA). A second virus was then constructed in which the marker gene was deleted either by homologous recombination or via direct ligation. The advantage of this strategy is that both viruses may be purified by the SCREEN FOR RECOMBINANT HERPESVIRUS EXPRESSING ENZYMATIC MARKER GENES. The first virus is purified by picking blue plaques from a white plaque background, the second virus is purified by picking white plaques from a blue plaque background.

Figure 8:
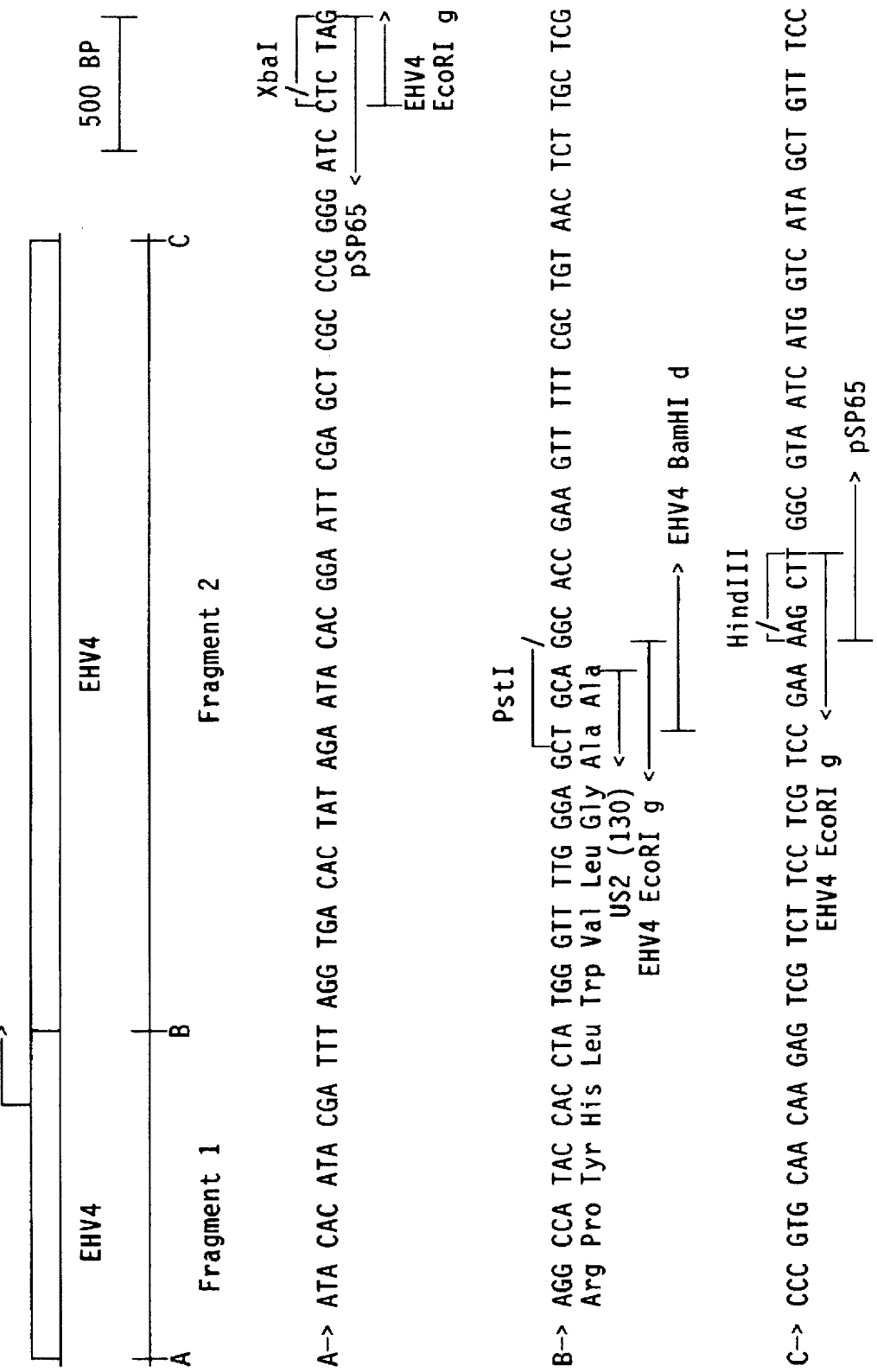
FIG. 8 Detailed description of the DNA insertion in Homology Vector 523-38.9. The diagram shows the orientation of DNA fragments assembled in plasmid 523-38.9. The origin of each fragment is described in the Materials and Methods section. The sequences located at the junctions between each fragment are shown, including junction A (SEQ ID NO: 33), junction B (SEQ ID NO: 34), and junction C (SEQ ID NO: 36). The restriction sites used to generate each fragment are indicated at the appropriate junction. The location of the US2 gene coding region is also given. The following two conventions are used: numbers in parenthesis ( ) refer to amino acids, and restriction sites in brackets [ ] indicate the remnants of sites which were destroyed during construction. The following abbreviations are used, equine herpesvirus 4 (EHV4) and unique short 2 (US2).

CLONING OF EQUINE INFLUENZA VIRUS HEMAGGLUTININ AND NEURAMINIDASE GENES. The equine influenza virus hemagglutinin (HA) and Neuraminidase (NA) genes may be cloned essentially as described by Katz et al. for the HA gene of human influenza virus. Viral RNA prepared from virus grown in MDBK cells is first converted to cDNA utilizing an oligo nucleotide primer specific for the target gene. The cDNA is then used as a template for PCR cloning (51) of the targeted gene region. The PCR primers are designed to incorporate restriction sites which permit the cloning of the amplified coding regions into vectors containing the appropriate signals for expression in EHV. One pair of oligo nucleotide primers will be required for each coding region. The HA gene coding regions from the serotype 2 (H3) viruses (Influenza A/equine/Miami/63, Influenza A/equine/Kentucky/81, and Influenza A/equine/Alaska/91) would be cloned utilizing the following primers 5'-GGGTCGACATGACAGACAACCATTATTTTGATAC-3' (SEQ ID NO: 64) for cDNA priming and combined with 5'-GGGTCGACTCAAATGCAAATGTTGCATCTGAT-3' (SEQ ID NO: 65) for PCR. The HA gene coding region from the serotype 1 (H7) virus (Influenza A/equine/Prague/56) would be cloned utilizing the following primers 5'-GGGATCCATGAACACTCAAATTCTAATATTAG-3' (SEQ ID NO: 66) for cDNA priming and combined with 5'-GGGATCCTTATATACAAATAGTGCACCGCA-3' (SEQ ID NO: 67) for PCR. The NA gene coding regions from the serotype 2 (N8) viruses (Influenza A/equine/Miami/63, Influenza A/equine/Kentucky/81, and Influenza A/equine/Alaska/91) would be cloned utilizing the following primers 5'-GGGTCGACATGAATCCAAATCAAAAGATAA-3' (SEQ ID NO: 68) for cDNA priming and combined with 5'-GGGTCGACTTACATCTTATCGATGTCAAA-3' (SEQ ID NO: 69) for PCR. The NA gene coding region from the serotype 1 (N7) virus (Influenza/A/equine/Prague/56) would be cloned utilizing the following primers 5'-GGGATCCATGAATCCTAATCAAAAACTCTTT-3' (SEQ ID NO: 68) for cDNA priming and combined with 5'-GGGATCCTTACGAAAAGTATTTAATTTGTGC-3' (SEQ ID NO: 71) for PCR. Note that this general strategy may be used to clone the coding regions of HA and NA genes from other strains of equine influenza A virus.

HOMOLOGY VECTOR 450-46.B4. The plasmid 450-46.B4 was constructed for the purpose of deleting a portion of the EHV-1 thymidine kinase gene. It may also be used to insert foreign DNA into EHV1. It contains a unique XbaI restriction enzyme site into which foreign DNA may be inserted. It may be constructed utilizing standard recombinant DNA techniques (23 and 34), by joining restriction fragments from the following sources with the synthetic DNA sequences indicated in FIG. 8. The plasmid vector is derived from an approximately 2978 base pair BamHI to HindIII restriction fragment of pSP65 (Promega). Fragment 1 is an approximately 779 base pair Sau3A restriction sub-fragment of the EHV1 BglII restriction fragment b (42). Fragment 2 is an approximately 1504 base pair BstEII to PstI restriction sub-fragment of EHV1 BglII restriction fragment b (42).

HOMOLOGY VECTOR 467-21.19. The plasmid 467-21.19 was constructed for the purpose of deleting a portion of the EHV1 unique short 2 gene. It may also be used to insert foreign DNA into EHV1. It contains a unique EcoRI restriction enzyme site into which foreign DNA may be inserted. It may be constructed utilizing standard recombinant DNA techniques (23, 34) by joining restriction fragments from the following sources as indicated in FIG. 5. The plasmid vector is derived from an approximately 2983 base pair BamHI to PstI restriction fragment of pSP65 (Promega). Note that the EcoRI site has been removed from the plasmid vector by nuclease S1 digestion. Fragment 1 is an approximately 767 base pair BamHI to NcoI restriction sub-fragment of the EHV1 BamHI restriction fragment n (42). Fragment 2 is an approximately 1283 base pair EcoRI to PstI restriction sub-fragment of EHV1 BamHI restriction fragment n (42).

HOMOLOGY VECTOR 536-85.30. The plasmid 536-85.30 was constructed for the purpose of deleting the EHV1 glycoprotein G gene. It was used to insert foreign DNA into EHV1. It contains a pair of SalI restriction enzyme sites into which foreign DNA may be inserted. It may be constructed utilizing standard recombinant DNA techniques (23 and 34) by joining restriction fragments from the following sources as indicated in FIG. 6. The plasmid vector is derived from an approximately 2643 base pair EcoRI to PstI restriction fragment of pNEB193 (New England Biolabs). Fragment 1 is an approximately 2292 base pair EcoRI to PvuII restriction sub-fragment of the EHV1 ECORI restriction fragment k (42). Fragment 2 is an approximately 1077 base pair PstI to BamHI restriction sub-fragment of EHV1 EcoRI restriction fragment k (42).

HOMOLOGY VECTOR 495-61.39. The plasmid 495-61.39 was constructed for the purpose of deleting a portion of the EHV-4 thymidine kinase gene. It may also be used to insert foreign DNA into EHV-4. It contains a unique XbaI restriction enzyme site into which foreign DNA may be inserted. It may be constructed utilizing standard recombinant DNA techniques (23, 34) by joining restriction fragments from the following sources with the synthetic DNA sequences indicated in FIG. 7. The plasmid vector is derived from an approximately 2988 base pair SmaI to HincII restriction fragment of pSP65 (Promega). Fragment 1 is an approximately 830 base pair PvuII to FspI restriction sub-fragment of the EHV-4 BamHI restriction fragment c (8). Fragment 2 is an approximately 1220 base pair PvuII to SmaI restriction sub-fragment of EHV-4 BamHI restriction fragment c (8).

HOMOLOGY VECTOR 523-38.9. The plasmid 523-38.9 was constructed for the purpose of deleting a portion of the EHV4 unique short 2 gene. It may also be used to insert foreign DNA into EHV4. It contains a unique PstI restriction enzyme site into which foreign DNA may be inserted. It may be constructed utilizing standard recombinant DNA techniques (23, 34) by joining restriction fragments from the following sources as indicated in FIG. 8. The plasmid vector is derived from an approximately 2984 base pair XbaI to HindIII restriction fragment of pSP65 (Promega). Fragment 1 is an approximately 1098 base pair XbaI to PstI restriction sub-fragment of the EHV4 EcoRI restriction fragment g (8). Fragment 2 is an approximately 2799 base pair PstI to HindIII restriction sub-fragment of EHV4 BamHI restriction fragment d (8).

HOMOLOGY VECTOR 580-57.25. The plasmid 580-57.25 was constructed for the purpose of deleting the EHV4 gpE gene. It may also be used to insert foreign DNA into EHV4. It contains a unique BamHI restriction enzyme site into which foreign DNA may be inserted. It may be constructed utilizing standard recombinant DNA techniques (23, 34), by joining restriction fragments from the following sources as indicated in FIG. 8. The plasmid vector is derived from an approximately 2973 base pair EcoRI to HincII restriction fragment of pSP65 (Promega). Fragment 1 is an approximately 2046 base pair EcoRI to AatII restriction sub-fragment of the EHV4 EcoRI restriction fragment j (8). Fragment 2 is an approximately 1976 base pair FspI to FspI restriction sub-fragment of EHV4 EcoRI restriction fragment j (8).

Figure 10A:
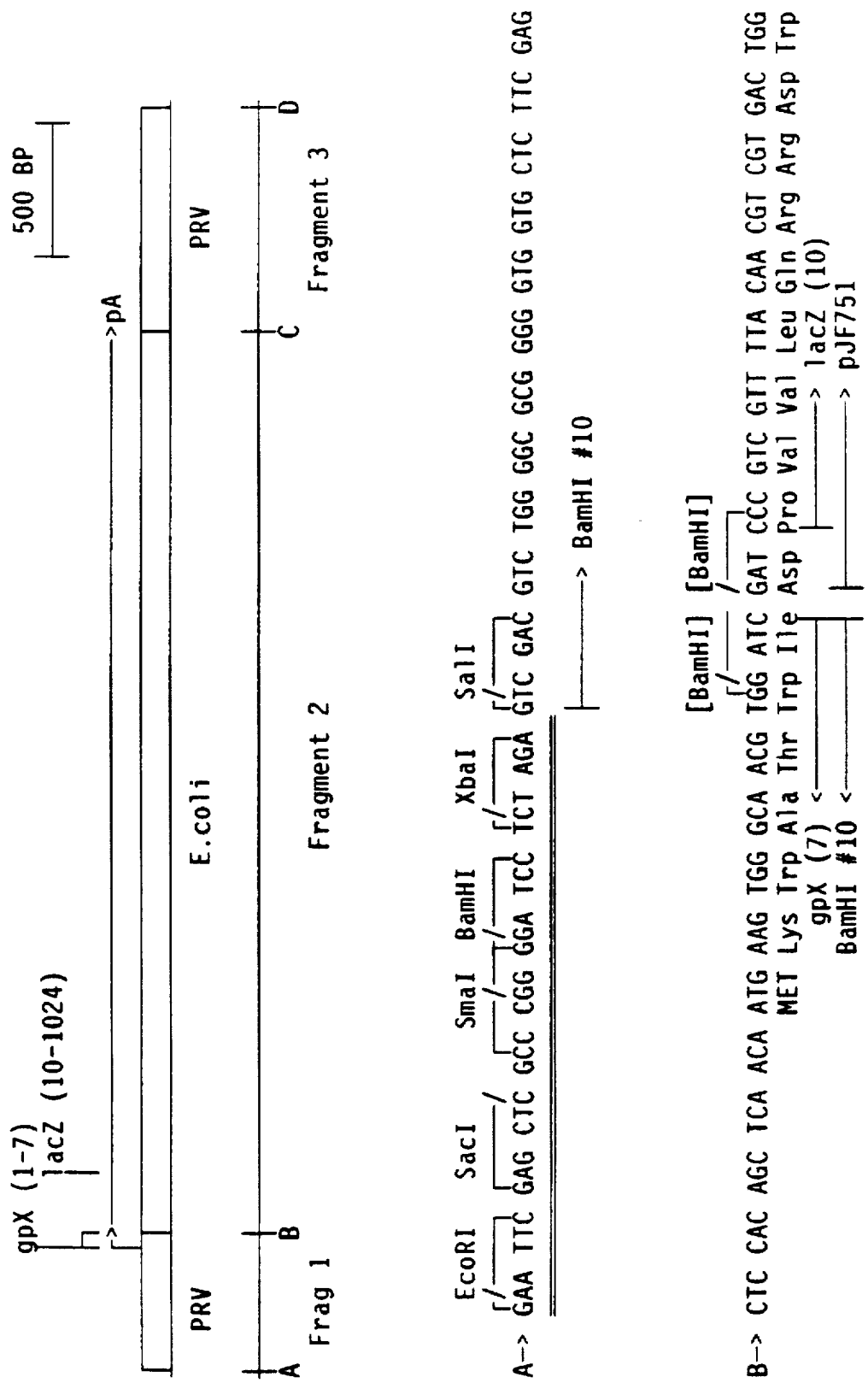
FIGS. 10A and 10B Detailed description of the marker gene insertion in Homology Vector 467-22.A12. The diagram shows the orientation of DNA fragments assembled in the marker gene. The origin of each fragment is described in the Materials and Methods section. The sequences located at the junctions between each fragment and at the ends of the marker gene are shown, including junction A (SEQ ID NO: 40), junction B (SEQ ID NO: 41), junction C (SEQ ID NO: 43) and junction D (SEQ ID NO: 43). The restriction sites used to generate each fragment are indicated at the appropriate junction. The location of the lacZ gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), lactose operon Z gene (lacZ), Escherichia coli (E. coli), poly adenylation signal (pA), and glycoprotein X (gpX).
Figure 10B:
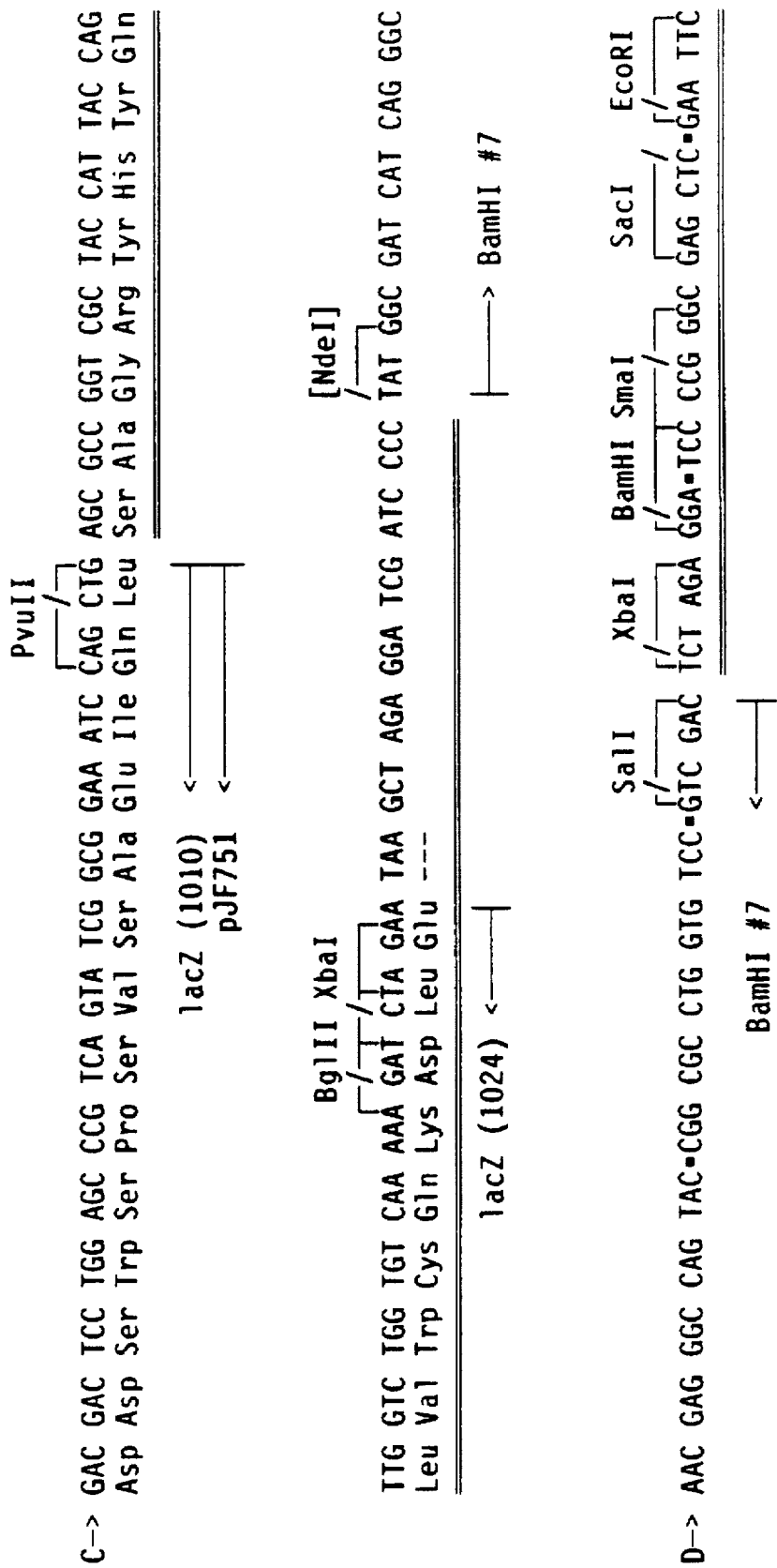

HOMOLOGY VECTOR 467-22.A12. The plasmid 467-22.A12 was constructed for the purpose of deleting a portion of the US2 gene coding region from the EHV-1 virus. It incorporates an E. coli β-galactosidase (lacZ) marker gene flanked by EHV-1 virus DNA. The lacZ marker gene was inserted into the homology vector 467-21.19 at the unique EcoRI site. The barker gene is oriented opposite to the US2 gene in the homology vector. A detailed description of the marker gene is given in FIGS. 10A and 10B. It may be constructed utilizing standard recombinant DNA techniques (23, 34) by joining restriction fragments from the following sources with the synthetic DNA sequences indicated in FIGS. 10A and 10B. Fragment 1 is an approximately 413 base pair SalI to BamHI restriction sub-fragment of the PRV BamHI restriction fragment 10 (22). Fragment 2 is an approximately 3010 base pair BamHI to PvuII restriction fragment of plasmid pJF751 (11). Fragment 3 is an approximately 754 base pair NdeI to SalI restriction sub-fragment of the PRV BamHI restriction fragment #7 (22).

Figure 11A:
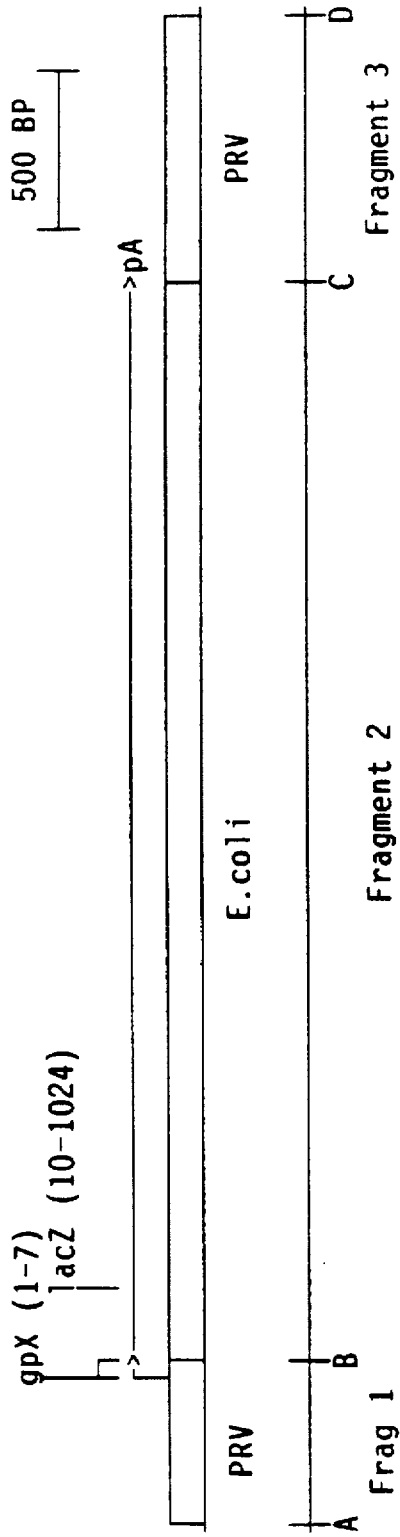
FIGS. 11A and 11B Detailed description of the marker gene insertion in Homology Vector 523-42.A18. The diagram shows the orientation of DNA fragments assembled in the marker gene. The origin of each fragment is described in the Materials and Methods section. The sequences located at the junctions between each fragment and at the ends of the marker gene are shown, including junction A (SEQ ID NO: 46), junction B (SEQ ID NO: 47), junction C (SEQ ID NO: 49), and junction D (SEQ ID NO: 51). The restriction sites used to generate each fragment are indicated at the appropriate junction. The location of the lacZ gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), lactose operon Z gene (lacZ), Escherichia coli (E. coli), poly adenylation signal (pA) and glycoprotein X (gpX).
Figure 11B:
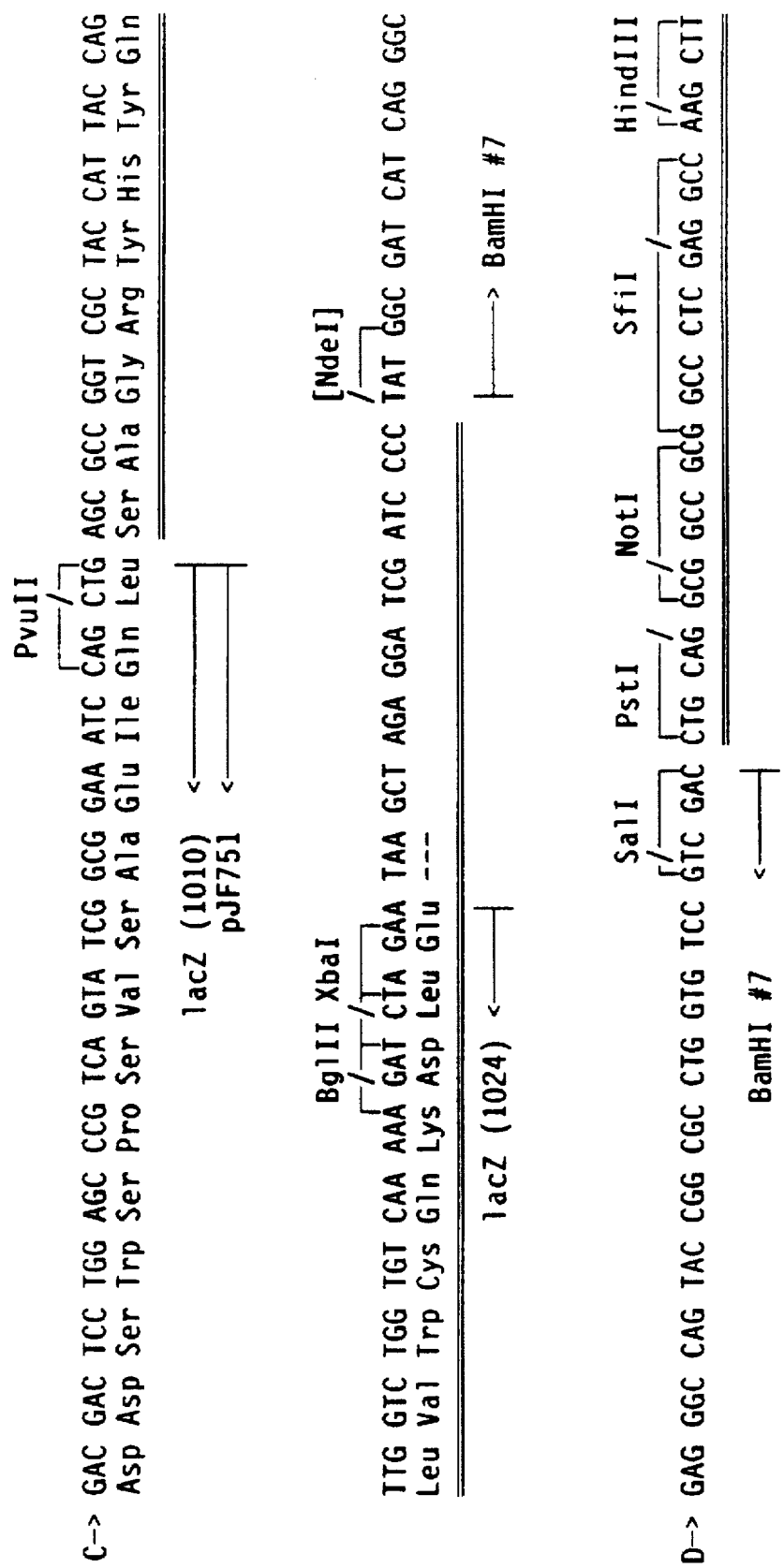

HOMOLOGY VECTOR 523-42.A18. The plasmid 523-42.A18 was constructed for the purpose of deleting a portion of the US2 gene coding region from the EHV-4 virus. It incorporates an E. coli β-galactosidase (lacZ) marker gene flanked by EHV-4 virus DNA. A lacZ marker gene was inserted as a HindIII restriction fragment into the homology vector 523-38.9 at the unique PstI site. The marker gene is oriented in the same direction as the US2 gene in the homology vector. A detailed description of the marker gene is given in FIGS. 11A and 11B. It may be constructed utilizing standard recombinant DNA techniques (23, 34) by joining restriction fragments from the following sources with the synthetic DNA sequences indicated in FIGS. 11a and 11B. Fragment 1 is an approximately 413 base pair SalI to BamHI restriction sub-fragment of the PRV BamHI restriction fragment 10 (22). Fragment 2 is an approximately 3010 base pair BamHI to PvuII restriction fragment of plasmid pJF751 (11). Fragment 3 is an approximately 754 base pair NdeI to SalI restriction sub-fragment of the PRV BamHI restriction fragment #7 (22).

Figure 12A:
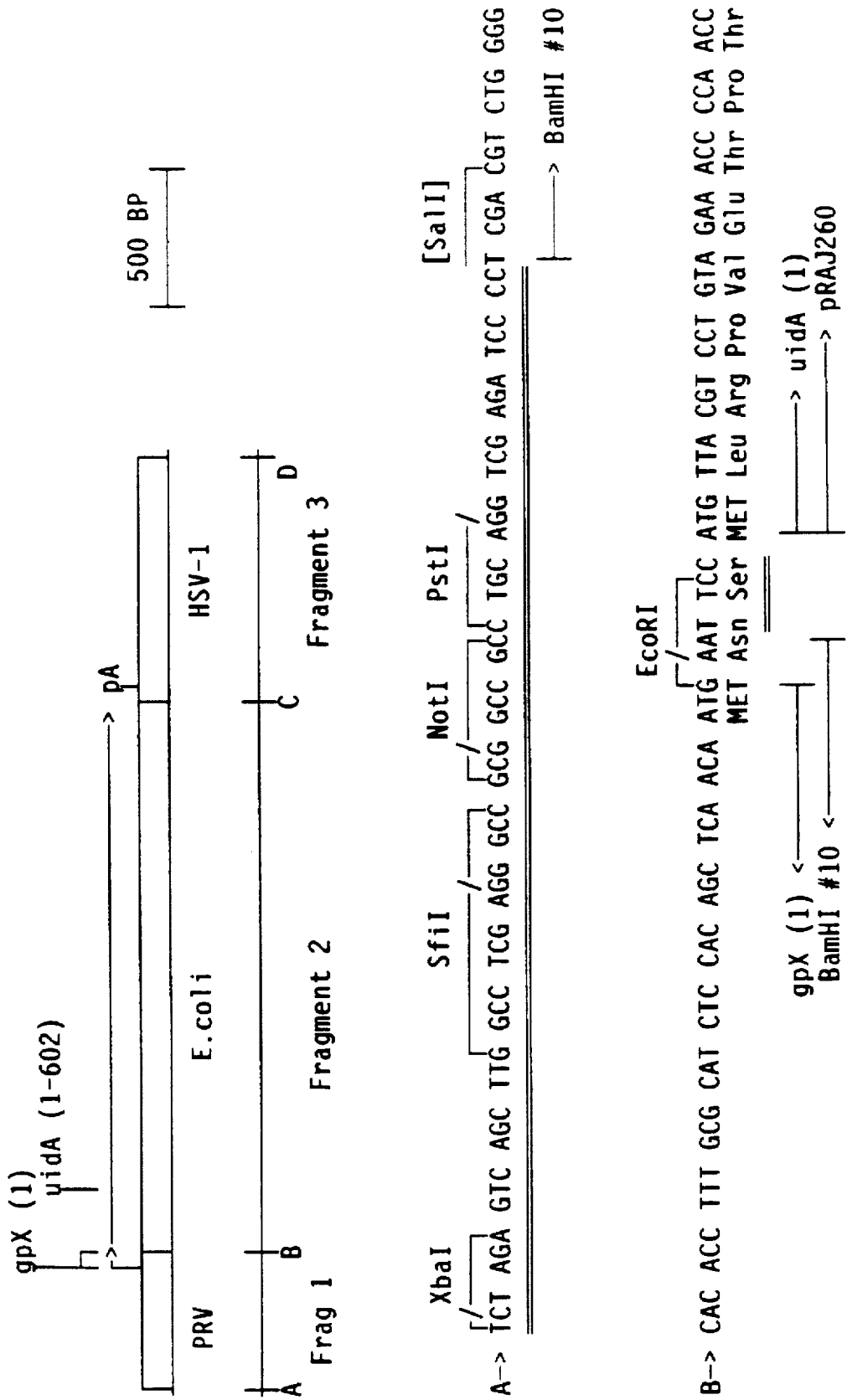
FIGS. 12A and 12B Detailed description of the marker gene insertion in Homology Vector 552-45.19. The diagram shows the orientation of DNA fragments assembled in the marker gene. The origin of each fragment is described in the Materials and Methods section. The sequences located at the junctions between each fragment and at the ends of the marker gene are shown, including junction A (SEQ ID NO: 52), junction B (SEQ ID NO: 53), junction C (SEQ ID NO: 55) and junction D (SEQ ID NO: 57). The restriction sites used to generate each fragment are indicated at the appropriate junction. The location of the lacZ gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), uronidase A gene (uidA), Escherichia coli (E. coli), herpes simplex-virus type 1 (HSV-1), poly adenylation signal (pA), and glycoprotein X (gpX).
Figure 12B:
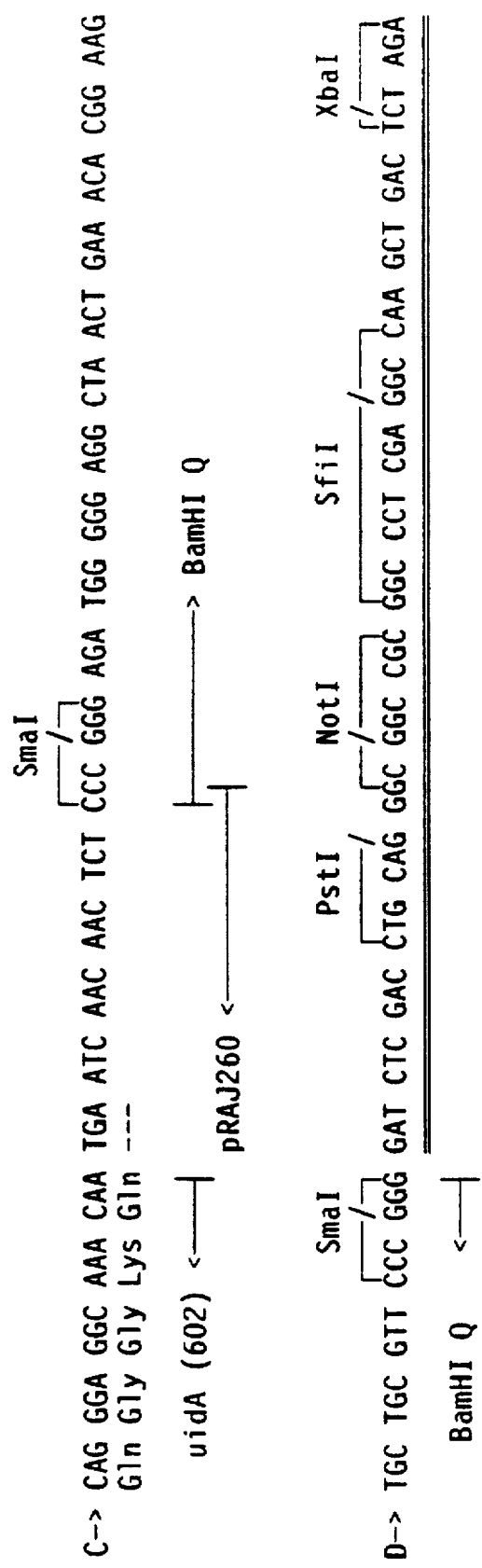

HOMOLOGY VECTOR 552-45.19. The plasmid 552-45.19 was constructed for the purpose of deleting a portion of the TK gene coding region from the EHV-4 virus. It incorporates an E. coli β-glucuronidase (uidA) marker gene flanked by EHV-4 virus DNA. The uidA marker gene was inserted into the homology vector 495-61.39 at the unique XbaI site. The marker gene is oriented opposite to the TK gene in the homology vector. A detailed description of the marker gene is given in FIGS. 12A and 12B. It may be constructed utilizing standard recombinant DNA techniques (23, 34) by joining restriction fragments from the following sources with the synthetic DNA sequences indicated in FIGS. 12A and 12B. Fragment 1 is an approximately 404 base pair SalI to EcoRI restriction sub-fragment of the PRV BamHI restriction fragment #10 (22). Note that the EcoRI site was introduced at the location indicated in FIG. 12 by PCR cloning. Fragment 2 is an approximately 1823 base pair EcoRI to SmaI fragment of the plasmid pRAJ260 (Clonetech). Note that the EcoRI and SmaI sites were introduced at the locations indicated in FIGS. 12A and 12B by PCR cloning. Fragment 3 is an approximately 784 base pair SmaI to SmaI restriction sub-fragment of the HSV-1 BamHI restriction fragment Q (24). Note that this fragment is oriented such that the polyadenylation sequence (AATAAA) is located closest to junction C.

Figure 13A:
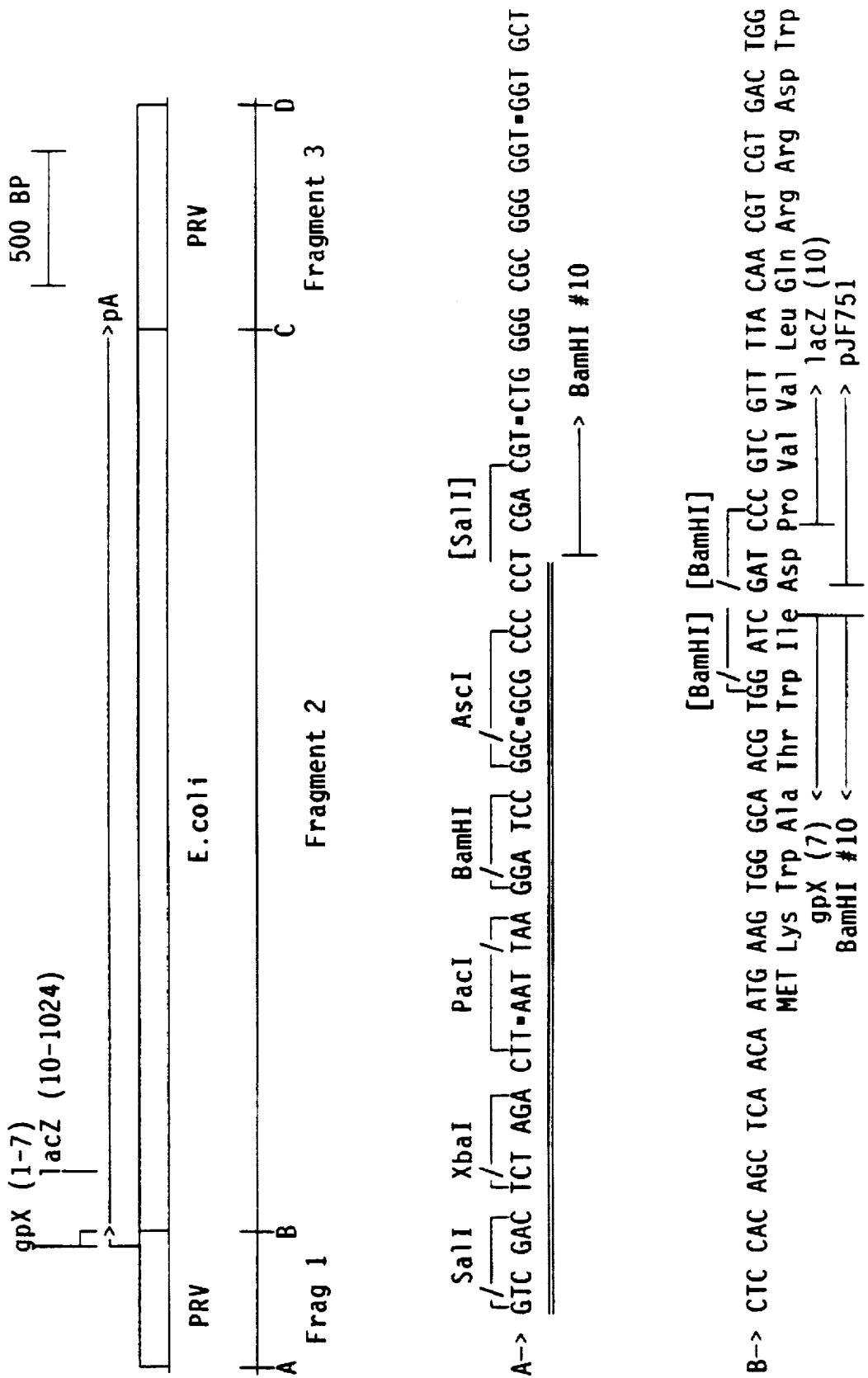
FIGS. 13A and 13B Detailed description of the marker gene insertion in Homology Vector 593-31.2. The diagram shows the orientation of DNA fragments assembled in the marker gene. The origin of each fragment is described in the Materials and Methods section. The sequences located at the junctions between each fragment and at the ends of the marker gene are shown, including junction A (SEQ ID NO: 58), junction B (SEQ ID NO: 59), junction C (SEQ ID NO: 61), and junction D (SEQ ID NO: 63). The restriction sites used to generate each fragment are indicated at the appropriate junction. The location of the lacZ gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), lactose operon Z gene (lacZ), Escherichia coli (E. coli), poly adenylation signal (pA) and glycoprotein X (gpX).
Figure 13B:
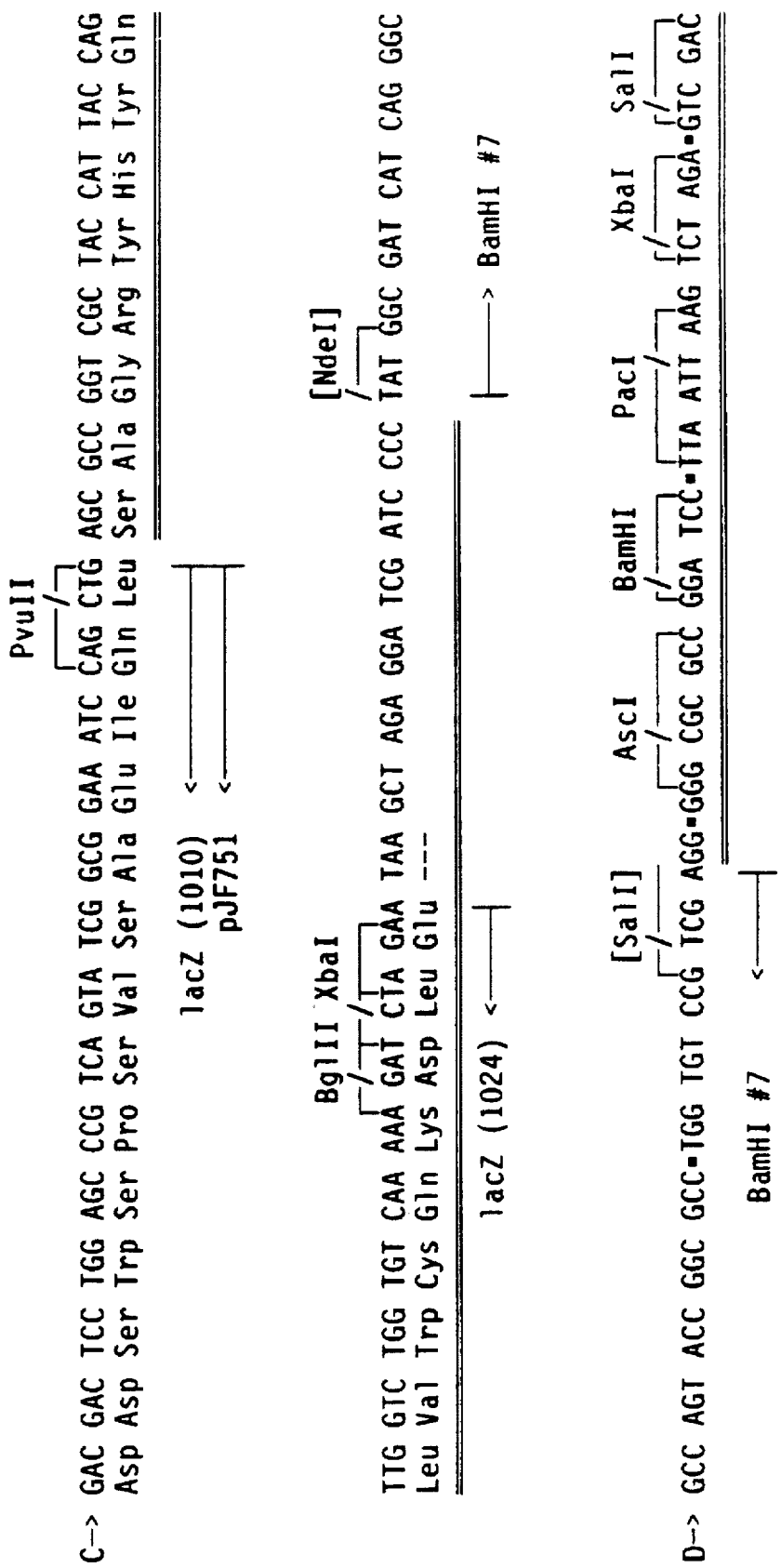

HOMOLOGY VECTOR 593-31.2. The plasmid 593-31.2 was constructed for the purpose of deleting the gpE gene coding region from the EHV-4 virus. It incorporates an E. coli β-galactosidase (lacZ) marker gene flanked by EHV-4 virus DNA. The lacZ marker gene was inserted into the homology vector 580-57.25 at the unique BamHI site. The marker gene is oriented the same as the deleted gpE gene in the homology vector. A detailed description of the marker gene is given in FIGS. 13A and 13B. It may be constructed utilizing standard recombinant DNA techniques (23, 34) by joining restriction fragments from the following sources with the synthetic DNA sequences indicated in FIGS. 10A and 10B. Fragment 1 is an approximately 413 base pair SalI to BamHI restriction sub-fragment of the PRV BamHI restriction fragment 10 (22). Fragment 2 is an approximately 3010 base pair BamHI to PvuII restriction fragment of plasmid pJF751 (11). Fragment 3 is an approximately 754 base pair NdeI to SalI restriction sub-fragment of the PRV BamHI restriction fragment #7 (22).

EXAMPLES

Example 1

UNIQUE SHORT 2 GENE

The deletion of the US2 gene in an Equine herpesvirus renders a recombinant equine herpesvirus safe for use in pregnant equines, that is, it renders the virus incapable of causing abortion of the fetus.

Figures 3A, 3B:
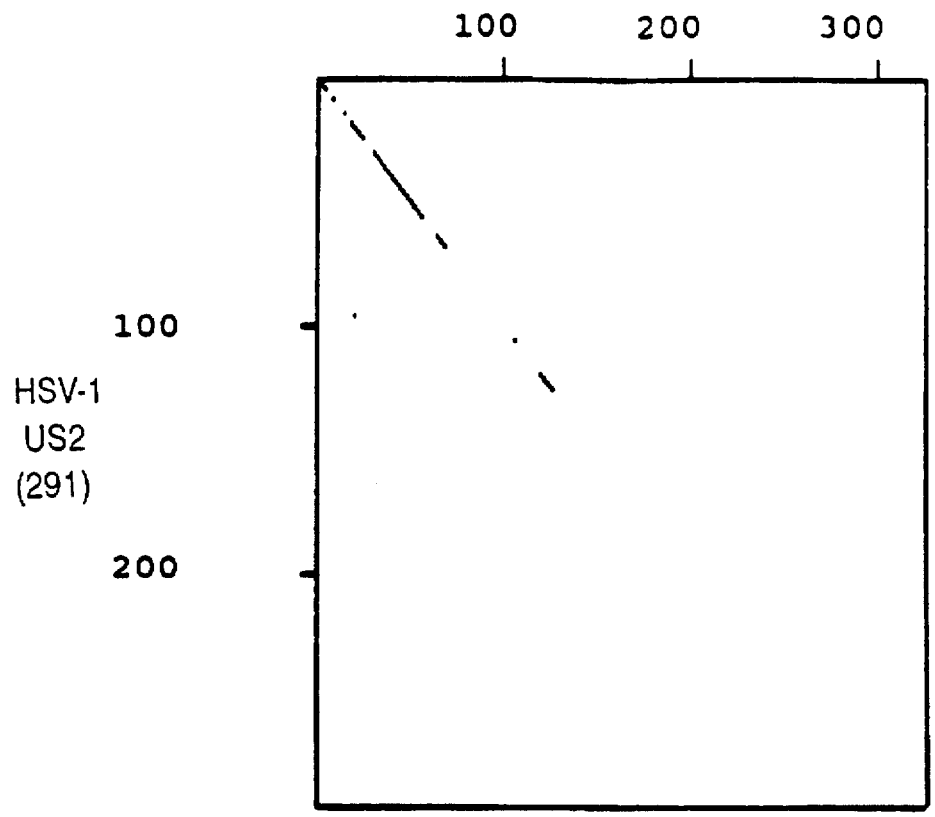
FIGS. 3A and 3B Homology between the equine herpesvirus US2 proteins and the US2 Proteins of HSV-1, PRV, HSV-2, and MDV.
Figure 5:
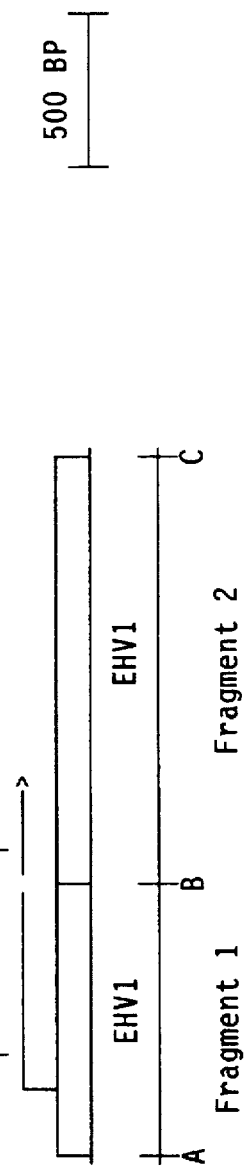
FIG. 5 Detailed description of the DNA insertion in Homology Vector 467-21.19. The diagram shows the orientation of DNA fragments assembled in plasmid 467-21.19. The origin of each fragment is described in the Materials and Methods section. The sequences located at the junctions between each fragment are shown, including junction A (SEQ ID NO: 19), junction B (SEQ ID NO: 20) and junction C (SEQ ID NO: 23). The restriction sites used to generate each fragment are indicated at the appropriate junction. The location of the US2 gene coding region is also given. The following two conventions are used: numbers in parenthesis ( ) refer to amino acids, and restriction sites in brackets [ ] indicate the remnants of sites which were destroyed during construction. The following abbreviations are used, equine herpesvirus 1 (EHV1) and unique short 2 (US2).

We have characterized the unique short regions of EHV-1 and EHV-4 by DNA sequence analysis. SEQ ID NO: 1 shows the sequence of the first 1322 bases of the BamHI fragment n (see FIG. 1) reading away from the BamHI n-BamHI d junction. This sequence contains a 303 amino acid ORF which exhibits homology to several other herpesvirus US2 genes (see FIGS. 3A and 3B). SEQ ID NO: 3 shows the 1252 bases of sequence which starts 198 bases upstream of the HindIII site located approximately in the middle of the EHV-4 EcoRI g fragment (see FIG. 2). The sequence reads back toward the EcoRI g-EcoRI b junction and contains a 324 amino acid ORF. After we sequenced the unique short region, we found that it contained a US2 gene with homology to several other herpesvirus US2 genes (see FIG. 5). Since we determined the location and sequence of the US2 gene in the equine herpes virus, we can delete the US2 gene of EHV-1 and EHV-4 and attenuate as well as render the virus safe for use in pregnant horses.

Example 2

HOMOLOGY VECTOR 450-46.B4

The homology vector 450-46.B4 is a plasmid used for attenuating EHV-1 via inactivation of the TK gene. Inactivation of the TK gene is accomplished by a deletion of DNA which encodes Tk from EHV-1. Plasmid 450-46.B4 carries a copy of the TK gene (31) into which an approximately 202 bp deletion between amino acids 115 and 182 has been introduced. The plasmid, used according to the HOMOLOGOUS RECOMBINATION PROCEDURE FOR GENERATING RECOMBINANT HERPESVIRUS and the SELECTION OF ARA-T RESISTANT VIRUS, generates an EHV-1 containing a deleted TK gene.

Plasmid 450-46.B4 is also useful for inserting foreign DNA into EHV-1. The plasmid contains a unique XbaI restriction site located at the site of the deletion. Foreign DNA cloned into this site results in a plasmid which should be used according to the HOMOLOGOUS RECOMBINATION PROCEDURE FOR GENERATING RECOMBINANT HERPESVIRUS to generate an EHV-1 containing the foreign DNA. Note that if an appropriate marker gene (e.g. *E. coli* lacZ) is inserted into the homology vector, then a recombinant virus is generated without the SELECTION OF ARA-T RESISTANT VIRUS.

For the procedures described above to be successful, it is important that the deletion/insertion site be in a region non-essential to the replication of the EHV-1 and that the site be flanked with equine herpesvirus DNA appropriate for mediating homologous recombination between virus and plasmid DNAs. Note that the deletion was designed so that it is limited to a specific portion of the TK coding region. This region contains amino acids important for TK enzymatic activity. The deletion does not remove sequences that are involved with flanking genes which are important for efficient viral growth (12). We have demonstrated that the insertion/deletion site in homology vector 450-46.B4 inserts foreign DNA into EHV-1 as represented by the two recombinant EHV-1 viruses in EXAMPLES 7 and 9.

Example 3
HOMOLOGY VECTOR 467-21.19

The homology vector 467-21.19 is a plasmid used for attenuating EHV-1 via inactivation of the US2 gene. Inactivation of the US2 gene is accomplished by deletion of US2 encoding DNA from EHV-1. Plasmid 467-21.19 carries a copy of the US2 gene into which an approximately 93 bp deletion between amino acids 174 and 205 has been introduced. The plasmid should be used according to the CONSTRUCTION OF DELETION VIRUSES to generate an EHV-1 containing a deleted US2 gene.

Plasmid 467-21.19 is also useful for the insertion of foreign DNA into EHV-1. The plasmid contains a unique EcoRI restriction site located at the site of the deletion. Foreign DNA cloned into this site results in a plasmid which should be used according to the HOMOLOGOUS RECOMBINATION PROCEDURE FOR GENERATING RECOMBINANT HERPESVIRUS to generate an EHV-1 containing foreign DNA.

For the procedures described above to be successful, it is important that the deletion/insertion site be in a region non-essential to the replication of the EHV-1 and that the site be flanked with equine herpesvirus DNA appropriate for mediating homologous recombination between virus and plasmid DNAs. Note that the deletion was designed so that it is limited to the unique short region and does not remove sequences from the internal or terminal repeats. We have demonstrated that the insertion/deletion site in homology vector 467-21.19 inserts foreign DNA into EHV-1 as represented by the two recombinant EHV-1 viruses in EXAMPLES 7 and 9.

Example 4
HOMOLOGY VECTOR 536-85.30

The homology vector 536-85.30 is a plasmid used for attenuating EHV-1 by removing the glycoprotein G (gpG) gene and a portion of the unique short region large membrane glycoprotein (MGP) gene. Plasmid 536-85.30 carries a portion of the unique short region into which a deletion of approximately 2384 base pairs which removes the entire gpG coding region and the N-terminal 307 amino acids of the MGP has been engineered. The plasmid may be used according to the CONSTRUCTION OF DELETION VIRUSES to generate a gpG/MGP deleted EHV-1.

Plasmid 536-85.30 is also useful for the insertion of foreign DNA into EHV-1. The plasmid contains a pair of SalI restriction sites located at the site of the deletion. Foreign DNA cloned into these sites results in a plasmid which should be used according to the HOMOLOGOUS RECOMBINATION PROCEDURE FOR GENERATING RECOMBINANT HERPESVIRUS to generate an EHV-1 containing foreign DNA.

Example 5
HOMOLOGY VECTOR 495-61.39

The homology vector 495-61.39 is a plasmid used for attenuating EHV-4 via inactivation of the TK gene. Inactivation of the TK gene is accomplished by deletion of DNA which encodes Tk from EHV-4. Plasmid 495-61.39 carries a copy of the TK gene (27) into which an approximately 653 bp deletion between amino acids 98 and 317 has been engineered. The plasmid is used according to the HOMOLOGOUS RECOMBINATION PROCEDURE FOR GENERATING RECOMBINANT HERPESVIRUS and the SELECTION OF ARA-T RESISTANT VIRUS to generate an EHV-4 with a deletion of the gene which encodes Tk.

Plasmid 495-61.39 is also useful for the insertion of foreign DNA into EHV-4. The plasmid contains a unique XbaI restriction site located at the site of the deletion. Foreign DNA cloned into this site results in a plasmid which should be used according to the HOMOLOGOUS RECOMBINATION PROCEDURE FOR GENERATING RECOMBINANT HERPESVIRUS to generate an EHV-4 virus containing foreign DNA. Note that if an appropriate marker gene (e.g. *E. coli* lacZ) is inserted into the homology vector, then a recombinant virus is generated without the SELECTION OF ARA-T RESISTANT VIRUS.

For the procedures described above to be successful, it is important that the deletion/insertion site be in a region non-essential to the replication of the EHV-4 and that the site be flanked with equine herpesvirus DNA appropriate for mediating homologous recombination between virus and plasmid DNAs. Note that the deletion was designed so that it is limited to a specific portion of the TK coding region. This region contains amino acids important for TK enzymatic activity. The deletion does not remove sequences that are involved with flanking genes which are important for efficient viral growth (18, 12).

Example 6
HOMOLOGY VECTOR 523-38.9

The homology vector 523-38.9 is a plasmid used for attenuating EHV-4 via inactivation of the US2 gene. Inactivation of the US2 gene is accomplished by deletion DNA which encodes US2 from EHV-4. Plasmid 523-38.9 carries a copy of the US2 gene into which an approximately 711 bp deletion between amino acids 131 and 324 has been engineered. The plasmid should be used according to the CONSTRUCTION OF DELETION VIRUSES to generate an EHV-4 with a deletion of the gene which encodes US2.

Plasmid 523-38.9 is also useful for the insertion of foreign DNA into EHV-4. The plasmid contains a unique PstI restriction site located at the site of the deletion. Foreign DNA cloned into this site results in a plasmid which should be used according to the HOMOLOGOUS RECOMBINATION PROCEDURE FOR GENERATING RECOMBINANT HERPESVIRUS to generate an EHV-4 containing foreign DNA.

For the procedures described above to be successful, it is important that the deletion/insertion site be in a region non-essential to the replication of the EHV-4 and that the site be flanked with equine herpesvirus DNA appropriate for mediating homologous recombination between virus and plasmid DNAs. Note that the deletion was designed so that it is limited to the unique short region and does not remove sequences from the internal or terminal repeats. We have demonstrated that the insertion/deletion site in homology vector 523-38.9 inserts foreign DNA into EHV-4 as represented by the two recombinant EHV-4 viruses in EXAMPLES 13 and 14.

Example 7
HOMOLOGY VECTOR 580-57.25

We have determined that the deletion of the glycoprotein E gene from the equine herpesvirus is useful in attenuating the virus for use in a vaccine for horses and for providing a negative serological marker.

The homology vector 580-57.25 is a plasmid used to attenuate EHV-4 by removing the glycoprotein E (gpE) gene (8 and SEQ ID NOS: 5 & 6). Plasmid 580-57.25 carries a portion of the unique short region into which a deletion of approximately 1694 base pairs, which removes the entire gpE coding region, has been engineered. The plasmid may be used according to the CONSTRUCTION OF DELETION VIRUSES to generate an EHV-4 virus with a deletion of the gene which encodes gpE.

Plasmid 580-57.25 is also useful for the insertion of foreign DNA into EHV-4. The plasmid contains a unique BamHI restriction site located at the site of the deletion. Foreign DNA cloned into this site results in a plasmid which should be used according to the HOMOLOGOUS RECOMBINATION PROCEDURE FOR GENERATING RECOMBINANT HERPESVIRUS to generate an EHV-4 containing foreign DNA.

Example 8
PREPARATION OF RECOMBINANT EQUINE HERPESVIRUS DESIGNATED S-1EHV-001

S-1EHV-001 is an equine herpesvirus type 1 (EHV-1) virus that has an approximately 202 base pair deletion in the TK gene. The S-1EHV-001 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2357.

S-1EHV-001 was derived from S-1EHV-000 (Dutta strain). This was accomplished utilizing the homology vector 450-46.B4 (see Materials and Methods) and virus S-1EHV-000 in the HOMOLOGOUS RECOMBINATION PROCEDURE FOR GENERATING RECOMBINANT HERPESVIRUS. The transfection stock was selected according to the SELECTION OF ARA-T RESISTANT IBR VIRUS. Individual clones were picked after two rounds of selection and assayed by thymidine plaque autoradiography (37, 38). Plaques picked from TK negative stocks were assayed for TK deletion by the SOUTHERN BLOTTING OF DNA procedure. A plaque which was TK minus by both the thymidine incorporation assay and the southern analysis was chosen and designated S-1EHV-001.

The construction of this virus establishes the EHV-1 thymidine kinase gene as a non-essential gene and a viable site for the insertion of foreign DNA. This virus is useful because the inactivation of the TK gene attenuates the virus.

Example 9
PREPARATION OF RECOMBINANT EQUINE HERPESVIRUS DESIGNATED S-1EHV-002

S-1EHV-002 is an equine herpesvirus type 1 (EHV-1) virus that has two deletions in the short unique region of the genome. The first deletion is approximately 93 base pairs and removes amino acids 174 to 205 of the US2 gene (SEQ ID NO: 1). The second deletion is approximately 2283 base pairs and removes portions of the gpG and MGP genes from the unique short region. The gene for E. coli β-galactosidase (lacZ gene) was inserted into the deletion in the US2 gene and is under the control of the PRV gpX promoter. The S-1EHV-002 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2358.

S-1EHV-002 was derived from S-1EHV-000 (Dutta strain). This was accomplished utilizing the homology vector 467-22.A12 (see Materials and Methods) and virus S-1EHV-000 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The final result of blue plaque purification was the recombinant virus designated S-1EHV-002. This virus was characterized by restriction mapping and the SOUTHERN BLOTTING DNA procedure. This analysis confirmed the insertion of the β-galactosidase (lacZ) marker gene and the deletion of approximately 93 base pairs of the US2 gene. To characterize the second unique short region deletion, the deleted EcoRI k fragment from S-1EHV-002 was subcloned and subjected to DNA sequence analysis. This analysis confirmed a deletion which begins with amino acid 14 of the gpG gene and continues through amino acid 303 of the MGP gene. The deletion occurred such that the remaining 13 amino acids of the gpG gene are in frame with the remaining 494 amino acids of the MGP gene.

The construction of this virus establishes the EHV-1 US2 and gpG genes as non-essential genes and are viable sites for the insertion of foreign DNA. This virus is useful because inactivation of the US2 gene attenuates the virus and the deletion of the glycoprotein G gene from this virus provides a negative serological marker for differentiating it from wild type EHV-1.

Example 10
PREPARATION OF RECOMBINANT EQUINE HERPESVIRUS DESIGNATED S-1EHV-003

S-1EHV-003 is an equine herpesvirus type 1 (EHV-1) virus that has two deletions in the short unique region and one deletion in the unique long region of the genome. The first deletion is an approximately 202 base pair deletion in the TK gene. The second deletion is approximately 93 base pairs and removes nucleic acids 174 to 205 of the US2 gene (SEQ ID NO: 1). The third deletion is approximately 2283 base pairs and removes portions of the gpG and MGP genes from the unique short region. The gene for E. coli β-galactosidase (lacZ gene) was inserted into the deletion in the US2 gene and is under the control of the PRV gpX promoter. The S-1EHV-003 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2359.

S-1EHV-003 was derived from S-1EHV-002 (see EXAMPLE 9). This was accomplished utilizing the homology vector 450-46.B4 (see Materials and Methods) and virus S-1EHV-002 in the HOMOLOGOUS RECOMBINATION PROCEDURE FOR GENERATING RECOMBINANT HERPESVIRUS. The transfection stock was selected according to the SELECTION OF ARA-T RESISTANT IBR VIRUS. Individual clones were picked after two rounds of selection and assayed by thymidine plaque autoradiography (37, 38). Plaques picked from TK negative stocks were assayed for TK deletion by the SOUTHERN BLOTTING OF DNA procedure. A plaque which was TK minus by both the thymidine incorporation assay and the southern analysis was chosen and designated S-1EHV-003.

The construction of this virus establishes that multiple deletions inactivating the TK and US2 genes and removing the gpG genes can be made in a single EHV-1 virus. This virus is useful because the inactivation of the TK and US2 genes attenuates the virus and the deletion of the region which encodes glycoprotein G from this virus provides a negative serological marker for differentiating it from wild type EHV-1.

Example 11
PREPARATION OF RECOMBINANT EQUINE HERPESVIRUS DESIGNATED S-1EHV-004

S-1EHV-004 is an equine herpesvirus type 1 (EHV-1) virus that has one deletion in the long unique region and one deletion in the short unique region of the genome. The first deletion is an approximately 202 base pair deletion in the TK gene. The second deletion is approximately 93 base pairs and removes DNA encoding nucleic acids 174 to 205 of the US2 gene (SEQ ID NO: 1). The gene for *E. coli* β-galactosidase (lacZ gene) was inserted into the deletion in the US2 gene and is under the control of the PRV gpX promoter. The S-1EHV-004 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2360.

S-1EHV-004 was derived from S-1EHV-001 (see EXAMPLE 8). This was accomplished utilizing the homology vector 467-22.A12 (see Materials and Methods) and virus S-1EHV-001 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The final result of blue plaque purification was the recombinant virus designated S-1EHV-004. This virus was characterized by restriction mapping and the SOUTHERN BLOTTING DNA procedure. This analysis confirmed the insertion of the β-galactosidase (lacZ) marker gene, the deletion of approximately 93 base pairs of the US2 gene, and the approximately 202 base pair deletion of the TK gene.

The construction of this virus establishes that the EHV-1 US2 and TK genes are non-essential and are viable sites for the insertion of foreign DNA. This virus is useful because the inactivation of the TK and US2 genes attenuates the virus.

EXAMPLE 12
PREPARATION OF RECOMBINANT EQUINE HERPESVIRUS DESIGNATED S-4EHV-001

S-4EHV-001 is an equine herpesvirus type 4 (EHV-4) virus that has an approximately 202 base pair deletion in the TK gene. The S-4EHV-001 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2361.

S-4EHV-001 was derived from S-4EHV-000 (Dutta strain). This was accomplished utilizing the homology vector 450-46.B4 (see Materials and Methods) and virus S-4EHV-000 in the HOMOLOGOUS RECOMBINATION PROCEDURE FOR GENERATING RECOMBINANT HERPESVIRUS. The transfection stock was selected according to the SELECTION OF ARA-T RESISTANT IBR VIRUS. Individual clones were picked after two rounds of selection and analyzed by the SOUTHERN BLOTTING OF DNA procedure. A plaque which was TK minus by the southern analysis was chosen and designated S-4EHV-001.

The construction of this virus establishes the EHV-4 thymidine kinase gene as a non-essential gene and a viable site for the insertion of foreign DNA. This virus is useful because the inactivation of the TK gene attenuates the virus. The construction of this virus also demonstrates that a homology vector derived from EHV-1 can engineer EHV-4 in an analogous manner.

Example 13
PREPARATION OF RECOMBINANT EQUINE HERPESVIRUS DESIGNATED S-4EHV-002

S-4EHV-002 is an equine herpesvirus type 4 (EHV-4) virus that has one deletion in the long unique region and one deletion in the short unique region of the genome. The first deletion is an approximately 202 base pair deletion in the TK gene. The second deletion is approximately 705 base pairs and removes nucleic acids 131 to 324 of the US2 gene (SEQ ID NO: 3). The gene for *E. coli* β-galactosidase (lacZ gene) was inserted into the deletion in the US2 gene and is under the control of the PRV gpX promoter. The S-4EHV-002 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2362.

S-4EHV-002 was derived from S-4EHV-001 (see EXAMPLE 12). This was accomplished utilizing the homology vector 523-42.A18 (see Materials and Methods) and virus S-4EHV-001 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The final result of blue plaque purification was the recombinant virus designated S-4EHV-002. This virus was characterized by restriction mapping and the SOUTHERN BLOTTING DNA procedure. This analysis confirmed the insertion of the β-galactosidase (lacZ) marker gene, the deletion of approximately 705 base pairs of the US2 gene, and the approximately 202 base pair deletion of the TK gene.

The construction of this virus establishes the EHV-4 US2 and TK genes as non-essential genes and as viable sites for the insertion of foreign DNA. This virus is useful because the inactivation of the TK and US2 genes attenuates the virus.

Example 14
PREPARATION OF RECOMBINANT EQUINE HERPESVIRUS DESIGNATED S-4EHV-003

S-4EHV-003 is an equine herpesvirus type 4 (EHV-4) virus that has one deletion in the short unique region of the genome. The deletion is approximately 705 base pairs and removes nucleic acids 131 to 324 of the US2 gene (SEQ ID NO: 3). The gene for *E. coli* β-galactosidase (lacZ gene) was inserted into the deletion in the US2 gene and is under the control of the PRV gpX promoter. The S-4EHV-003 equine herpesvirus was deposited on Mar. 12, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2363.

S-4EHV-003 was derived from S-4EHV-000 (Dutta strain). This was accomplished utilizing the homology vector 523-42.A18 (see Materials and Methods) and virus S-4EHV-000 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The final result of blue plaque purification was the recombinant virus designated S-4EHV-003. This virus was characterized by restriction mapping and the SOUTHERN BLOTTING DNA procedure. This analysis confirmed the insertion of the β-galactosidase (lacZ) marker gene and the deletion of approximately 705 base pairs of the US2 gene.

The construction of this virus establishes the EHV-4 US2 gene as non-essential and as a viable site for the insertion of foreign DNA. This virus is useful because the inactivation of the US2 gene attenuates the virus.

Example 15
PREPARATION OF RECOMBINANT EQUINE HERPESVIRUS DESIGNATED S-4EHV-004

S-4EHV-004 is an equine herpesvirus type 4 (EHV-4) virus that has a deletion of approximately 653 base pairs between amino acids 98 and 317 of the thymidine kinase gene (28). The gene for E. coli β-glucuronidase (uidA gene) was inserted into the deletion in the TK gene and is under the control of the PRV gpX promoter.

S-4EHV-004 was derived from S-4EHV-000 (Dutta strain). This was accomplished utilizing the homology vector 552-45.19 (see Materials and Methods) and virus S-4EHV-000 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The final result of blue plaque purification was the recombinant virus designated S-4EHV-004. This virus was characterized by restriction mapping and the SOUTHERN BLOTTING DNA procedure. This analysis confirmed the insertion of the β-glucuronidase (uidA) marker gene and the deletion of approximately 653 base pairs of the TK gene.

The construction of this virus establishes that the EHV-4 TK gene is non-essential and is a viable site for the insertion of foreign DNA. This virus is useful because the inactivation of the TK gene attenuates the virus.

Example 16
PREPARATION OF RECOMBINANT EQUINE HERPESVIRUS DESIGNATED S-EHV-010

Recombinant EHV-4 viruses expressing glycoproteins from EHV-1 can be utilized in vaccines to protect against infection by both EHV-1 and EHV-4. Similarly, recombinant EHV-1 viruses expressing EHV-4 glycoproteins can be utilized in vaccines to protect against infection by both EHV-1 and EHV-4.

S-4EHV-010, a recombinant EHV-4 with deletions in the TK, US2, and gpE genes and with the genes for EHV-1 gpD and gpB inserted in place of the TK and gpE genes, respectively, may be constructed in the following manner. S-4EHV-010 would be derived from S-4EHV-004 (see EXAMPLE 15) through the construction of four intermediate viruses. The first intermediate virus, S-4EHV-005, would be constructed similarly to S-4EHV-003, utilizing the homology vector 523-42.A18 (see Materials and Methods) and virus S-4EHV-004 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a blue plaque recombinant virus (lacZ substrate). The resulting virus would have deletions of the TK and US2 genes and insertions of uidA and lacZ in the TK and US2 gene deletions respectively. The second intermediate virus S-4EHV-006, would be constructed, utilizing the homology vector 523-38.9 (see Materials and Methods) and virus S-4EHV-005 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (lacZ substrate). The resulting virus would have deletions of the TK and US2 genes and an insertion of uidA gene in the TK gene deletion. The third intermediate virus, S-4EHV-007, would be constructed, utilizing the homology vector 593-31.2 (see Materials and Methods) and virus S-4EHV-006 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a blue plaque recombinant virus (lacZ substrate). The resulting virus would have deletions of the TK, US2, and gpE genes and insertions of the uidA and lacZ genes in the TK and gpE gene deletions, respectively. The fourth intermediate virus S-4EHV-009, would be constructed, utilizing the homology vector 580-57.25, into which the EHV-1 gpB gene had been inserted, and virus S-4EHV-007 in the HOMOLOGOUS RECOMBINATION PROCEDURE FOR GENERATING RECOMBINANT HERPESVIRUS. Note that the EHV-1 gpB gene would be cloned as an approximately 3665 bp FspI to ClaI sub-fragment of an approximately 5100 bp PstI fragment of EHV-1 (43). The transfection stock would be screened by the SCREEN FOR RECOMBINANT HERPESVIRUS EXPRESSING ENZYMATIC MARKER GENES for a white plaque recombinant virus (lacZ substrate). The resulting virus would have deletions of the TK, US2, and gpE genes and insertion of the uidA and EHV-1 gpB genes in the TK and gpE gene deletions, respectively. Finally, S-4EHV-010 would be constructed, utilizing the homology vector 495-61.39, into which the EHV-1 gpD gene had been inserted, and virus S-4EHV-009 in the HOMOLOGOUS RECOMBINATION PROCEDURE FOR GENERATING RECOMBINANT HERPESVIRUS. Note that the EHV-1 gpD gene would be cloned as an approximately 1929 bp SmaI to EcoRV sub-fragment of the approximately 10,500 bp BamHI D fragment of EHV-1 (1). The transfection stock would be screened by the SCREEN FOR RECOMBINANT HERPESVIRUS EXPRESSING ENZYMATIC MARKER GENES for a white plaque recombinant virus (uidA substrate). This virus can be utilized in a vaccine to protect horses from infection with EHV-1 and EHV-4. The deletion of the glycoprotein E gene from this virus provides a negative serological marker for differentiating it from wild type EHV-1 and EHV-4.

Example 17
PREPARATION OF RECOMBINANT EQUINE HERPESVIRUS DESIGNATED S-EHV-011

Recombinant poxviruses encoding the hemagglutinin (HA) and the neuraminidase genes (NA) from influenza viruses have been reported to mediate protective immunity against infection with the homologous influenza virus (5, 44). Delivery of the HA and NA antigens from several subtypes of equine influenza virus via recombinant EHV viruses can be utilized to provide protective immunity against equine influenza virus in addition to equine herpesvirus.

S-4EHV-011, a recombinant EHV-4 with deletions in the TK, US2, and gpE genes and with the genes for Influenza A/equine/Prague/56 hemagglutinin and neuraminidase of the isolate of equine influenza inserted in place of the gpE gene may be constructed in the following manner. S-4EHV-011 would be derived from S-4EHV-007 (see EXAMPLE 16) through the construction of an intermediate virus. The intermediate virus, S-4EHV-008, would be constructed utilizing the homology vector 495-61.39 (see Materials and Methods) and virus S-4EHV-007 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (uidA substrate). The resulting virus would have deletions in the TK, US2, and gpE genes and an insertion of lacZ in the gpE gene deletion. Finally S-4EHV-011 would be constructed, utilizing the homology vector 580-57.25, into which the hemagglutinin and neuraminidase genes of the Influenza A/equine/Prague/56 isolate of equine influenza had been inserted, and virus S-4EHV-008 in the HOMOLOGOUS RECOMBINATION PROCEDURE FOR GENERATING RECOMBINANT HERPESVIRUS. Note that the influenza virus genes would be cloned using the techniques described in the Materials and Methods section. The hemagglutinin gene would be placed under the control of the HCMV immediate early promoter and the neuraminidase gene would be placed under the control of the PRV gpX promoter. The transfection stock would be screened by the "BLUOGAL" SCREEN FOR RECOMBINANT HERPESVIRUS for a white plaque recombinant virus (lacZ substrate). This virus can be utilized in vaccines to protect horses from infection with EHV-4 and equine influenza virus. An effective vaccine will require antigens from several different influenza strains. This will be accomplished by construction of multiple recombinant viruses expressing HA and NA from several different strains (see EXAMPLES 18–20). A more efficacious vaccine is formulated by mixing this recombinant virus with those described in EXAMPLES 18–20.

Example 18
PREPARATION OF RECOMBINANT EQUINE HERPESVIRUS DESIGNATED S-EHV-012

S-4EHV-012, a recombinant EHV-4 with deletions in the TK, US2, and gpE genes and the genes for hemagglutinin and neuraminidase of the isolate of Influenza A/equine/Miami/63 equine influenza inserted in place of the gpE gene may be constructed in the following manner. S-4EHV-012 would be derived from S-4EHV-007 (see EXAMPLE 16) through the construction of an intermediate virus. The intermediate virus, S-4EHV-008, would be constructed as described in EXAMPLE 17. S-4EHV-011 would be constructed, utilizing the homology vector 580-57.25, into which the hemagglutinin and neuraminidase genes of the Influenza A/equine/Miami/63 isolate of equine influenza had been inserted, and virus S-4EHV-008 in the HOMOLOGOUS RECOMBINATION PROCEDURE FOR GENERATING RECOMBINANT HERPESVIRUS. Note that the influenza virus genes would be cloned using the techniques described in the Materials and Methods section. The hemagglutinin gene would be placed under the control of the HCMV immediate early promoter and the neuraminidase gene would be placed under the control of the PRV gpX promoter. The transfection stock would be screened by the SCREEN FOR RECOMBINANT HERPESVIRUS EXPRESSING ENZYMATIC MARKER GENES for a white plaque recombinant virus (lacZ substrate). This virus can be utilized in a vaccine to protect horses from infection by EHV-4 and equine influenza virus. A more efficacious vaccine is formulated by mixing this recombinant virus with those described here and in EXAMPLES 17, 19 and 20.

Example 19
PREPARATION OF RECOMBINANT EQUINE HERPESVIRUS DESIGNATED S-EHV-013

S-4EHV-013, a recombinant EHV-4 with deletions in the TK, US2, and gpE genes and the genes for hemagglutinin and neuraminidase of the Influenza A/equine/Kentucky/81 isolate of equine influenza inserted in place of the gpE gene may be constructed in the following manner. S-4EHV-013 would be derived from S-4EHV-007 (see EXAMPLE 16) through the construction of an intermediate virus. The intermediate virus, S-4EHV-008, would be constructed as described in EXAMPLE 17. S-4EHV-011 would be constructed, utilizing the homology vector 580-57.25, into which the hemagglutinin and neuraminidase genes of the Influenza A/equine/Kentucky/81 isolate of equine influenza had been inserted, and virus S-4EHV-008 in the HOMOLOGOUS RECOMBINATION PROCEDURE FOR GENERATING RECOMBINANT HERPESVIRUS. Note that the influenza virus genes would be cloned using the techniques described in the Materials and Methods section. The hemagglutinin gene would be placed under the control of the HCMV immediate early promoter and the neuraminidase gene would be placed under the control of the PRV gpX promoter. The transfection stock would be screened by the SCREEN FOR RECOMBINANT HERPESVIRUS EXPRESSING ENZYMATIC MARKER GENES for a white plaque recombinant virus (lacZ substrate). This virus can be utilized in a vaccine to protect horses from infection by EHV-4 and equine influenza virus. A more efficacious vaccine is formulated by mixing this recombinant virus with those described here and in EXAMPLES 17, 18 and 20.

Example 20
PREPARATION OF RECOMBINANT EQUINE HERPESVIRUS DESIGNATED S-EHV-014

S-4EHV-014, a recombinant EHV-4 with deletions in the TK, US2, and gpE genes and the genes for hemagglutinin and neuraminidase of the Influenza A/equine/Alaska/91 isolate of equine influenza inserted in place of the gpE gene may be constructed in the following manner. S-4EHV-014 would be derived from S-4EHV-007 (see EXAMPLE 16) through the construction of an intermediate virus. The intermediate virus, S-4EHV-008, would be constructed as described in EXAMPLE 17. S-4EHV-011 would be constructed, utilizing the homology vector 580-57.25, into which the hemagglutinin and neuraminidase genes of the Influenza A/equine/Alaska/91 isolate of equine influenza had been inserted, and virus S-4EHV-008 in the HOMOLOGOUS RECOMBINATION PROCEDURE FOR GENERATING RECOMBINANT HERPESVIRUS. Note that the influenza virus genes would be cloned using the techniques described in the Materials and Methods section. The hemagglutinin gene would be placed under the control of the HCMV immediate early promoter and the neuraminidase gene would be placed under the control of PRV gpX promoter. The transfection stock would be screened by the "BLUOGAL" SCREEN FOR RECOMBINANT HERPESVIRUS for a white plaque recombinant virus (lacZ substrate). This virus will be useful as a vaccine to protect horses from infection by EHV-4 and equine influenza virus.

A more efficacious vaccine is formulated by mixing this recombinant virus with those described here and in EXAMPLES 17, 18 and 19.

Example 21
VACCINES UTILIZING EHV TO EXPRESS ANTIGENS FROM VARIOUS DISEASE CAUSING MICROORGANISMS
STREPTOCOCCUS EQUI The M protein (14) has been shown to play an important role in the immune response to Streptococcus equi, the causative agent of the severe respiratory disease Strangles. Delivery of this antigen via a recombinant EHV virus would result in strong protective immunity without the post-vaccinal sequelae that often accompany whole culture and protein extracted Streptococcus equi bacterins. It is contemplated that the procedures that have been used to express the marker genes (lacZ and uidA) in S-1EHV-002, S-1EHV-003, S-1EHV-004, S-4EHV-002, S-4EHV-003, and S-4EHV-004 and which are disclosed herein are applicable to the expression of this and other potential Streptococcus equi antigens.

Antigens from the following microorganisms can be utilized to develop equine vaccines: equine infectious anemia virus, equine encephalitis virus, equine rhinovirus and equine rotavirus.

REFERENCES

1. J. Audonnet, et al., Journal of General Virology 71, 2969–2978 (1990).
2. T. Ben-Porat et al., Virology 154, 325–334 (1986).
3. R. A. Bhat, et al., Nucleic Acids Research 17, 1159–1176 (1989)
4. J. L. Cantello, et al., Journal of Virology 65, 1584–1588 (1991).
5. T. M. Chambers, et al., Virology 167, 414–421 (1988).
6. C. F. Colle III, et al., Virology 188, 545–557 (1992).
7. M. L. Cook & J. G. Stevens, Journal of General Virology 31, 75–80 (1976).
8. A. A. Cullinane, et al., Journal of General Virology 69, 1575–1590 (1988).
9. R. C. Desrosiers et al., Molecular and Cellular Biology 5, 2796–2803 (1985).
10. S. J. Edwards, et al., Plasmodium falciparum antigens in recombinant HSV-1, Technological Advances in Vaccine Development, pp. 223–234, Alan Riss, Inc. (1988).
11. F. A. Ferrari, et al., Journal of Bacteriology 161, 556–562 (1985).
12. A. Forrester, et al., Journal of Virology 66, 314–348 (1992).
13. K. Fukuchi et al., Proc. Natl. Acad. Sci. U.S.A. 82, 751–754 (1985).
14. J. E. Galan and J. F. Timoney, Infection and Immunity 55, 3181–3187 (1987).
15. F. L. Grahm and A. Van der Eb., Virolgy 52, 556–567 (1973).
16. R. W. Honess, Journal of General Virology 65, 2077–2107 (1984).
17. D. R. Hustead, Large Animal Veterinarian 46 (2), Mar./Apr., 23–24, (1991).
18. J. G. Jacobson, et al., Journal of Virology 63, 1839–1843, (1089).
19. S. Joshi, et al., Journal of Virology 65, 5524–5530 (1991).
20. Kit et al., Proceedings of the 94th Annual Meeting of the United States Animal Health Association, pp. 66–75 (1990).
21. J. M. Koomey et al., Journal of Virology 50, 662–665 (1984).
22. B. Lomniczi et al., Journal of Virology 49, 970–979 (1984).
23. T. Maniatis, et al., Molecular Cloning: A Laboratory Manual, Cold Spring Harbor, N.Y. (1982).
24. D. J. McGeoch, et al., Journal of Molecular Biology 181, 1–13 (1985).
25. D. J. McGeoch, et al., Journal of General Virology 68, 19–38 (1987).
26. D. J. McGeoch, et al., Journal of General Virology 69, 1531–1574 (1988).
27. L. Nicolson, et al., Journal of General Virology 71, 1801–1805 (1990).
28. L. Nicolson, et al., Virology 179, 378–387 (1990).
29. R. W. Price and A. Kahn, Infection and Immunity, 34, 571–580 (1981).
30. M. P. Riggio, et al., Journal of Virology 63, 1123–1133 (1989).
31. G. R. Robertson and J. M. Whalley, Nucleic Acids Research 6, 11303–11317 (1988).
32. B. Roizman, et al., Cold Spring Harbor Conference on New Approaches to Viral Vaccines (September 1983).
33. B. Roizman, et al., Archives of Virology 123, 425–449 (1992).
34. J. Sambrook, et al., Molecular Cloning: A Laboratory Manual Second Edition, Cold Spring Harbor Press, Cold Spring Harbor, N.Y. (1989).
35. M. Shih, et al., Proceedings of the National Academy of Sciences U.S.A. 81, 5867–5870 (1984).
36. R. R. Spaete and E. S. Mocarski, Proceedings of the National Academy of Sciences U.S.A. 84, 7213–7217 (1987).
37. R. B. Tenser, et al., Journal of General Virology 64, 1369–1373 (1983).
38. R. B. Tenser, et al., Journal of Clinical Microbiology 17, 122–127 (1983).
39. R. L. Thompson et al., Virology 131, 180–192 (1983).
40. D. R. Thomsen, et al., Gene 87, 261–265 (1987).
41. M. Wachsman, et al., Journal of General Virology 70, 2513–2520 (1989).
42. J. M. Whalley, et al., Journal of General Virology 57, 307–323 (1981).
43. J. M. Whalley, et al., Journal of General Virology 70, 383–394 (1989).
44. R. G. Webster, et al., Virology 164, 230–237 (1988).
45. J. P. Weir and P. R. Narayanan, Nucleic Acids Research 16, 10267–10282 (1988).
46. M. E. Whealy, et al., Journal of Virology 62, 4185–4194 (1988).
47. M. A. Wild, et al., 15th International Herpesvirus Workshop, Abstract No. 122, Washington, D.C. (1990).
48. M. Zijil, et al., Journal of Virology 62, 2191–2195 (1988).
49. M. Zijil, et al., Journal of Virology 71, 1747–1755 (1990).
50. F. Zuckerman et al., Vaccination and Control of Aujesky's Disease, pp. 107–117 Ed. J. van Oirschot, Kluwer, London (1989).
51. M. A. Innis, et al., PCR Protocols: A Guide To Methods And Applications, pp. 84–91, Academic Press, Inc., San Diego, Calif. (1990).
52. Katz et al., Journal of Virology, 64, 1808–1811 (1990).

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
( A ) LENGTH: 1322 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Equine herpesvirus 1
( B ) STRAIN: Dutta
( C ) INDIVIDUAL ISOLATE: S-1EHV- 000

( v i i ) IMMEDIATE SOURCE:
( B ) CLONE: 432-54.N17

( v i i i

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| His | Leu | Asn | Ser | Ser | Leu | Ile | Ile | Asn | Gln | Pro | Tyr | His | Leu | Trp | Val |      |
|     |     |     |     | 115 |     |     |     |     | 120 |     |     |     |     | 125 |     |      |
| CTG | GGG | GCA | GCA | GAC | TTG | TGC | AAG | CCG | GTG | TTT | GAC | CTG | ATA | CCC | GGT | 674  |
| Leu | Gly | Ala | Ala | Asp | Leu | Cys | Lys | Pro | Val | Phe | Asp | Leu | Ile | Pro | Gly |      |
|     |     |     | 130 |     |     |     |     | 135 |     |     |     |     | 140 |     |     |      |
| CCT | AAA | CGA | ATG | GTA | TAC | GCA | GAG | ATA | GCA | GAT | GAG | TTT | CAT | AAA | TCT | 722  |
| Pro | Lys | Arg | Met | Val | Tyr | Ala | Glu | Ile | Ala | Asp | Glu | Phe | His | Lys | Ser |      |
|     |     | 145 |     |     |     |     | 150 |     |     |     |     | 155 |     |     |     |      |
| TGG | CAG | CCT | CCC | TTC | GTG | TGT | GGA | AAA | CTG | TTT | GAG | ACA | ATA | CCA | TGG | 770  |
| Trp | Gln | Pro | Pro | Phe | Val | Cys | Gly | Lys | Leu | Phe | Glu | Thr | Ile | Pro | Trp |      |
|     | 160 |     |     |     |     | 165 |     |     |     |     | 170 |     |     |     |     |      |
| ACC | ACC | GTT | GAG | CAT | AAT | CAT | CCG | CTC | AAA | TTA | AGA | GCG | GCG | GGT | GGA | 818  |
| Thr | Thr | Val | Glu | His | Asn | His | Pro | Leu | Lys | Leu | Arg | Ala | Ala | Gly | Gly |      |
| 175 |     |     |     |     | 180 |     |     |     |     | 185 |     |     |     |     | 190 |      |
| GAA | GAC | ACC | GTA | GTG | GGT | GAG | TGT | GGG | TTT | TCC | AAA | CAT | AGC | TCG | AAT | 866  |
| Glu | Asp | Thr | Val | Val | Gly | Glu | Cys | Gly | Phe | Ser | Lys | His | Ser | Ser | Asn |      |
|     |     |     |     | 195 |     |     |     | 200 |     |     |     |     | 205 |     |     |      |
| TCA | TTA | GTT | CGT | CCA | CCC | ACA | GTT | AAG | CGG | GTG | ATT | TAC | GCG | GTG | GTC | 914  |
| Ser | Leu | Val | Arg | Pro | Pro | Thr | Val | Lys | Arg | Val | Ile | Tyr | Ala | Val | Val |      |
|     |     |     | 210 |     |     |     |     | 215 |     |     |     |     | 220 |     |     |      |
| GAC | CCC | GCG | CGC | CTT | CGG | GAA | ATT | CCC | GCC | CCG | GGG | CGG | CCG | CTG | CCG | 962  |
| Asp | Pro | Ala | Arg | Leu | Arg | Glu | Ile | Pro | Ala | Pro | Gly | Arg | Pro | Leu | Pro |      |
|     |     | 225 |     |     |     |     | 230 |     |     |     |     | 235 |     |     |     |      |
| CGG | CGG | CGG | CCG | TCG | GAG | GGG | GGG | ATG | CGC | GCC | CCG | AGG | CGG | CGC | TCG | 1010 |
| Arg | Arg | Arg | Pro | Ser | Glu | Gly | Gly | Met | Arg | Ala | Pro | Arg | Arg | Arg | Ser |      |
|     | 240 |     |     |     |     | 245 |     |     |     |     | 250 |     |     |     |     |      |
| CGC | GCT | CCC | GCG | GCC | GCT | CGG | TCC | ACG | GCC | GCC | GCC | GCG | ACG | CCG | CCC | 1058 |
| Arg | Ala | Pro | Ala | Ala | Ala | Arg | Ser | Thr | Ala | Ala | Ala | Ala | Thr | Pro | Pro |      |
| 255 |     |     |     |     | 260 |     |     |     |     | 265 |     |     |     |     | 270 |      |
| CGC | CCC | GGG | GAC | CCG | CGG | GCG | CCC | GCC | GCC | CGC | CGG | GCG | GGA | GAC | GTG | 1106 |
| Arg | Pro | Gly | Asp | Pro | Arg | Ala | Pro | Ala | Ala | Arg | Arg | Ala | Gly | Asp | Val |      |
|     |     |     |     | 275 |     |     |     |     | 280 |     |     |     |     | 285 |     |      |
| ACG | TGG | ATG | GAA | CGC | CTA | CTC | TGG | GGA | GTG | TTC | GGC | CGG | ACA | TCC | ACA | 1154 |
| Thr | Trp | Met | Glu | Arg | Leu | Leu | Trp | Gly | Val | Phe | Gly | Arg | Thr | Ser | Thr |      |
|     |     |     | 290 |     |     |     |     | 295 |     |     |     |     | 300 |     |     |      |

| CGT | TAAAAGGTAG | GGGACTCTCG | CCAGTACCTC | ACCTCGCTTT | GTGGGTTGAG |      |
|-----|------------|------------|------------|------------|------------|------|
| Arg |            |            |            |            |            | 1207 |

CAGTGGTTTC TTGCCTTGCA AAAGCCTCGC CTTTACACCC ACCACCGCCT AGCCCTGCAC    1267

AACATCCCCT CCATTTTGAA GGGAGAAAAG AGAGAAGACA CCTTTGAAGA TAACA         1322

( 2 ) INFORMATION FOR SEQ ID NO:2:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Gly | Val | Val | Leu | Ile | Thr | Val | Val | Thr | Val | Val | Asp | Arg | His | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Leu | Pro | Asn | Ser | Ser | Ile | Asp | Val | Asp | Gly | His | Leu | Trp | Glu | Phe |
|     |     |     | 20  |     |     |     | 25  |     |     |     | 30  |     |     |     |     |
| Leu | Ser | Arg | Gln | Cys | Phe | Val | Leu | Ala | Ser | Glu | Pro | Leu | Gly | Ile | Pro |
|     |     | 35  |     |     |     | 40  |     |     |     |     | 45  |     |     |     |     |
| Ile | Val | Val | Arg | Ser | Ala | Asp | Leu | Tyr | Arg | Phe | Ser | Ser | Ser | Leu | Leu |
|     | 50  |     |     |     |     | 55  |     |     |     |     | 60  |     |     |     |     |
| Thr | Leu | Pro | Lys | Ala | Cys | Arg | Pro | Ile | Val | Arg | Thr | Arg | Gly | Ala | Thr |
| 65  |     |     |     |     | 70  |     |     |     |     | 75  |     |     |     |     | 80  |

| | | | | | | | | | | | | | |
|---|---|---|---|---|---|---|---|---|---|---|---|---|---|
|Ala|Ile|Ala|Leu|Asp|Arg|Asn|Gly|Val|Val|Tyr|His|Glu|Asp|Arg|Met|
| | | | |85| | | |90| | | | |95| |

Ala Ile Ala Leu Asp Arg Asn Gly Val Val Tyr His Glu Asp Arg Met
                    85                90                    95

Gly Val Ser Ile Glu Trp Leu Ser Val Leu Ser Gly Tyr Asn His Leu
            100                 105                 110

Asn Ser Ser Leu Ile Ile Asn Gln Pro Tyr His Leu Trp Val Leu Gly
            115             120                 125

Ala Ala Asp Leu Cys Lys Pro Val Phe Asp Leu Ile Pro Gly Pro Lys
    130             135                 140

Arg Met Val Tyr Ala Glu Ile Ala Asp Glu Phe His Lys Ser Trp Gln
145                 150             155                         160

Pro Pro Phe Val Cys Gly Lys Leu Phe Glu Thr Ile Pro Trp Thr Thr
                165                 170                 175

Val Glu His Asn His Pro Leu Lys Leu Arg Ala Ala Gly Gly Glu Asp
            180                 185                 190

Thr Val Val Gly Glu Cys Gly Phe Ser Lys His Ser Ser Asn Ser Leu
        195                 200             205

Val Arg Pro Pro Thr Val Lys Arg Val Ile Tyr Ala Val Val Asp Pro
    210             215                 220

Ala Arg Leu Arg Glu Ile Pro Ala Pro Gly Arg Pro Leu Pro Arg Arg
225                 230                 235                     240

Arg Pro Ser Glu Gly Gly Met Arg Ala Pro Arg Arg Arg Ser Arg Ala
            245                     250                 255

Pro Ala Ala Ala Arg Ser Thr Ala Ala Ala Thr Pro Pro Arg Pro
                260             265                 270

Gly Asp Pro Arg Ala Pro Ala Ala Arg Arg Ala Gly Asp Val Thr Trp
        275             280                 285

Met Glu Arg Leu Leu Trp Gly Val Phe Gly Arg Thr Ser Thr Arg
290                 295                 300

( 2 ) INFORMATION FOR SEQ ID NO:3:

( i ) SEQUENCE CHARACTERISTICS:
        ( A ) LENGTH: 1252 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equine herpesvirus 4
        ( B ) STRAIN: Dutta
        ( C ) INDIVIDUAL ISOLATE: S-4EHV- 000

( v i i ) IMMEDIATE SOURCE:
        ( B ) CLONE: 497-52.33 and 488- 18.9

( v i i i ) POSITION IN GENOME:
        ( B ) MAP POSITION: []83
        ( C ) UNITS: %G ( i x ) FEATURE:
        ( A ) NAME/KEY: CDS
        ( B ) LOCATION: 153..1124
        ( D ) OTHER INFORMATION: /codon_start=153
                / product="US2 gene product"

( x i ) SEQUENCE DESCRIPTION: SEQ ID NO:3:

AAGTGTCGAG GTATTTCCAT GCCGATGCTG TGGCTGTGCT ATAAAGCTAC GAATTTCCCG    60

-continued

| | | | | | | | | | | | | |
|---|---|---|---|---|---|---|---|---|---|---|---|---|
| TAACACAGCA | AGTCTTTTTC | ACAACAAAGT | GTGTAGCTAG | AGCAGCTCTG | CTGAAATTTA | | | | | | | 120 |

| | | | | | | | | | | | | | | | |
|---|---|---|---|---|---|---|---|---|---|---|---|---|---|---|---|
| TTGGGTTGGT | TAACACACCC | ATTGCTAATA | AC ATG | GGT | GTG | GTT | TTA | ATT | ACA | | | | | | 173 |
| | | | Met | Gly | Val | Val | Leu | Ile | Thr | | | | | | |
| | | | 1 | | | | 5 | | | | | | | | |

| GTT | GTC | ATG | GTG | GTT | GAC | AGG | CAT | AAA | GCT | TTG | CCC | GAC | AGT | TCT | ATC | 221 |
|---|---|---|---|---|---|---|---|---|---|---|---|---|---|---|---|---|
| Val | Val | Met | Val | Val | Asp | Arg | His | Lys | Ala | Leu | Pro | Asp | Ser | Ser | Ile | |
| | | 10 | | | | | 15 | | | | | 20 | | | | |

| GAC | GTA | GAT | GGA | AAA | CTG | TGG | GAG | TTT | TTG | GGA | CGA | CTA | TGT | TTT | GTA | 269 |
|---|---|---|---|---|---|---|---|---|---|---|---|---|---|---|---|---|
| Asp | Val | Asp | Gly | Lys | Leu | Trp | Glu | Phe | Leu | Gly | Arg | Leu | Cys | Phe | Val | |
| | 25 | | | | 30 | | | | | 35 | | | | | | |

| TTA | GCC | TCA | GAA | CCT | CTA | GGA | ATA | CCA | ATA | GTG | GTG | CGT | TCT | GCT | GAC | 317 |
|---|---|---|---|---|---|---|---|---|---|---|---|---|---|---|---|---|
| Leu | Ala | Ser | Glu | Pro | Leu | Gly | Ile | Pro | Ile | Val | Val | Arg | Ser | Ala | Asp | |
| 40 | | | | | 45 | | | | | 50 | | | | | 55 | |

| CTG | TAC | AAA | TTT | TCT | TCG | AGT | CTC | TTA | GCC | CTG | CCA | AAA | GCA | TGC | AGG | 365 |
|---|---|---|---|---|---|---|---|---|---|---|---|---|---|---|---|---|
| Leu | Tyr | Lys | Phe | Ser | Ser | Ser | Leu | Leu | Ala | Leu | Pro | Lys | Ala | Cys | Arg | |
| | | | | 60 | | | | | 65 | | | | | 70 | | |

| CCT | ATA | GTG | AGA | ACT | AGG | GGG | GCT | ACT | GCT | ATA | GCC | CTA | GAA | AGA | AAT | 413 |
|---|---|---|---|---|---|---|---|---|---|---|---|---|---|---|---|---|
| Pro | Ile | Val | Arg | Thr | Arg | Gly | Ala | Thr | Ala | Ile | Ala | Leu | Glu | Arg | Asn | |
| | | | 75 | | | | | 80 | | | | | 85 | | | |

| GGC | GTG | ATT | TAT | CAA | GAG | GAT | AGA | ATT | GGC | ATT | AGT | ATA | GAG | TGG | CTT | 461 |
|---|---|---|---|---|---|---|---|---|---|---|---|---|---|---|---|---|
| Gly | Val | Ile | Tyr | Gln | Glu | Asp | Arg | Ile | Gly | Ile | Ser | Ile | Glu | Trp | Leu | |
| | | 90 | | | | | 95 | | | | | 100 | | | | |

| TCT | GTA | CTA | TCC | GGC | TAC | AAC | TAC | CTC | AAC | TCC | AGC | ATT | ATC | ATC | AAT | 509 |
|---|---|---|---|---|---|---|---|---|---|---|---|---|---|---|---|---|
| Ser | Val | Leu | Ser | Gly | Tyr | Asn | Tyr | Leu | Asn | Ser | Ser | Ile | Ile | Ile | Asn | |
| | 105 | | | | 110 | | | | | 115 | | | | | | |

| AGG | CCA | TAC | CAC | CTA | TGG | GTT | TTG | GGA | GCT | GCA | GAT | TTA | TGC | AGG | CCT | 557 |
|---|---|---|---|---|---|---|---|---|---|---|---|---|---|---|---|---|
| Arg | Pro | Tyr | His | Leu | Trp | Val | Leu | Gly | Ala | Ala | Asp | Leu | Cys | Arg | Pro | |
| 120 | | | | | 125 | | | | | 130 | | | | | 135 | |

| GTG | TTC | AAC | CTC | ATA | CCG | GGC | CCC | AAG | CGA | ATT | GTG | TAT | GTG | GAG | ATC | 605 |
|---|---|---|---|---|---|---|---|---|---|---|---|---|---|---|---|---|
| Val | Phe | Asn | Leu | Ile | Pro | Gly | Pro | Lys | Arg | Ile | Val | Tyr | Val | Glu | Ile | |
| | | | | 140 | | | | | 145 | | | | | 150 | | |

| GAA | GAT | GAG | TTT | AAT | AAA | TCT | TGG | CAG | CCC | AGC | TTC | GTG | TGC | GGA | AAA | 653 |
|---|---|---|---|---|---|---|---|---|---|---|---|---|---|---|---|---|
| Glu | Asp | Glu | Phe | Asn | Lys | Ser | Trp | Gln | Pro | Ser | Phe | Val | Cys | Gly | Lys | |
| | | | | 155 | | | | | 160 | | | | | 165 | | |

| CTA | TTC | GAA | ACA | ATA | CCG | TTG | ACA | ACC | GTG | GAT | TAT | AAG | CAT | CTA | CTA | 701 |
|---|---|---|---|---|---|---|---|---|---|---|---|---|---|---|---|---|
| Leu | Phe | Glu | Thr | Ile | Pro | Leu | Thr | Thr | Val | Asp | Tyr | Lys | His | Leu | Leu | |
| | | 170 | | | | | 175 | | | | | 180 | | | | |

| AAA | CAA | AAG | GTT | TTA | CCC | GGA | CAA | GAC | CAC | CCT | GAG | AGC | GCG | CGC | AGT | 749 |
|---|---|---|---|---|---|---|---|---|---|---|---|---|---|---|---|---|
| Lys | Gln | Lys | Val | Leu | Pro | Gly | Gln | Asp | His | Pro | Glu | Ser | Ala | Arg | Ser | |
| 185 | | | | | 190 | | | | | 195 | | | | | | |

| TTA | TTA | CAA | CAT | AAA | TCA | TCT | TTT | GTA | TCT | CCC | CCG | CCA | AAT | TTT | AAG | 797 |
|---|---|---|---|---|---|---|---|---|---|---|---|---|---|---|---|---|
| Leu | Leu | Gln | His | Lys | Ser | Ser | Phe | Val | Ser | Pro | Pro | Pro | Asn | Phe | Lys | |
| 200 | | | | | 205 | | | | | 210 | | | | | 215 | |

| CGG | TTA | ATT | TAT | GCG | GTT | GTA | GAC | CCT | ATG | CGT | TTA | CAA | GAG | AAT | TTA | 845 |
|---|---|---|---|---|---|---|---|---|---|---|---|---|---|---|---|---|
| Arg | Leu | Ile | Tyr | Ala | Val | Val | Asp | Pro | Met | Arg | Leu | Gln | Glu | Asn | Leu | |
| | | | | 220 | | | | | 225 | | | | | 230 | | |

| TGT | CCA | CAA | ATA | ACT | AAC | AGA | ACA | AAA | ACT | AAA | AGA | CGT | TCT | AAA | AAA | 893 |
|---|---|---|---|---|---|---|---|---|---|---|---|---|---|---|---|---|
| Cys | Pro | Gln | Ile | Thr | Asn | Arg | Thr | Lys | Thr | Lys | Arg | Arg | Ser | Lys | Lys | |
| | | | 235 | | | | | 240 | | | | | 245 | | | |

| ACT | TAT | AAT | GGC | CTG | TTT | TGC | CAA | GAG | TCT | ACA | GCC | AGC | CTA | AAC | GAT | 941 |
|---|---|---|---|---|---|---|---|---|---|---|---|---|---|---|---|---|
| Thr | Tyr | Asn | Gly | Leu | Phe | Cys | Gln | Glu | Ser | Thr | Ala | Ser | Leu | Asn | Asp | |
| | | 250 | | | | | 255 | | | | | 260 | | | | |

| AAG | ATG | TGT | TTT | ACT | CCA | CAG | CCA | TCA | AAA | GGC | AAA | AAC | TTG | CAG | CGC | 989 |
|---|---|---|---|---|---|---|---|---|---|---|---|---|---|---|---|---|
| Lys | Met | Cys | Phe | Thr | Pro | Gln | Pro | Ser | Lys | Gly | Lys | Asn | Leu | Gln | Arg | |
| 265 | | | | | 270 | | | | | 275 | | | | | | |

| GTT | AGC | ACG | TCG | ATG | CAA | GCC | AAC | TCT | ACA | ATA | CCA | CCT | AGC | ACC | CTA | 1037 |
|---|---|---|---|---|---|---|---|---|---|---|---|---|---|---|---|---|
| Val | Ser | Thr | Ser | Met | Gln | Ala | Asn | Ser | Thr | Ile | Pro | Pro | Ser | Thr | Leu | |
| 280 | | | | 285 | | | | | 290 | | | | | 295 | | |

| TCT | CCT | CGT | GCA | GCT | GCC | CGG | AAA | CCC | ACA | GAA | ATG | ACG | TGG | AAA | TCA | 1085 |
|---|---|---|---|---|---|---|---|---|---|---|---|---|---|---|---|---|
| Ser | Pro | Arg | Ala | Ala | Ala | Arg | Lys | Pro | Thr | Glu | Met | Thr | Trp | Lys | Ser | |

```
                300                      305                      310
CGC CTA CTA GGG GGT GTG TTT GAT AGA ACA GCC AGA CGT TAAAAGGTTG       1134
Arg Leu Leu Gly Gly Val Phe Asp Arg Thr Ala Arg Arg
            315                      320

GGGAAGCTCT TTGCTAGTCA CTGCGCTTTG CCAAGTGTGG TTTCCTGTGA GATTTTTACT   1194

TACAAACTTC ACGTCTATCT TTAGACATGA GCTCCGACAT GCTTACAGCC GCCACTGC    1252
```

( 2 ) INFORMATION FOR SEQ ID NO:4:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Gly Val Val Leu Ile Thr Val Val Met Val Val Asp Arg His Lys
 1               5                  10                      15

Ala Leu Pro Asp Ser Ser Ile Asp Val Asp Gly Lys Leu Trp Glu Phe
            20                  25                  30

Leu Gly Arg Leu Cys Phe Val Leu Ala Ser Glu Pro Gly Ile Pro
            35                  40                  45

Ile Val Val Arg Ser Ala Asp Leu Tyr Lys Phe Ser Ser Leu Leu
    50                  55                  60

Ala Leu Pro Lys Ala Cys Arg Pro Ile Val Arg Thr Arg Gly Ala Thr
65                  70                  75                  80

Ala Ile Ala Leu Glu Arg Asn Gly Val Ile Tyr Gln Glu Asp Arg Ile
            85                  90                  95

Gly Ile Ser Ile Glu Trp Leu Ser Val Leu Ser Gly Tyr Asn Tyr Leu
           100                 105                 110

Asn Ser Ser Ile Ile Ile Asn Arg Pro Tyr His Leu Trp Val Leu Gly
           115                 120                 125

Ala Ala Asp Leu Cys Arg Pro Val Phe Asn Leu Ile Pro Gly Pro Lys
       130                 135                 140

Arg Ile Val Tyr Val Glu Ile Glu Asp Glu Phe Asn Lys Ser Trp Gln
145                 150                 155                 160

Pro Ser Phe Val Cys Gly Lys Leu Phe Glu Thr Ile Pro Leu Thr Thr
                165                 170                 175

Val Asp Tyr Lys His Leu Leu Lys Gln Lys Val Leu Pro Gly Gln Asp
            180                 185                 190

His Pro Glu Ser Ala Arg Ser Leu Leu Gln His Lys Ser Ser Phe Val
        195                 200                 205

Ser Pro Pro Pro Asn Phe Lys Arg Leu Ile Tyr Ala Val Val Asp Pro
    210                 215                 220

Met Arg Leu Gln Glu Asn Leu Cys Pro Gln Ile Thr Asn Arg Thr Lys
225                 230                 235                 240

Thr Lys Arg Arg Ser Lys Lys Thr Tyr Asn Gly Leu Phe Cys Gln Glu
                245                 250                 255

Ser Thr Ala Ser Leu Asn Asp Lys Met Cys Phe Thr Pro Gln Pro Ser
            260                 265                 270

Lys Gly Lys Asn Leu Gln Arg Val Ser Thr Ser Met Gln Ala Asn Ser
        275                 280                 285

Thr Ile Pro Pro Ser Thr Leu Ser Pro Arg Ala Ala Ala Arg Lys Pro
    290                 295                 300

Thr Glu Met Thr Trp Lys Ser Arg Leu Leu Gly Gly Val Phe Asp Arg
```

305            310            315            320

Thr Ala Arg Arg ( 2 ) INFORMATION FOR SEQ ID NO:5:

( i ) SEQUENCE CHARACTERISTICS:
        ( A ) LENGTH: 1149 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equine herpesvirus 4
        ( B ) STRAIN: Dutta
        ( C ) INDIVIDUAL ISOLATE: S-4EHV- 000

( v i i ) IMMEDIATE SOURCE:
        ( B ) CLONE: 467-42.A12

( v i i i ) POSITION IN GENOME:
        ( B ) MAP POSITION: []89
        ( C ) UNITS: %G ( i x ) FEATURE:
        ( A ) NAME/KEY: CDS
        ( B ) LOCATION: 271..1149
        ( D ) OTHER INFORMATION: /partial
            / codon_start=271
            / function="membrane glycoprotein"
            / product="Glycoprotein E N-terminus"
            / gene="gpE"

( x i ) SEQUENCE DESCRIPTION: SEQ ID NO:5:

```
TCTAGAACAG  TTGAACCGTA  AACTGGAGGC  CATAAAAGAG  GAAGACTAAT  AATGGGGGGT      60

TTTTAAAGTT  TATGTATTAT  TGTTTCTATA  TATTAAAAAT  TGTTGAAATA  TAAATATCTT     120

ATGTAATGTT  TACATTATTC  GTGATTGGGA  CGGTCTTAGG  GGAGGTGGTG  CAACTAGGGT     180

TTAAAGCCCT  GAATGTTCTG  GAGTGAACCC  ACAGTTCTCC  TCTTTGGGCG  TCAAAGCAAT     240

CAGACGTCCA  ATCTAAAGTA  GAACGTCACA  ATG GAG CTG TTA GAC TCC CGC CGT       294
                                    Met Glu Leu Leu Asp Ser Arg Arg
                                     1               5

GCT TTT TTC TTT TTT GTA CTA ATA ACA GTA CTC GAT GCG TGG GGA GTT           342
Ala Phe Phe Phe Phe Val Leu Ile Thr Val Leu Asp Ala Trp Gly Val
     10              15                  20

CAA CGG GTT GAA CTC ACC GAG GGG GCA TGG GCC ATG ATC GAC GGA AGA           390
Gln Arg Val Glu Leu Thr Glu Gly Ala Trp Ala Met Ile Asp Gly Arg
 25              30                  35                  40

GAC GTT TTA ACC CCA ACT AAC ACG ACC ACT AGG GTT ACA AAG GCC TGG           438
Asp Val Leu Thr Pro Thr Asn Thr Thr Thr Arg Val Thr Lys Ala Trp
             45                  50                  55

ACA TTT TTG GAA ACC CCA CCG GGA TGT GCT GGT GAT ATA ACA GTC AAG           486
Thr Phe Leu Glu Thr Pro Pro Gly Cys Ala Gly Asp Ile Thr Val Lys
         60                  65                  70

ACT GTG TGC GTA CAA GCT AGT CTG TGC GAA GAT AAC ATT ATA ATA GGA           534
Thr Val Cys Val Gln Ala Ser Leu Cys Glu Asp Asn Ile Ile Ile Gly
     75                  80                  85

AAT CAC TGT AAC CTA CTA ACC GGG GAG CAT GGC ATT GCG CTT GCA GAG           582
Asn His Cys Asn Leu Leu Thr Gly Glu His Gly Ile Ala Leu Ala Glu
     90                  95                  100

TTT AAC GTA GTT AAC GGA TCG CTA CAA AGG ACC AAA GAT GTG TAC TTT           630
Phe Asn Val Val Asn Gly Ser Leu Gln Arg Thr Lys Asp Val Tyr Phe
```

-continued

| | | | | | | | | | | | | | | | | |
|---|---|---|---|---|---|---|---|---|---|---|---|---|---|---|---|---|
| 105 | | | | | 110 | | | | | 115 | | | | | 120 | |
| GTT | AAT | GGA | ACA | GTT | TTT | CCT | ATT | CTG | GCA | GAA | ACC | CGC | AGC | GTG | TTA | 678 |
| Val | Asn | Gly | Thr | Val | Phe | Pro | Ile | Leu | Ala | Glu | Thr | Arg | Ser | Val | Leu | |
| | | | | 125 | | | | | 130 | | | | | 135 | | |
| CAA | ATT | CAG | AGG | GCA | ACC | CCA | TCC | ATA | GCT | GGA | GTT | TAT | ACT | CTT | CAT | 726 |
| Gln | Ile | Gln | Arg | Ala | Thr | Pro | Ser | Ile | Ala | Gly | Val | Tyr | Thr | Leu | His | |
| | | | 140 | | | | | 145 | | | | | 150 | | | |
| GTT | TCC | ATA | AAC | GGA | CAC | ATA | AAA | CAC | TCT | GTT | GTG | TTG | CTC | ACC | GTA | 774 |
| Val | Ser | Ile | Asn | Gly | His | Ile | Lys | His | Ser | Val | Val | Leu | Leu | Thr | Val | |
| | | 155 | | | | | 160 | | | | | 165 | | | | |
| AAG | AAA | CCA | CCA | ACA | CGC | GTA | CAT | GTC | AAG | ACG | CCT | CCA | CCC | ATA | CTA | 822 |
| Lys | Lys | Pro | Pro | Thr | Arg | Val | His | Val | Lys | Thr | Pro | Pro | Pro | Ile | Leu | |
| | 170 | | | | | 175 | | | | | 180 | | | | | |
| GTT | CCC | CAG | GTT | ACA | CCA | GAG | GCA | CAT | ACA | GAT | TTC | ATA | GTG | CGC | GGA | 870 |
| Val | Pro | Gln | Val | Thr | Pro | Glu | Ala | His | Thr | Asp | Phe | Ile | Val | Arg | Gly | |
| 185 | | | | | 190 | | | | | 195 | | | | | 200 | |
| TAC | CAC | TCG | CGC | GTA | TAT | GCT | GTG | GGT | GAG | TCC | TTT | GAC | CTG | TCT | GTG | 918 |
| Tyr | His | Ser | Arg | Val | Tyr | Ala | Val | Gly | Glu | Ser | Phe | Asp | Leu | Ser | Val | |
| | | | | 205 | | | | | 210 | | | | | 215 | | |
| CAC | CTA | GAA | TCC | CAC | ATA | CAG | GAG | TCT | AGC | TTT | AAC | GCT | GAA | ATC | CAA | 966 |
| His | Leu | Glu | Ser | His | Ile | Gln | Glu | Ser | Ser | Phe | Asn | Ala | Glu | Ile | Gln | |
| | | | 220 | | | | | 225 | | | | | 230 | | | |
| TGG | TAT | TAT | ATG | AAT | ACG | TCA | TCG | TCA | TCA | TGC | GAT | TTG | TTT | CGA | GTT | 1014 |
| Trp | Tyr | Tyr | Met | Asn | Thr | Ser | Ser | Ser | Ser | Cys | Asp | Leu | Phe | Arg | Val | |
| | | 235 | | | | | 240 | | | | | 245 | | | | |
| TTT | GAA | ACA | TGC | ATT | TTT | CAC | CCA | ACC | GCT | ATG | GCC | TGC | CTG | CAC | CCC | 1062 |
| Phe | Glu | Thr | Cys | Ile | Phe | His | Pro | Thr | Ala | Met | Ala | Cys | Leu | His | Pro | |
| | 250 | | | | | 255 | | | | | 260 | | | | | |
| GAA | CAA | CAC | GCC | TGC | TGC | TTT | ACA | TCT | CCC | GTC | AGG | GCT | ACG | AAG | ATT | 1110 |
| Glu | Gln | His | Ala | Cys | Cys | Phe | Thr | Ser | Pro | Val | Arg | Ala | Thr | Lys | Ile | |
| 265 | | | | 270 | | | | | 275 | | | | | 280 | | |
| CTT | CAT | CGA | GTA | TAT | GGT | AAC | TGC | AGC | AAT | CGT | GGA | TCC | | | | 1149 |
| Leu | His | Arg | Val | Tyr | Gly | Asn | Cys | Ser | Asn | Arg | Gly | Ser | | | | |
| | | | | 285 | | | | | 290 | | | | | | | |

( 2 ) INFORMATION FOR SEQ ID NO:6:

( i ) SEQUENCE CHARACTERISTICS:
        ( A ) LENGTH: 293 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Glu | Leu | Leu | Asp | Ser | Arg | Arg | Ala | Phe | Phe | Phe | Val | Leu | Ile |
| 1 | | | | 5 | | | | | 10 | | | | | 15 |
| Thr | Val | Leu | Asp | Ala | Trp | Gly | Val | Gln | Arg | Val | Glu | Leu | Thr | Glu | Gly |
| | | | 20 | | | | | 25 | | | | | 30 | | |
| Ala | Trp | Ala | Met | Ile | Asp | Gly | Arg | Asp | Val | Leu | Thr | Pro | Thr | Asn | Thr |
| | | 35 | | | | | 40 | | | | | 45 | | | |
| Thr | Thr | Arg | Val | Thr | Lys | Ala | Trp | Thr | Phe | Leu | Glu | Thr | Pro | Pro | Gly |
| | 50 | | | | | 55 | | | | | 60 | | | | |
| Cys | Ala | Gly | Asp | Ile | Thr | Val | Lys | Thr | Val | Cys | Val | Gln | Ala | Ser | Leu |
| 65 | | | | | 70 | | | | | 75 | | | | | 80 |
| Cys | Glu | Asp | Asn | Ile | Ile | Ile | Gly | Asn | His | Cys | Asn | Leu | Leu | Thr | Gly |
| | | | | 85 | | | | | 90 | | | | | 95 | |
| Glu | His | Gly | Ile | Ala | Leu | Ala | Glu | Phe | Asn | Val | Val | Asn | Gly | Ser | Leu |
| | | | 100 | | | | | 105 | | | | | 110 | | |
| Gln | Arg | Thr | Lys | Asp | Val | Tyr | Phe | Val | Asn | Gly | Thr | Val | Phe | Pro | Ile |

|   |   |   |   |   | 115 |   |   |   | 120 |   |   |   | 125 |   |   |   |
|---|---|---|---|---|---|---|---|---|---|---|---|---|---|---|---|---|

Leu Ala Glu Thr Arg Ser Val Leu Gln Ile Gln Arg Ala Thr Pro Ser
130                 135             140

Ile Ala Gly Val Tyr Thr Leu His Val Ser Ile Asn Gly His Ile Lys
145             150             155             160

His Ser Val Val Leu Leu Thr Val Lys Lys Pro Pro Thr Arg Val His
                165             170                 175

Val Lys Thr Pro Pro Pro Ile Leu Val Pro Gln Val Thr Pro Glu Ala
            180             185             190

His Thr Asp Phe Ile Val Arg Gly Tyr His Ser Arg Val Tyr Ala Val
        195             200             205

Gly Glu Ser Phe Asp Leu Ser Val His Leu Glu Ser His Ile Gln Glu
    210             215             220

Ser Ser Phe Asn Ala Glu Ile Gln Trp Tyr Tyr Met Asn Thr Ser Ser
225             230             235             240

Ser Ser Cys Asp Leu Phe Arg Val Phe Glu Thr Cys Ile Phe His Pro
            245             250             255

Thr Ala Met Ala Cys Leu His Pro Glu Gln His Ala Cys Cys Phe Thr
        260             265             270

Ser Pro Val Arg Ala Thr Lys Ile Leu His Arg Val Tyr Gly Asn Cys
    275             280             285

Ser Asn Arg Gly Ser
290

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Equine herpesvirus 1
        (B) STRAIN: Dutta
        (C) INDIVIDUAL ISOLATE: S-1EHV-000

(viii) POSITION IN GENOME:
    &nb (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Equine herpesvirus 4
    (B) STRAIN: Dutta
    (C) INDIVIDUAL ISOLATE: S-4EHV- 000

(v i i i) POSITION IN GENOME:
    (B) MAP POSITION: []83
    (C) UNITS: %G (i x) FEATURE:
    (A) NAME/KEY: Region
    (B) LOCATION: 1..18
    (D) OTHER INFORMATION: /label=EHV4-US2
        / note="Conserved region of US2 gene starting at
        amino acid 123."

(x i) SEQUENCE DESCRIPTION: SEQ ID NO:8:

His Leu Trp Val Leu Gly Ala Ala Asp Leu Cys Arg Pro Val Phe Asn
1               5                   10                  15

Leu Ile (2) INFORMATION FOR SEQ ID NO:9:

( i v ) ANTI-SENSE: NO ( v i ) ORIGINAL SOURCE:
    ( A ) ORGANISM: Herpes simplex virus 2
    ( B ) STRAIN: HG52

( v i i i ) POSITION IN GENOME:
    ( B ) MAP POSITION: []88
    ( C ) UNITS: %G ( i x ) FEATURE:
    ( A ) NAME/KEY: Region
    ( B ) LOCATION: 1..18
    ( D ) OTHER INFORMATION: /label=HSV2-US2
        / note="Conserved region of US2 gene starting at
        amino acid 123."

( x i ) SEQUENCE DESCRIPTION: SEQ ID NO:10:

```
His Leu Trp Val Val Gly Ala Ala Asp Leu Cys Val Pro Phe Phe Glu
1               5                   10                  15

Tyr Ala
```

( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudorabies virus
        ( B ) STRAIN: NIA-3

( v i i i ) POSITION IN GENOME:
        ( B ) MAP POSITION: []90
        ( C ) UNITS: %G ( i x ) FEATURE:
        ( A ) NAME/KEY: Region
        ( B ) LOCATION: 1..18
        ( D ) OTHER INFORMATION: /label=PRV-US2
            / note="Conserved region of US2 gene starting at
            amino acid 148."

( x i ) SEQUENCE DESCRIPTION: SEQ ID NO:11:

```
His Leu Trp Ile Leu Gly Ala Ala Asp Leu Cys Asp Gln Val Leu Leu
1               5                   10                  15

Ala Ala
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Marek's disease gammaherpesvirus
        ( B ) STRAIN: RB1B (viii) POSITION IN GENOME:
  (B) MAP POSITION: []88
  (C) UNITS: %G (ix) FEATURE:
  (A) NAME/KEY: Region
  (B) LOCATION: 1..19
  (D) OTHER INFORMATION: /label=MDV-US2
      / note="Conserved region of US2 gene starting at amino acid 132."

(xi) SEQUENCE DESCRIPTION: SEQ ID NO:12:

His Ser Leu Trp Ile Val Gly Ala Ala Asp Ile Cys Arg Ile Ala Leu
1               5                   10                  15

Glu Cys Ile (2) INFORMATION FOR SEQ ID NO:13:

(i) SEQUENCE CHARACTERISTICS:
    (A) LENGTH: 18 amino acids
    (B) TYPE: amino acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Bovine herpesvirus 1
    (B) STRAIN: Cooper
    (C) INDIVIDUAL ISOLATE: S-IBR- 000

(viii) POSITION IN GENOME:
    (B) MAP POSITION: []85
    (C) UNITS: %G (ix) FEATURE:
    (A) NAME/KEY: Region
    (B) LOCATION: 1..18
    (D) OTHER INFORMATION: /label=IBR-US2
        / note="Conserved region of US2 gene starting at amino acid 115."

(xi) SEQUENCE DESCRIPTION: SEQ ID NO:13:

His Met Trp Val Phe Gly Ala Ala Asp Leu Tyr Ala Pro Ile Phe Ala
1               5                   10                  15

His Ile (2) INFORMATION FOR SEQ ID NO:14:

(i) SEQUENCE CHARACTERISTICS:
    (A) LENGTH: 66 base pairs
    (B) TYPE: nucleic acid
    (C) STRANDEDNESS: double
    (D) TOPOLOGY: circular (ii) MOLECULE TYPE: DNA (genomic)

Figure 4:
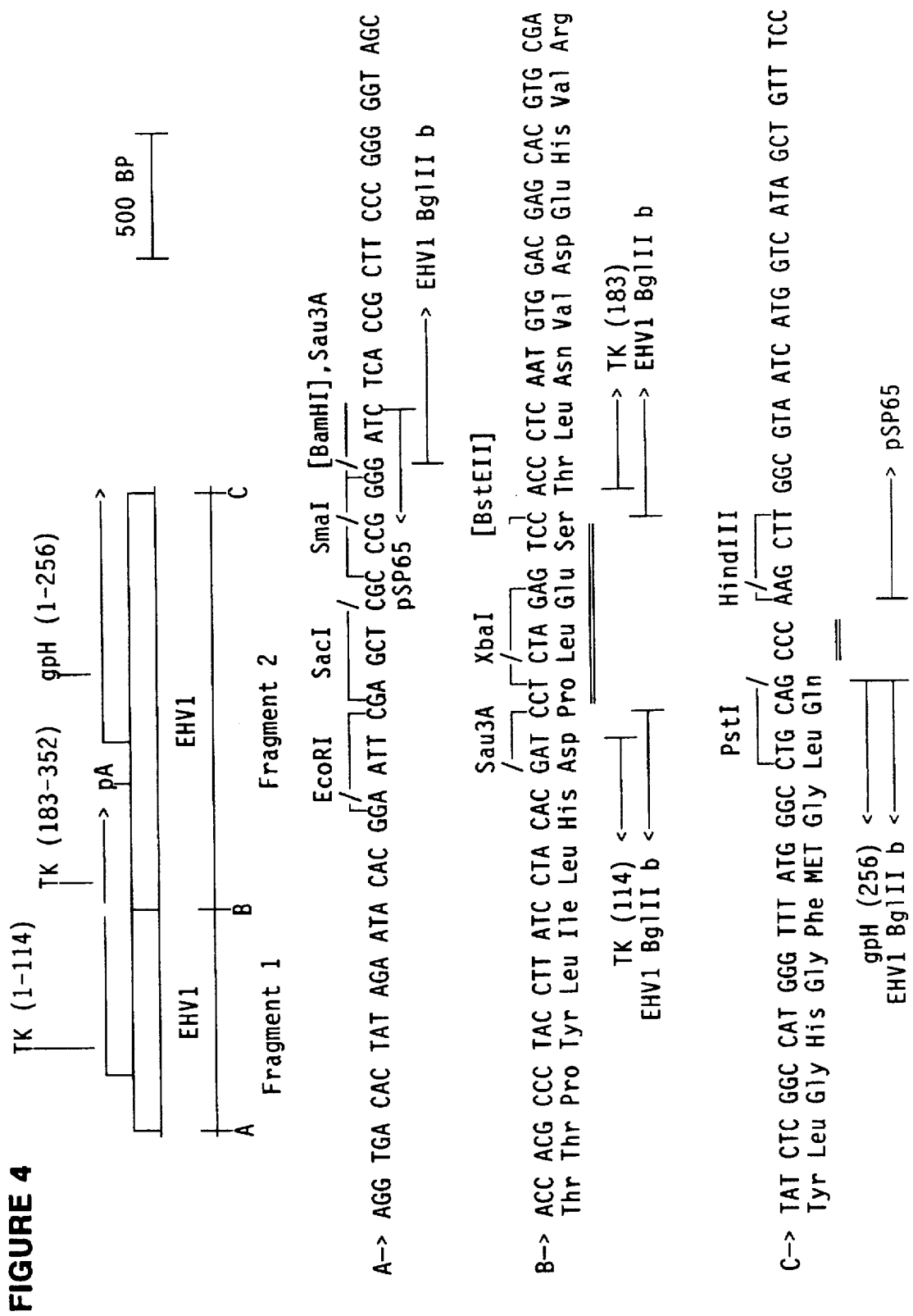
FIG. 4 Detailed description of the DNA insertion in Homology Vector 450-46.B4. The diagram shows the orientation of DNA fragments assembled in plasmid 450-46.B4. The origin of each fragment is described in the Materials and Methods section. The sequences located at the junctions between each fragment are shown, including junction A (SEQ ID NO: 14), junction B (SEQ ID NO: 15), and junction C (SEQ ID NO: 17). The restriction sites used to generate each fragment as well as synthetic linker sequences which were used to join the fragments are described for each junction. The synthetic linker sequences are underlined by a double bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, equine herpesvirus 1 (EHV1), thymidine kinase (TK), glycoprotein H (gpH), and poly adenylation signal (pA).

(iii) HYPOTHETICAL: NO (iv) ANTI-SENSE: NO (vi) ORIGINAL SOURCE:
    (A) ORGANISM: Plasmid (vii) IMMEDIATE SOURCE:
    (B) CLONE: 450-46.B4 (Figure 4 Junction A)

(xi) SEQUENCE DESCRIPTION: SEQ ID NO:14:

```
AGGTGACACT ATAGAATACA CGGAATTCGA GCTCGCCCGG GGATCTCACC GCTTCCCGGG      60

GGTAGC                                                                 66
```

( 2 ) INFORMATION FOR SEQ ID NO:15:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 450-46.B4 (Figure 4 Junction B)

( i x ) FEATURE:
        ( A ) NAME/KEY: CDS
        ( B ) LOCATION: 1..66
        ( D ) OTHER INFORMATION: /product="Region of deleted EHV1
        thymidine kinase gene"

( x i ) SEQUENCE DESCRIPTION: SEQ ID NO:15:

```
ACC ACG CCC TAC CTT ATC CTA CAC GAT CCT CTA GAG TCC ACC CTC AAT        48
Thr Thr Pro Tyr Leu Ile Leu His Asp Pro Leu Glu Ser Thr Leu Asn
 1               5                  10                  15

GTG GAC GAG CAC GTG CGA                                                66
Val Asp Glu His Val Arg
                20
```

( 2 ) INFORMATION FOR SEQ ID NO:16:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Thr Thr Pro Tyr Leu Ile Leu His Asp Pro Leu Glu Ser Thr Leu Asn
 1               5                  10                  15

Val Asp Glu His Val Arg
                20
```

( 2 ) INFORMATION FOR SEQ ID NO:17:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 450-46.B4 (Figure 4 Junction C)

( i x ) FEATURE:
 ( A ) NAME/KEY: CDS
 ( B ) LOCATION: 1..30
 ( D ) OTHER INFORMATION: /partial
  / codon_start=1
  / product="Region of EHV1 glycoprotein H gene"

( x i ) SEQUENCE DESCRIPTION: SEQ ID NO:17:

```
TAT CTC GGC CAT GGG TTT ATG GGC CTG CAG CCCAAGCTTG GCGTAATCAT     50
Tyr Leu Gly His Gly Phe Met Gly Leu Gln
  1             5                  10

GGTCATAGCT GTTTCC                                                 66
```

( 2 ) INFORMATION FOR SEQ ID NO:18:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( x i ) SEQUENCE DESCRIPTION: SEQ ID NO:18:

```
Tyr Leu Gly His Gly Phe Met Gly Leu Gln
  1             5                  10
```

( 2 ) INFORMATION FOR SEQ ID NO:19:

( i ) SEQUENCE CHARACTERISTICS:
( A ) LENGTH: 66 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 467-21.19 (Figure 5 Junction A)

( x i ) SEQUENCE DESCRIPTION: SEQ ID NO:19:

```
CACTATAGAA TACACGGCGA GCTCGCCCGG GGATCCACCG AGGGTGTGGG AGGTGGTAGC     60

GGAGGC                                                                66
```

( 2 ) INFORMATION FOR SEQ ID NO:20:

( i ) SEQUENCE CHARACTERISTICS:
( A ) LENGTH: 66 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 467-21.19 (Figure 5 Junction B)

( i x ) FEATURE:
( A ) NAME/KEY: CDS ( B ) LOCATION: 1..30
( D ) OTHER INFORMATION: /partial
/ codon_start=1
/ product="Region of EHV1 US2 gene"

( i x ) FEATURE:
( A ) NAME/KEY: CDS
( B ) LOCATION: 33..65
( D ) OTHER INFORMATION: /partial
/ codon_start=33
/ product="Region of EHV1 US2 gene"

(xi) SEQUENCE DESCRIPTION: SEQ ID NO:20:

```
GTG TGT GGA AAA CTG TTT GAG ACA ATA CCA TG AAT TCA TTA GTT CGT      47
Val Cys Gly Lys Leu Phe Glu Thr Ile Pro    Asn Ser Leu Val Arg
  1             5                   10       1               5

CCA CCC ACA GTT AAG CGG G                                           66
Pro Pro Thr Val Lys Arg
                10
```

(2) INFORMATION FOR SEQ ID NO:21:

(i) SEQUENCE CHARACTERISTICS:
(A) LENGTH: 10 amino acids
(B) TYPE: amino acid
(D) TOPOLOGY: linear (ii) MOLECULE TYPE: protein (xi) SEQUENCE DESCRIPTION: SEQ ID NO:21:

```
Val Cys Gly Lys Leu Phe Glu Thr Ile Pro
  1             5                   10
```

(2) INFORMATION FOR SEQ ID NO:22:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:22:

```
Asn Ser Leu Val Arg Pro Pro Thr Val Lys Arg
  1             5                   10
```

(2) INFORMATION FOR SEQ ID NO:23:

(i) SEQUENCE CHARACTERISTICS:
(A) LENGTH: 66 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 467-21.19 (Figure 5 Junction C)

(xi) SEQUENCE DESCRIPTION: SEQ ID NO:23:

```
GGGCCAGGCA GCCCCGCAGC CGCGCGCACG TGTCTGCAGC CCAAGCTTGG CGTAATCATG      60

GTCATA                                                                 66
```

( 2 ) INFORMATION FOR SEQ ID NO:24:

( i ) SEQUENCE CHARACTERISTICS:
    ( A ) LENGTH: 66 base pairs
    ( B ) TYPE: nucleic acid
    ( C ) STRANDEDNESS: double
    ( D ) TOPOLOGY: circular ( i i ) MOLECULE TYPE: DNA (genomic)

Figure 6:
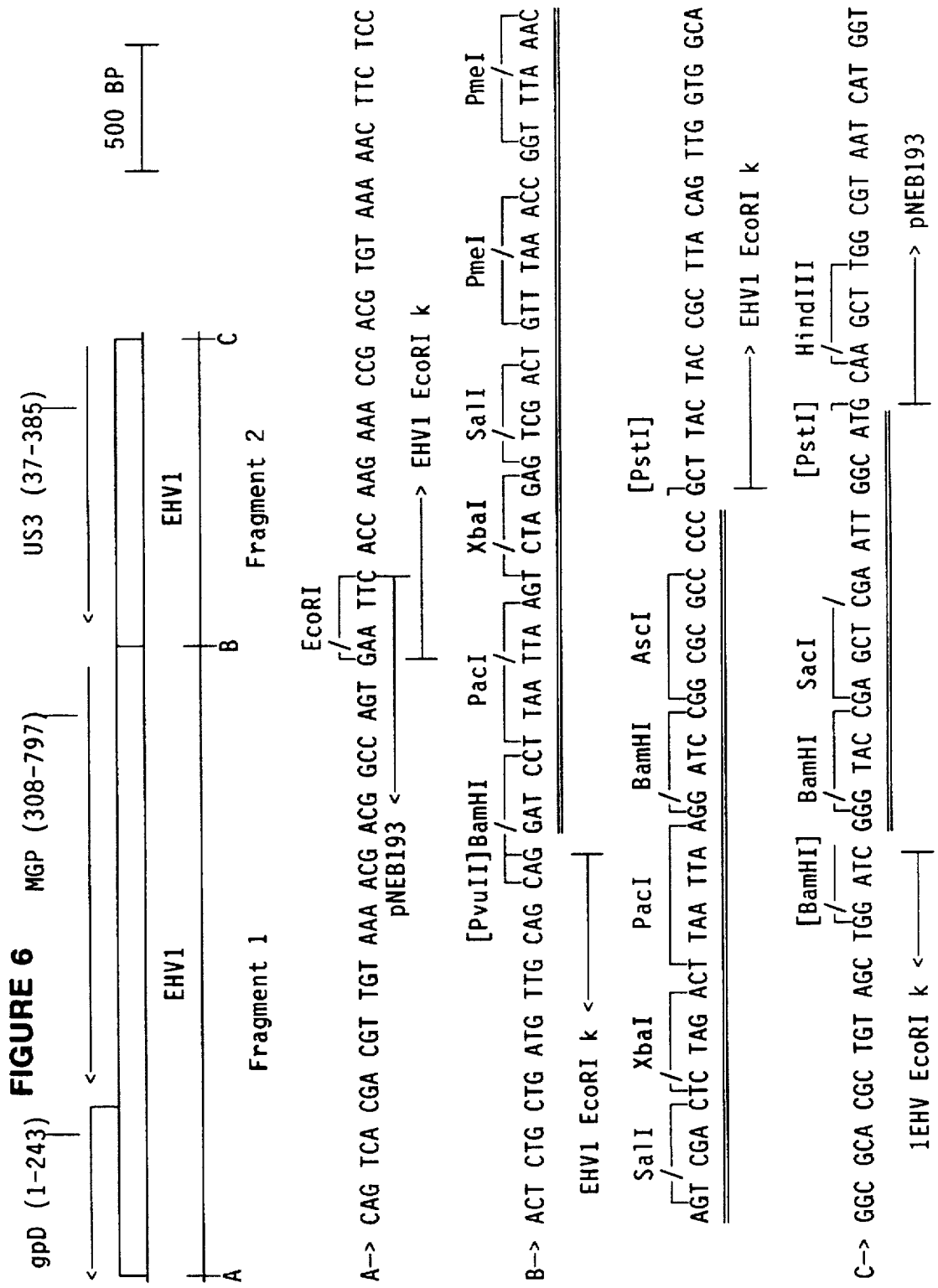
FIG. 6 Detailed description of the DNA insertion in Homology Vector 536-85.30. The diagram shows the orientation of DNA fragments assembled in plasmid 536-85.30. The origin of each fragment is described in the Materials and Methods section. The sequences located at the junctions between each fragment are shown, including junction A (SEQ ID NO: 24), junction B (SEQ ID NO: 25), and junction C (SEQ ID NO: 26). The restriction sites used to generate each fragment are indicated at the appropriate junction. The location of the gpD, MGP, and US3 gene coding regions ares also given. Restriction sites in brackets [ ] indicate the remnants of sites which were destroyed during construction. The following abbreviations are used, equine herpesvirus 1 (EHV1), membrane glycoprotein (MGP), unique short 3 (US3) glycoprotein D (gpD).

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 536-85.30 (Figure 6 Junction A)

( x i ) SEQUENCE DESCRIPTION: SEQ ID NO:24:

```
CAGTCACGAC GTTGTAAAAC GACGGCCAGT GAATTCACCA AGAAACCGAC GTGTAAAAAC      60

TTCTCC                                                                66
```

( 2 ) INFORMATION FOR SEQ ID NO:25:

( i ) SEQUENCE CHARACTERISTICS:
    ( A ) LENGTH: 132 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 536-85.30 (Figure 6 Junction B)

( x i ) SEQUENCE DESCRIPTION: SEQ ID NO:25:

```
ACTCTGCTGA TGTTGCAGCA GGATCCTTAA TTAAGTCTAG AGTCGACTGT TTAAACCGGT      60

TTAAACAGTC GACTCTAGAC TTAATTAAGG ATCCGGCGCG CCCCGCTTA CTACCGCTTA      120

CAGTTGGTGG CA                                                         132
```

( 2 ) INFORMATION FOR SEQ ID NO:26:

( i ) SEQUENCE CHARACTERISTICS:
    ( A ) LENGTH: 66 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 536-85.30 (Figure 6 Junction C)

( x i ) SEQUENCE DESCRIPTION: SEQ ID NO:26:

```
GGCGCACGCT GTAGCTGGAT CGGGTACCGA GCTCGAATTG GCATGCAAGC TTGGCGTAAT      60
```

CATGGT                                                                                            66

( 2 ) INFORMATION FOR SEQ ID NO:27:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

Figure 7:
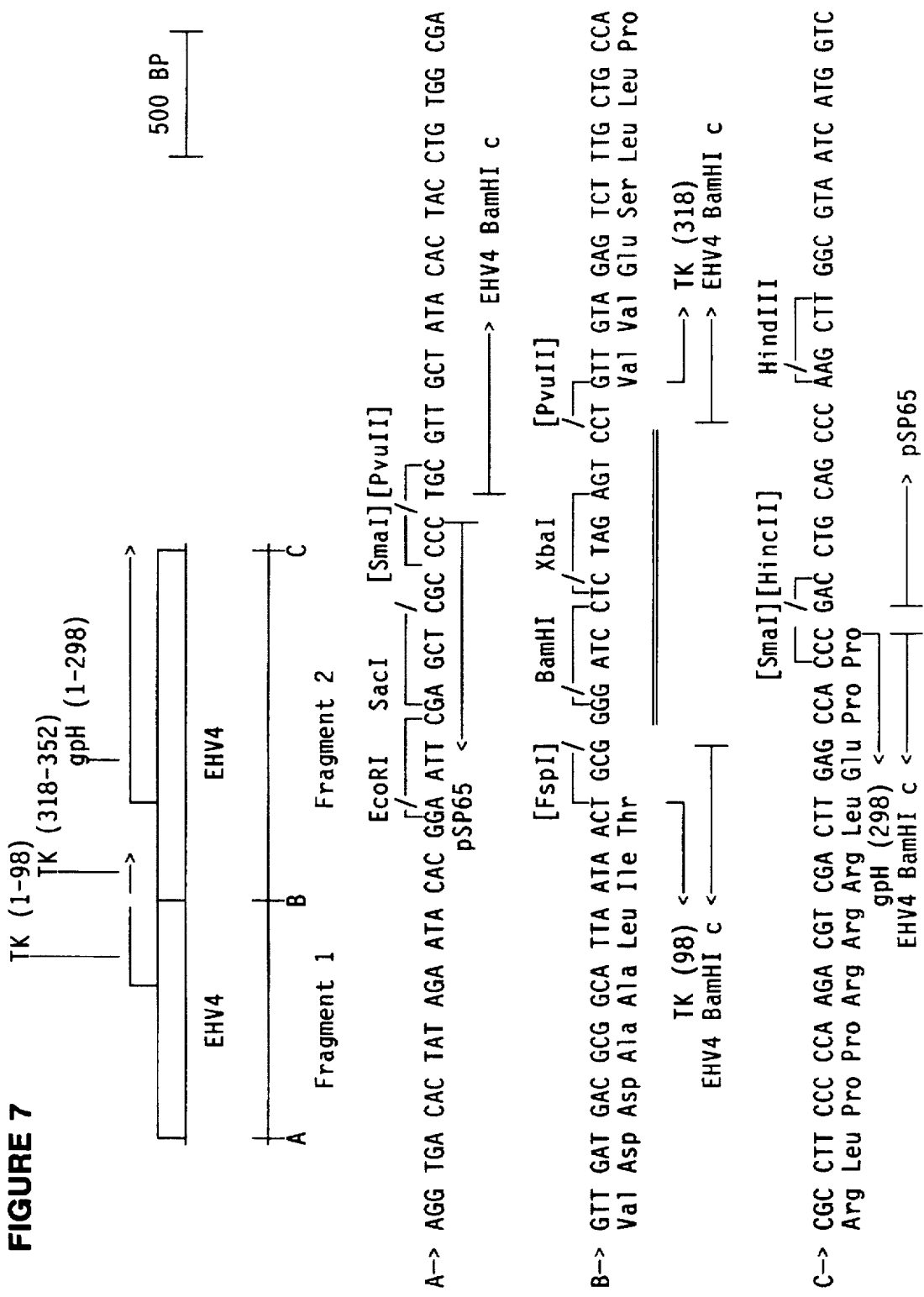
FIG. 7 Detailed description of the DNA insertion in Homology Vector 495-61.39. The diagram shows the orientation of DNA fragments assembled in plasmid 495-61.39. The origin of each fragment is described in the Materials and Methods section. The sequences located at the junctions between each fragment are shown, including junction A (SEQ ID NO: 27), junction B (SEQ ID NO: 28), and junction C (SEQ ID NO: 31). The restriction sites used to generate each fragment as well as synthetic linker sequences which were used to join the fragments are described for each junction. The synthetic linker sequences are underlined by a double bar. The location of the TK and gpH gene coding regions are also given. The following two conventions are used: numbers in parenthesis ( ) refer to amino acids, and restriction sites in brackets [ ] indicate the remnants of sites which were destroyed during construction. The following abbreviations are used, equine herpesvirus 4 (EHV4) and glycoprotein H (gpH).

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 495-61.39 (Figure 7 Junction A)

( x i ) SEQUENCE DESCRIPTION: SEQ ID NO:27:

AGGTGACACT ATAGAATACA CGGAATTCGA GCTCGCCCCT GCGTTGCTAT ACACTACCTG    60

TGGCGA                                                              66

( 2 ) INFORMATION FOR SEQ ID NO:28:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 495-61.39 (Figure 7 Junction B)

( i x ) FEATURE:
        ( A ) NAME/KEY: CDS
        ( B ) LOCATION: 1..24
        ( D ) OTHER INFORMATION: /partial
          / codon_start=1
          / product="Region of deleted EHV4 thymidine kinase
          gene"

( i x ) FEATURE:
        ( A ) NAME/KEY: CDS
        ( B ) LOCATION: 46..66
        ( D ) OTHER INFORMATION: /partial
          / codon_start=46
          / product="Region of deleted EHV4 thymidine kinase
          gene"

( x i ) SEQUENCE DESCRIPTION: SEQ ID NO:28:

```
GTT GAT GAC GCG GCA TTA ATA ACT GCGGGATCC TCTAGAGTCC T GTT GTA     51
Val Asp Asp Ala Ala Leu Ile Thr                          Val Val
 1               5                                         1

GAG TCT TTG CTG CCA                                                66
Glu Ser Leu Leu Pro
         5
```

( 2 ) INFORMATION FOR SEQ ID NO:29:

( i ) SEQUENCE CHARACTERISTICS:

(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:29:

Val Asp Asp Ala Ala Leu Ile Thr
 1               5

(2) INFORMATION FOR SEQ ID NO:30:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:30:

Val Val Glu Ser Leu Leu Pro
 1               5

(2) INFORMATION FOR SEQ ID NO:31:

(i) SEQUENCE CHARACTERISTICS:
(A) LENGTH: 66 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 495-61.39 (Figure 7 Junction C)

(ix) FEATURE:
(A) NAME/KEY: CDS
(B) LOCATION: 1..33
(D) OTHER INFORMATION: /partial
 / codon_start=1
 / product="Region of EHV4 glycoprotein H gene"

(xi) SEQUENCE DESCRIPTION: SEQ ID NO:31:

CGC CTT CCC CCA AGA CGT CGA CTT GAG CCA CCC GACCTGCAGC CCAAGCTTGG    53
Arg Leu Pro Pro Arg Arg Arg Leu Glu Pro Pro
 1               5                   10

CGTAATCATG GTC    66

(2) INFORMATION FOR SEQ ID NO:32:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:32:

Arg Leu Pro Pro Arg Arg Arg Leu Glu Pro Pro
 1               5                   10

(2) INFORMATION FOR SEQ ID NO:33:

( i ) SEQUENCE CHARACTERISTICS:
    ( A ) LENGTH: 66 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 523-38.9 (Figure 8 Junction A)

( x i ) SEQUENCE DESCRIPTION: SEQ ID NO:33:

ATACACATAC GATTTAGGTG ACACTATAGA ATACACGGAA TTCGAGCTCG CCCGGGGATC     60

CTCTAG     66

( 2 ) INFORMATION FOR SEQ ID NO:34:

( i ) SEQUENCE CHARACTERISTICS:
    ( A ) LENGTH: 66 base pairs
    ( B ) TYPE: nucleic acid
    ( C ) STRANDEDNESS: double
    ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 523-38.9 (Figure 8 Junction B)

( i x ) FEATURE:
    ( A ) NAME/KEY: CDS
    ( B ) LOCATION: 1..33
    ( D ) OTHER INFORMATION: /partial
        / codon_start=1
        / product="Region of deleted EHV4 US2 gene"

( x i ) SEQUENCE DESCRIPTION: SEQ ID NO:34:

AGG CCA TAC CAC CTA TGG GTT TTG GGA GCT GCA GGCACCGAAG TTTTTCGCTG     53
Arg Pro Tyr His Leu Trp Val Leu Gly Ala Ala
 1               5                   10

TAACTCTTGC TCG     66

( 2 ) INFORMATION FOR SEQ ID NO:35:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO:35:

Arg Pro Tyr His Leu Trp Val Leu Gly Ala Ala
 1               5                   10

( 2 ) INFORMATION FOR SEQ ID NO:36:

( i ) SEQUENCE CHARACTERISTICS:
    ( A ) LENGTH: 66 base pairs ( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 523-38.9 (Figure 8 Junction C)

( x i ) SEQUENCE DESCRIPTION: SEQ ID NO:36:

CCCGTGCAAC AAGAGTCGTC TTCCTCGTCC GAAAAGCTTG GCGTAATCAT GGTCATAGCT    60

GTTTCC    66

( 2 ) INFORMATION FOR SEQ ID NO:37:

( i ) SEQUENCE CHARACTERISTICS:
( A ) LENGTH: 66 base pairs
( B ) TYPE: nucleic acid
( C ) STRANDEDNESS: double
( D ) TOPOLOGY: circular ( i i ) MOLECULE TYPE: DNA (genomic)

Figure 9:
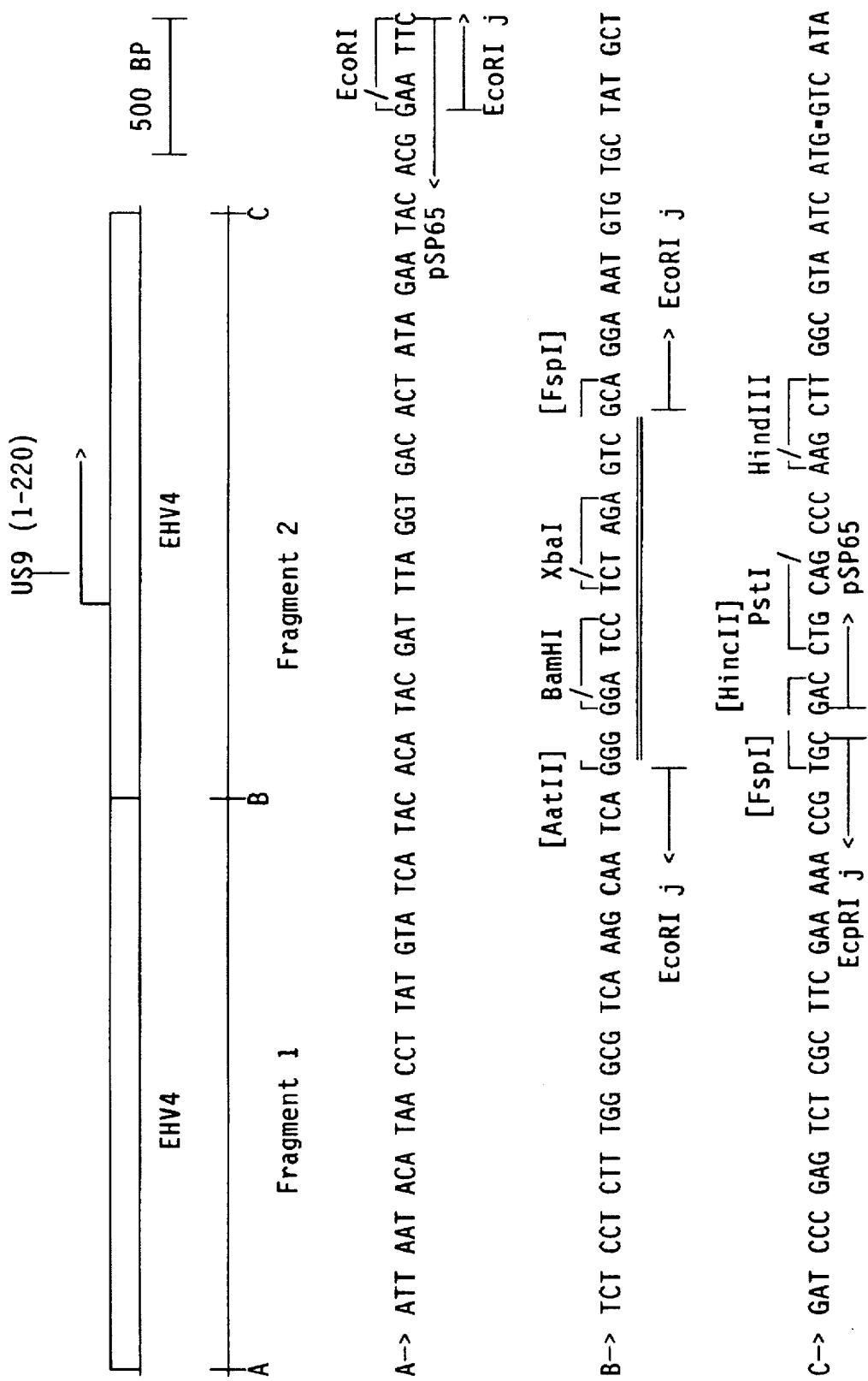
FIG. 9 Detailed description of the DNA insertion in Homology Vector 580-57.25. The diagram shows the orientation of DNA fragments assembled in plasmid 580-57.25. The origin of each fragment is described in the Materials and Methods section. The sequences located at the junctions between each fragment are shown, including junction A (SEQ ID NO: 37), junction B (SEQ ID NO: 38), and junction C (SEQ ID NO: 39). The restriction sites used to generate each fragment are indicated at the appropriate junction. The location of the US9 gene coding region is also given. The following two conventions are used: numbers in parenthesis ( ) refer to amino acids, and restriction sites in brackets [ ] indicate the remnants of sites which were destroyed during construction. The following abbreviations are used, equine herpesvirus 4 (EHV4) and unique short 9 (US9).

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 580-57.25 (Figure 9 Junction A)

( x i ) SEQUENCE DESCRIPTION: SEQ ID NO:37:

ATTAATACAT AACCTTATGT ATCATACACA TACGATTTAG GTGACACTAT AGAATACACG    60

GAATTC    66

( 2 ) INFORMATION FOR SEQ ID NO:38:

( i ) SEQUENCE CHARACTERISTICS:
( A ) LENGTH: 66 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Plasmid ( v i i ) IMMEDIATE SOURCE:
( B ) CLONE: 580-57.25 (Figure 9 Junction B)

( x i ) SEQUENCE DESCRIPTION: SEQ ID NO:38:

TCTCCTCTTT GGGCGTCAAA GCAATCAGGG GGATCCTCTA GAGTCGCAGG AAATGTGTGC    60

TATGCT    66

( 2 ) INFORMATION FOR SEQ ID NO:39:

( i ) SEQUENCE CHARACTERISTICS:

(A) LENGTH: 66 base pairs
(B) TYPE: nucleic acid
(C) STRANDEDNESS: double
(D) TOPOLOGY: circular (i i) MOLECULE TYPE: DNA (genomic)

(i i i) HYPOTHETICAL: NO (i v) ANTI-SENSE: NO (v i) ORIGINAL SOURCE:
(A) ORGANISM: Plasmid (v i i) IMMEDIATE SOURCE:
(B) CLONE: 580-57.25 (Figure 9 Junction C)

(x i) SEQUENCE DESCRIPTION: SEQ ID NO:39:

```
GATCCCGAGT CTCGCTTCGA AAAACCGTGC GACCTGCAGC CCAAGCTTGG CGTAATCATG    60
GTCATA                                                              66
```

(2) INFORMATION FOR SEQ ID NO:40:

(i) SEQUENCE CHARACTERISTICS:
(A) LENGTH: 66 base pairs
(B) TYPE: nucleic acid
(C) STRANDEDNESS: double
(D) TOPOLOGY: circular (i i) MOLECULE TYPE: DNA (genomic)

(i i i) HYPOTHETICAL: NO (i v) ANTI-SENSE: NO (v i) ORIGINAL SOURCE:
(A) ORGANISM: Plasmid (v i i) IMMEDIATE SOURCE:
(B) CLONE: 467-22.A12 (Figure 10 Junction A)

(x i) SEQUENCE DESCRIPTION: SEQ ID NO:40:

```
GAATTCGAGC TCGCCCGGGG ATCCTCTAGA GTCGACGTCT GGGGCGCGGG GGTGGTGCTC    60
TTCGAG                                                              66
```

(2) INFORMATION FOR SEQ ID NO:41:

(i) SEQUENCE CHARACTERISTICS:
(A) LENGTH: 66 base pairs
(B) TYPE: nucleic acid
(C) STRANDEDNESS: double
(D) TOPOLOGY: circular (i i) MOLECULE TYPE: DNA (genomic)

(i i i) HYPOTHETICAL: NO (i v) ANTI-SENSE: NO (v i) ORIGINAL SOURCE:
(A) ORGANISM: Plasmid (v i i) IMMEDIATE SOURCE:
(B) CLONE: 467-22.A12 (Figure 10 Junction B)

(i x) FEATURE:
(A) NAME/KEY: CDS
(B) LOCATION: 16..66
(D) OTHER INFORMATION: /partial
/ codon_start=16
/ product="N-terminal peptide of hybrid protein"

(x i) SEQUENCE DESCRIPTION: SEQ ID NO:41:

```
CTCCACAGCT CAACA ATG AAG TGG GCA ACG TGG ATC GAT CCC GTC GTT TTA        51
               Met Lys Trp Ala Thr Trp Ile Asp Pro Val Val Leu
                1             5                  10

CAA CGT CGT GAC TGG                                                      66
Gln Arg Arg Asp Trp
         15
```

( 2 ) INFORMATION FOR SEQ ID NO:42:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Met Lys Trp Ala Thr Trp Ile Asp Pro Val Val Leu Gln Arg Arg Asp
 1             5                  10                  15

Trp
```

( 2 ) INFORMATION FOR SEQ ID NO:43:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 467-22.A12 (Figure 10 Junction C)

( i x ) FEATURE:
        ( A ) NAME/KEY: CDS
        ( B ) LOCATION: 1..93
        ( D ) OTHER INFORMATION: /partial
            / codon_start=1
            / function="Translational finish of hybrid
            protein"
            / product="C-terminal peptide"
            / standard_name="Translation of synthetic DNA
            sequence"

( x i ) SEQUENCE DESCRIPTION: SEQ ID NO:43:

```
GAC GAC TCC TGG AGC CCG TCA GTA TCG GCG GAA ATC CAG CTG AGC GCC        48
Asp Asp Ser Trp Ser Pro Ser Val Ser Ala Glu Ile Gln Leu Ser Ala
 1               5                  10                  15

GGT CGC TAC CAT TAC CAG TTG GTC TGG TGT CAA AAA GAT CTA GAA             93
Gly Arg Tyr His Tyr Gln Leu Val Trp Cys Gln Lys Asp Leu Glu
             20              25                  30

TAAGCTAGAG GATCGATCCC CTATGGCGAT CATCAGGGC                              132
```

( 2 ) INFORMATION FOR SEQ ID NO:44:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| Asp | Asp | Ser | Trp | Ser | Pro | Ser | Val | Ser | Ala | Glu | Ile | Gln | Leu | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Arg | Tyr | His | Tyr | Gln | Leu | Val | Trp | Cys | Gln | Lys | Asp | Leu | Glu |
|-----|-----|-----|-----|-----|-----|-----|-----|-----|-----|-----|-----|-----|-----|-----|
|     |     |     | 20  |     |     |     |     | 25  |     |     |     | 30  |     |     |

( 2 ) INFORMATION FOR SEQ ID NO:45:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 467-22.A12 (Figure 10 Junction D)

( x i ) SEQUENCE DESCRIPTION: SEQ ID NO:45:

```
AACGAGGGCC AGTACCGGCG CCTGGTGTCC GTCGACTCTA GAGGATCCCC GGGCGAGCTC    60

GAATTC                                                               66
```

( 2 ) INFORMATION FOR SEQ ID NO:46:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 523-42.A18 (Figure 11 Junction A)

( x i ) SEQUENCE DESCRIPTION: SEQ ID NO:46:

```
AAGCTTGGCC TCGAGGGCCG CGGCCGCCTG CAGGTCGACG TCTGGGCGC GGGGGTGGTG     60

CTCTTC                                                               66
```

( 2 ) INFORMATION FOR SEQ ID NO:47:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:

(B) CLONE: 523-42.A18 (Figure 11 Junction B)

(ix) FEATURE:
(A) NAME/KEY: CDS
(B) LOCATION: 16..66
(D) OTHER INFORMATION: /partial
/ codon_start=16
/ product="N-terminal peptide of hybrid protein"

(xi) SEQUENCE DESCRIPTION: SEQ ID NO:47:

```
CTCCACAGCT CAACA ATG AAG TGG GCA ACG TGG ATC GAT CCC GTC GTT TTA        51
                Met Lys Trp Ala Thr Trp Ile Asp Pro Val Val Leu
                1               5                       10

CAA CGT CGT GAC TGG                                                      66
Gln Arg Arg Asp Trp
            15
```

(2) INFORMATION FOR SEQ ID NO:48:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:48:

```
Met Lys Trp Ala Thr Trp Ile Asp Pro Val Val Leu Gln Arg Arg Asp
1               5                       10                  15

Trp
```

(2) INFORMATION FOR SEQ ID NO:49:

(i) SEQUENCE CHARACTERISTICS:
(A) LENGTH: 132 base pairs
(B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (vi) ORIGINAL SOURCE:
(A) ORGANISM: Plasmid (vii) IMMEDIATE SOURCE:
(B) CLONE: 523-42.A18 (Figure 11 Junction C)

(ix) FEATURE:
(A) NAME/KEY: CDS
(B) LOCATION: 1..93
(D) OTHER INFORMATION: /partial
/ codon_start=1
/ function="Translational fininsh of hybrid protein"
/ product="C-terminal peptide"
/ standard_name="Translation of synthetic DNA sequence"

(xi) SEQUENCE DESCRIPTION: SEQ ID NO:49:

```
GAC GAC TCC TGG AGC CCG TCA GTA TCG GCG GAA ATC CAG CTG AGC GCC         48
Asp Asp Ser Trp Ser Pro Ser Val Ser Ala Glu Ile Gln Leu Ser Ala
1               5                       10                  15

GGT CGC TAC CAT TAC CAG TTG GTC TGG TGT CAA AAA GAT CTA GAA             93
Gly Arg Tyr His Tyr Gln Leu Val Trp Cys Gln Lys Asp Leu Glu
            20                  25                  30

TAAGCTAGAG GATCGATCCC CTATGGCGAT CATCAGGGC                              132
```

( 2 ) INFORMATION FOR SEQ ID NO:50:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

```
Asp Asp Ser Trp Ser Pro Ser Val Ser Ala Glu Ile Gln Leu Ser Ala
 1               5                  10                  15
Gly Arg Tyr His Tyr Gln Leu Val Trp Cys Gln Lys Asp Leu Glu
            20                  25                  30
```

( 2 ) INFORMATION FOR SEQ ID NO:51:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 523-42.A18 (Figure 11 Junction D)

( x i ) SEQUENCE DESCRIPTION: SEQ ID NO:51:

```
GAGGGCCAGT ACCGGCGCCT GGTGTCCGTC GACCTGCAGG CGGCCGCGGC CCTCGAGGCC    60
AAGCTT                                                               66
```

( 2 ) INFORMATION FOR SEQ ID NO:52:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 552-45.19 (Figure 12 Junction A)

( x i ) SEQUENCE DESCRIPTION: SEQ ID NO:52:

```
TCTAGAGTCA GCTTGGCCTC GAGGGCCGCG GCCGCCTGCA GGTCGAGATC CCCTCGACGT    60
CTGGGG                                                               66
```

( 2 ) INFORMATION FOR SEQ ID NO:53:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular (i i) MOLECULE TYPE: DNA (genomic)

(i i i) HYPOTHETICAL: NO (i v) ANTI-SENSE: NO (v i) ORIGINAL SOURCE:
    (A) ORGANISM: Plasmid (v i i) IMMEDIATE SOURCE:
    (B) CLONE: 552-45.19 (Figure 12 Junction B)

(i x) FEATURE:
    (A) NAME/KEY: CDS
    (B) LOCATION: 31..66
    (D) OTHER INFORMATION: /partial
        / codon_start=31
        / product="N-terminal peptide of hybrid protein"

(x i) SEQUENCE DESCRIPTION: SEQ ID NO:53:

```
CACACCTTTG  CGCATCTCCA  CAGCTCAACA  ATG  AAT  TCC  ATG  TTA  CGT  CCT  GTA       54
                                    Met  Asn  Ser  Met  Leu  Arg  Pro  Val
                                     1                  5

GAA  ACC  CCA  ACC                                                                66
Glu  Thr  Pro  Thr
      10
```

(2) INFORMATION FOR SEQ ID NO:54:

(i) SEQUENCE CHARACTERISTICS:
        (A) LENGTH: 12 amino acids
        (B) TYPE: amino acid
        (D) TOPOLOGY: linear (i i) MOLECULE TYPE: protein (x i) SEQUENCE DESCRIPTION: SEQ ID NO:54:

```
Met  Asn  Ser  Met  Leu  Arg  Pro  Val  Glu  Thr  Pro  Thr
 1                   5                  10
```

(2) INFORMATION FOR SEQ ID NO:55:

(i) SEQUENCE CHARACTERISTICS:
        (A) LENGTH: 66 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: NO (i v) ANTI-SENSE: NO (v i) ORIGINAL SOURCE:
        (A) ORGANISM: Plasmid (v i i) IMMEDIATE SOURCE:
        (B) CLONE: 552-45.19 (Figure 12 Junction C)

(i x) FEATURE:
        (A) NAME/KEY: CDS
        (B) LOCATION: 1..15
        (D) OTHER INFORMATION: /partial
            / codon_start=1
            / product="C-terminal peptide of hybrid protein"

(x i) SEQUENCE DESCRIPTION: SEQ ID NO:55:

```
CAG  GGA  GGC  AAA  CAA  TGAATCAACA  ACTCTCCCGG  GAGATGGGGG  AGGCTAACTG    55
Gln  Gly  Gly  Lys  Gln
 1                   5

AAACACGGAA  G                                                               66
```

( 2 ) INFORMATION FOR SEQ ID NO:56:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

Gln Gly Gly Lys Gln
 1                5

( 2 ) INFORMATION FOR SEQ ID NO:57:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 552-45.19 (Figure 12 Junction D)

( x i ) SEQUENCE DESCRIPTION: SEQ ID NO:57:

```
TGCTGCGTTC  CCGGGGATCT  CGACCTGCAG  GGCGGCCGCG  GCCCTCGAGG  CCAAGCTGAC    60

TCTAGA                                                                    66
```

( 2 ) INFORMATION FOR SEQ ID NO:58:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 593-31.2 (Figure 13 Junction A)

( x i ) SEQUENCE DESCRIPTION: SEQ ID NO:58:

```
GTCGACTCTA  GACTTAATTA  AGGATCCGGC  GCGCCCCTC  GACGTCTGGG  GCGCGGGGT     60

GGTGCT                                                                    66
```

( 2 ) INFORMATION FOR SEQ ID NO:59:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Plasmid ( v i i ) IMMEDIATE SOURCE:
    ( B ) CLONE: 593-31.2 (Figure 13 Junction B)

( i x ) FEATURE:
    ( A ) NAME/KEY: CDS
    ( B ) LOCATION: 16..66
    ( D ) OTHER INFORMATION: /partial
        / product="N-terminal peptide of hybrid protein"
        / gene="16"

( x i ) SEQUENCE DESCRIPTION: SEQ ID NO:59:

```
CTCCACAGCT CAACA ATG AAG TGG GCA ACG TGG ATC GAT CCC GTC GTT TTA      51
                Met Lys Trp Ala Thr Trp Ile Asp Pro Val Val Leu
                 1           5                       10

CAA CGT CGT GAC TGG                                                    66
Gln Arg Arg Asp Trp
            15
```

( 2 ) INFORMATION FOR SEQ ID NO:60:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Met Lys Trp Ala Thr Trp Ile Asp Pro Val Val Leu Gln Arg Arg Asp
 1           5                       10                      15

Trp
```

( 2 ) INFORMATION FOR SEQ ID NO:61:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 593-31.2 (Figure 13 Junction C)

( i x ) FEATURE:
        ( A ) NAME/KEY: CDS
        ( B ) LOCATION: 1..93
        ( D ) OTHER INFORMATION: /partial
            / product="C-terminal peptide of hybrid protein"
            / gene="1"

( x i ) SEQUENCE DESCRIPTION: SEQ ID NO:61:

```
GAC GAC TCC TGG AGC CCG TCA GTA TCG GCG GAA ATC CAG CTG AGC GCC       48
Asp Asp Ser Trp Ser Pro Ser Val Ser Ala Glu Ile Gln Leu Ser Ala
 1           5                       10                      15

GGT CGC TAC CAT TAC CAG TTG GTC TGG TGT CAA AAA GAT CTA GAA            93
```

| Gly | Arg | Tyr | His | Tyr | Gln | Leu | Val | Trp | Cys | Gln | Lys | Asp | Leu | Glu |
| | | | 20 | | | | 25 | | | | | 30 | | |

TAAGCTAGAG GATCGATCCC CTATGGCGAT CATCAGGGC        132

( 2 ) INFORMATION FOR SEQ ID NO:62:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

| Asp | Asp | Ser | Trp | Ser | Pro | Ser | Val | Ser | Ala | Glu | Ile | Gln | Leu | Ser | Ala |
| 1 | | | | 5 | | | | | 10 | | | | | 15 | |

| Gly | Arg | Tyr | His | Tyr | Gln | Leu | Val | Trp | Cys | Gln | Lys | Asp | Leu | Glu |
| | | | 20 | | | | 25 | | | | | 30 | | |

( 2 ) INFORMATION FOR SEQ ID NO:63:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Synthetic oligonucleotide primer ( x i ) SEQUENCE DESCRIPTION: SEQ ID NO:63:

GGGTCGACAT GAAGACAACC ATTATTTTGA TAC        33

( 2 ) INFORMATION FOR SEQ ID NO:64:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 593-31.2 (Figure 13 Junction D)

( x i ) SEQUENCE DESCRIPTION: SEQ ID NO:64:

GCCAGTACCG GCGCCTGGTG TCCGTCGAGG GGGCGCGCCG GATCCTTAAT TAAGTCTAGA        60

GTCGAC        66

( 2 ) INFORMATION FOR SEQ ID NO:65:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
 ( A ) ORGANISM: Synthetic oligonucleotide primer ( x i ) SEQUENCE DESCRIPTION: SEQ ID NO:65:

GGGTCGACTC AAATGCAAAT GTTGCATCTG AT     32

( 2 ) INFORMATION FOR SEQ ID NO:66:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Synthetic oligonucleotide primer ( x i ) SEQUENCE DESCRIPTION: SEQ ID NO:66:

GGGATCCATG AACACTCAAA TTCTAATATT AG     32

( 2 ) INFORMATION FOR SEQ ID NO:67:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Synthetic oligonucleotide primer ( x i ) SEQUENCE DESCRIPTION: SEQ ID NO:67:

GGGATCCTTA TATACAAATA GTGCACCGCA     30

( 2 ) INFORMATION FOR SEQ ID NO:68:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Synthetic oligonucleotide primer ( x i ) SEQUENCE DESCRIPTION: SEQ ID NO:68:

GGGATCCTTA TATACAAATA GTGCACCGCA     30

( 2 ) INFORMATION FOR SEQ ID NO:69:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Synthetic oligonucleotide primer ( x i ) SEQUENCE DESCRIPTION: SEQ ID NO:69:

GGGTCGACTT ACATCTTATC GATGTCAAA    29

( 2 ) INFORMATION FOR SEQ ID NO:70:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Synthetic oligonucleotide primer ( x i ) SEQUENCE DESCRIPTION: SEQ ID NO:70:

GGGATCCATG AATCCTAATC AAAAACTCTT T    31

( 2 ) INFORMATION FOR SEQ ID NO:71:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Synthetic oligonucleotide primer ( x i ) SEQUENCE DESCRIPTION: SEQ ID NO:71:

GGGATCCTTA CGAAAAGTAT TTAATTTGTG C    31

What is claimed is:

1. A live recombinant equine herpesvirus 4 (EHV-4) which comprises the genomic DNA of equine herpesvirus 4 from which a DNA sequence encoding the EHV-4 homologue of herpes simplex virus 1 (HSV-1) US2 gene product has been deleted.

2. The live recombinant equine herpesvirus of claim 1, designated S-4EHV-003 (ATCC Accession No. VR 2363).

3. The live recombinant equine herpesvirus of claim 1, wherein the genomic DNA contains a further deletion of a DNA sequence encoding thymidine kinase.

4. The live recombinant equine herpesvirus of claim 1, wherein the genomic DNA contains a further deletion of a DNA sequence encoding glycoprotein gE.

5. The live recombinant equine herpesvirus of claim 1, wherein the genomic DNA further contains a foreign DNA sequence inserted into the region encoding EHV-4 homologue of HSV-1 US2 gene product, thymidine kinase, or glycoprotein gE, such that the foreign DNA sequence is capable of being expressed in a host cell infected with the live recombinant equine herpesvirus.

6. The live recombinant Equine Herpesvirus of claim 1, designated S-4EHV-014.

7. The live recombinant equine herpesvirus of claim 3, designated S-4EHV-002 (ATCC Accession No. VR 2362).

8. The live recombinant equine herpesvirus of claim 4, wherein the genomic DNA contains a further deletion of a DNA sequence encoding thymidine kinase.

9. The live recombinant equine herpesvirus of claim 8, designated S-4EHV-011.

10. The live recombinant equine herpesvirus of claim 8, designated S-4EHV-012.

11. The live recombinant equine herpesvirus of claim 8, designated S-4EHV-013.

12. The live recombinant equine herpesvirus of claim 5, wherein the foreign DNA sequence is inserted within the region encoding the EHV-4 homologue of HSV-1 US2 gene product.

13. The live recombinant equine herpesvirus of claim 5, wherein the foreign DNA sequence is inserted within the region encoding thymidine kinase.

14. The live recombinant equine herpesvirus of claim 5, wherein the foreign DNA sequence is inserted within the region encoding glycoprotein gE.

15. The live recombinant equine herpesvirus of claim 5, wherein the foreign DNA sequence encodes a polypeptide.

16. The live recombinant equine herpesvirus of claim 15, wherein the polypeptide encodes a detectable marker.

17. The live recombinant equine herpesvirus of claim 15, wherein the foreign DNA sequence encodes an antigenic polypeptide.

18. The live recombinant equine herpesvirus of claim 16, wherein the detectable marker is *E. coli* β-galactosidase.

19. The live recombinant equine herpesvirus of claim 17, wherein the antigenic polypeptide encodes equine herpesvirus 1 (EHV-1) glycoprotein gB, glycoprotein gC, glycoprotein gD or glycoprotein gH.

20. The live recombinant equine herpesvirus of claim 17, wherein the antigenic polypeptide encodes the hemagglutinin and neuraminidase genes of the Influenza A/equine/Prague/56 isolate of equine influenza virus.

21. The live recombinant equine herpesvirus of claim 17, wherein the antigenic polypeptide encodes the hemagglutinin and neuraminidase genes of the Influenza A/equine/Miami/63 isolate of equine influenza virus.

22. The live recombinant equine herpesvirus of claim 17, wherein the antigenic polypeptide encodes the hemagglutinin and neuraminidase genes of the Influenza A/equine/Kentucky/81 isolate of equine influenza virus.

23. The live recombinant equine herpesvirus of claim 17, wherein the antigenic polypeptide encodes the hemagglutinin and neuraminidase genes of the Influenza A/equine/Alaska/91 isolate of equine influenza virus.

* * * * *